US012723093B2

(12) United States Patent
Wang et al.

(10) Patent No.: US 12,723,093 B2
(45) Date of Patent: Sep. 1, 2026

(54) TL1A-BINDING MOLECULES, IL-23p19-BINDING MOLECULES, AND BISPECIFIC ANTIGEN-BINDING MOLECULES, AND USES THEREOF

(71) Applicant: Newsoara Biopharmaceutical Technology (Suzhou) Co., Ltd., JiangSu Province (CN)

(72) Inventors: Wenyi Wang, JiangSu Province (CN); Qingqing Yin, JiangSu Province (CN); Yuannian Li, JiangSu Province (CN)

(73) Assignee: Newsoara Biopharmaceutical Technology (Suzhou) Co., Ltd., JiangSu (CN)

( * ) Notice: Subject to any disclaimer, the term of this patent is extended or adjusted under 35 U.S.C. 154(b) by 0 days.

(21) Appl. No.: 19/084,984

(22) Filed: Mar. 20, 2025

(65) Prior Publication Data

US 2026/0201047 A1 Jul. 16, 2026

(30) Foreign Application Priority Data

Jan. 13, 2025 (CN) ......................... 202510052108.3

(51) Int. Cl.
*C07K 16/00* (2006.01)
*A61P 29/00* (2006.01)
*C07K 16/24* (2006.01)
*C07K 16/28* (2006.01)

(52) U.S. Cl.
CPC .......... *C07K 16/2875* (2013.01); *A61P 29/00* (2018.01); *C07K 16/244* (2013.01); *C07K 2317/24* (2013.01); *C07K 2317/31* (2013.01); *C07K 2317/522* (2013.01); *C07K 2317/565* (2013.01); *C07K 2317/569* (2013.01); *C07K 2317/76* (2013.01); *C07K 2317/92* (2013.01)

(58) Field of Classification Search
CPC ...................... C07K 2317/31; C07K 2317/569
See application file for complete search history.

(56) References Cited

FOREIGN PATENT DOCUMENTS

WO WO 2023/133538 * 7/2023 ............. A61K 41/00

* cited by examiner

*Primary Examiner* — Mark Halvorson
(74) *Attorney, Agent, or Firm* — Dority & Manning, PA

(57) ABSTRACT

The present disclosure relates to TL1A-binding molecules, IL-23p19-binding molecules, and bispecific antigen-binding molecules that simultaneously target TL1A and IL-23p19. The disclosure also relates to nucleic acid molecules encoding said antigen-binding molecules, expression vectors, host cells, compositions thereof, and their use for treating diseases.

23 Claims, 6 Drawing Sheets

Specification includes a Sequence Listing.

| | HYB1803 | HYB1805 | Duvakitug | 1D1 | PRA-023 |
|---|---|---|---|---|---|
| $EC_{50}$(μg/mL) | 0.0167 | 0.0152 | 0.0149 | 0.0277 | 0.1823 |

| | HYB1803 | HYB1805 | Duvakitug | 1D1 | PRA-023 |
|---|---|---|---|---|---|
| $EC_{50}$(μg/mL) | 0.748 | 0.636 | 0.606 | 2.152 | 2.287 |

|  | HYB1803 | HYB1805 | Duvakitug | 1D1 | PRA-023 |
| --- | --- | --- | --- | --- | --- |
| $EC_{50}$(μg/mL) | 0.1622 | 0.1088 | 0.0741 | 0.3022 | 2.673 |

| | HYB1903 | Risankizumab |
|---|---|---|
| EC$_{50}$(μg/mL) | 0.006 | 0.099 |

| | HYB1903 | Risankizumab |
|---|---|---|
| EC$_{50}$(μg/mL) | 0.030 | 0.126 |

| | HYB1903-hz3 | Risankizumab |
|---|---|---|
| $EC_{50}$(μg/mL) | 0.012 | 0.022 |

| | HYB1805-2 | HYB1805-3 | Risankizumab |
|---|---|---|---|
| $EC_{50}$(μg/mL) | 0.022 | 0.023 | 0.01 |

| | HYB1805-2 | Duvakitug | PRA-023 |
|---|---|---|---|
| $EC_{50}$(ng/mL) | 5.2 | 25.8 | 226.7 |

SEQUENCE LISTING

```
Sequence total quantity: 119
SEQ ID NO: 1            moltype = AA  length = 10
FEATURE                 Location/Qualifiers
source                  1..10
                        mol_type = protein
                        organism = synthetic construct
SEQUENCE: 1
GFTFDDYAMH                                                           10

SEQ ID NO: 2            moltype = AA  length = 10
```

```
FEATURE                Location/Qualifiers
source                 1..10
                       mol_type = protein
                       organism = synthetic construct
SEQUENCE: 2
GISWNSGSIG                                                       10

SEQ ID NO: 3           moltype = AA  length = 10
FEATURE                Location/Qualifiers
source                 1..10
                       mol_type = protein
                       organism = synthetic construct
SEQUENCE: 3
DSGAYVSFDY                                                       10

SEQ ID NO: 4           moltype = AA  length = 11
FEATURE                Location/Qualifiers
source                 1..11
                       mol_type = protein
                       organism = synthetic construct
SEQUENCE: 4
RASQSISSYL N                                                     11

SEQ ID NO: 5           moltype = AA  length = 7
FEATURE                Location/Qualifiers
source                 1..7
                       mol_type = protein
                       organism = synthetic construct
SEQUENCE: 5
AASSLQS                                                          7

SEQ ID NO: 6           moltype = AA  length = 10
FEATURE                Location/Qualifiers
source                 1..10
                       mol_type = protein
                       organism = synthetic construct
SEQUENCE: 6
QESYSYPPFT                                                       10

SEQ ID NO: 7           moltype = AA  length = 119
FEATURE                Location/Qualifiers
source                 1..119
                       mol_type = protein
                       organism = synthetic construct
SEQUENCE: 7
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCARDS GAYVSFDYWG QGTLVTVSS   119

SEQ ID NO: 8           moltype = AA  length = 108
FEATURE                Location/Qualifiers
source                 1..108
                       mol_type = protein
                       organism = synthetic construct
SEQUENCE: 8
DIQMTQSPSS LSASVGDRVT ITCRASQSIS SYLNWYQQKP GKAPKLLIYA ASSLQSGVPS  60
RFSGSGSGTD FTLTISSLQP EDFATYYCQE SYSYPPFTFG GGTKVEIK              108

SEQ ID NO: 9           moltype = AA  length = 10
FEATURE                Location/Qualifiers
source                 1..10
                       mol_type = protein
                       organism = synthetic construct
SEQUENCE: 9
GFTFSSYAMS                                                       10

SEQ ID NO: 10          moltype = AA  length = 10
FEATURE                Location/Qualifiers
source                 1..10
                       mol_type = protein
                       organism = synthetic construct
SEQUENCE: 10
AISGSGGSTY                                                       10

SEQ ID NO: 11          moltype = AA  length = 10
FEATURE                Location/Qualifiers
source                 1..10
                       mol_type = protein
                       organism = synthetic construct
SEQUENCE: 11
```

```
LEWLYGAFDI                                                       10

SEQ ID NO: 12           moltype = AA  length = 11
FEATURE                 Location/Qualifiers
source                  1..11
                        mol_type = protein
                        organism = synthetic construct
SEQUENCE: 12
RASQGISSWL A                                                     11

SEQ ID NO: 13           moltype = AA  length = 10
FEATURE                 Location/Qualifiers
source                  1..10
                        mol_type = protein
                        organism = synthetic construct
SEQUENCE: 13
QQADSFPPLT                                                       10

SEQ ID NO: 14           moltype = AA  length = 119
FEATURE                 Location/Qualifiers
source                  1..119
                        mol_type = protein
                        organism = synthetic construct
SEQUENCE: 14
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARLE WLYGAFDIWG QGTLVTVSS   119

SEQ ID NO: 15           moltype = AA  length = 108
FEATURE                 Location/Qualifiers
source                  1..108
                        mol_type = protein
                        organism = synthetic construct
SEQUENCE: 15
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ ADSFPPLTFG GGTKVEIK             108

SEQ ID NO: 16           moltype = AA  length = 10
FEATURE                 Location/Qualifiers
source                  1..10
                        mol_type = protein
                        organism = synthetic construct
SEQUENCE: 16
SYEDTAHFDY                                                       10

SEQ ID NO: 17           moltype = AA  length = 11
FEATURE                 Location/Qualifiers
source                  1..11
                        mol_type = protein
                        organism = synthetic construct
SEQUENCE: 17
RASQSISSWL A                                                     11

SEQ ID NO: 18           moltype = AA  length = 7
FEATURE                 Location/Qualifiers
source                  1..7
                        mol_type = protein
                        organism = synthetic construct
SEQUENCE: 18
DASSLES                                                          7

SEQ ID NO: 19           moltype = AA  length = 9
FEATURE                 Location/Qualifiers
source                  1..9
                        mol_type = protein
                        organism = synthetic construct
SEQUENCE: 19
QQYNSFPPT                                                        9

SEQ ID NO: 20           moltype = AA  length = 119
FEATURE                 Location/Qualifiers
source                  1..119
                        mol_type = protein
                        organism = synthetic construct
SEQUENCE: 20
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCARSY EDTAHFDYWG QGTLVTVSS   119

SEQ ID NO: 21           moltype = AA  length = 107
FEATURE                 Location/Qualifiers
```

```
source                  1..107
                        mol_type = protein
                        organism = synthetic construct
SEQUENCE: 21
DIQMTQSPST LSASVGDRVT ITCRASQSIS SWLAWYQQKP GKAPKLLIYD ASSLESGVPS  60
RFSGSGSGTE FTLTISSLQP DDFATYYCQQ YNSFPPTFGG GTKVEIK               107

SEQ ID NO: 22           moltype = AA  length = 11
FEATURE                 Location/Qualifiers
source                  1..11
                        mol_type = protein
                        organism = synthetic construct
SEQUENCE: 22
GQVAPLDHFD Y                                                      11

SEQ ID NO: 23           moltype = AA  length = 9
FEATURE                 Location/Qualifiers
source                  1..9
                        mol_type = protein
                        organism = synthetic construct
SEQUENCE: 23
EQYNSYPLT                                                         9

SEQ ID NO: 24           moltype = AA  length = 120
FEATURE                 Location/Qualifiers
source                  1..120
                        mol_type = protein
                        organism = synthetic construct
SEQUENCE: 24
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCAKGQ VAPLDHFDYW GQGTLVTVSS  120

SEQ ID NO: 25           moltype = AA  length = 107
FEATURE                 Location/Qualifiers
source                  1..107
                        mol_type = protein
                        organism = synthetic construct
SEQUENCE: 25
DIQMTQSPST LSASVGDRVT ITCRASQSIS SWLAWYQQKP GKAPKLLIYD ASSLESGVPS  60
RFSGSGSGTE FTLTISSLQP DDFATYYCEQ YNSYPLTFGG GTKVEIK               107

SEQ ID NO: 26           moltype = AA  length = 10
FEATURE                 Location/Qualifiers
source                  1..10
                        mol_type = protein
                        organism = synthetic construct
SEQUENCE: 26
GFTFSSYAMH                                                        10

SEQ ID NO: 27           moltype = AA  length = 10
FEATURE                 Location/Qualifiers
source                  1..10
                        mol_type = protein
                        organism = synthetic construct
SEQUENCE: 27
VISYDGSNKY                                                        10

SEQ ID NO: 28           moltype = AA  length = 11
FEATURE                 Location/Qualifiers
source                  1..11
                        mol_type = protein
                        organism = synthetic construct
SEQUENCE: 28
GQVAILDYFD Y                                                      11

SEQ ID NO: 29           moltype = AA  length = 9
FEATURE                 Location/Qualifiers
source                  1..9
                        mol_type = protein
                        organism = synthetic construct
SEQUENCE: 29
QQYNSYPPT                                                         9

SEQ ID NO: 30           moltype = AA  length = 120
FEATURE                 Location/Qualifiers
source                  1..120
                        mol_type = protein
                        organism = synthetic construct
SEQUENCE: 30
```

```
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARGQ VAILDYFDYW GQGTLVTVSS  120

SEQ ID NO: 31          moltype = AA  length = 107
FEATURE                Location/Qualifiers
source                 1..107
                       mol_type = protein
                       organism = synthetic construct
SEQUENCE: 31
DIQMTQSPST LSASVGDRVT ITCRASQSIS SWLAWYQQKP GKAPKLLIYD ASSLESGVPS  60
RFSGSGSGTE FTLTISSLQP DDFATYYCQQ YNSYPPTFGG GTKVEIK               107

SEQ ID NO: 32          moltype = AA  length = 11
FEATURE                Location/Qualifiers
source                 1..11
                       mol_type = protein
                       organism = synthetic construct
SEQUENCE: 32
LGDGVTYAFD I                                                      11

SEQ ID NO: 33          moltype = AA  length = 10
FEATURE                Location/Qualifiers
source                 1..10
                       mol_type = protein
                       organism = synthetic construct
SEQUENCE: 33
QQSLDFPPIT                                                        10

SEQ ID NO: 34          moltype = AA  length = 120
FEATURE                Location/Qualifiers
source                 1..120
                       mol_type = protein
                       organism = synthetic construct
SEQUENCE: 34
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARLG DGVTYAFDIW GQGTLVTVSS  120

SEQ ID NO: 35          moltype = AA  length = 108
FEATURE                Location/Qualifiers
source                 1..108
                       mol_type = protein
                       organism = synthetic construct
SEQUENCE: 35
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SLDFPPITFG GGTKVEIK              108

SEQ ID NO: 36          moltype = AA  length = 13
FEATURE                Location/Qualifiers
source                 1..13
                       mol_type = protein
                       organism = synthetic construct
SEQUENCE: 36
LPSSGSYTAH FDY                                                    13

SEQ ID NO: 37          moltype = AA  length = 8
FEATURE                Location/Qualifiers
source                 1..8
                       mol_type = protein
                       organism = synthetic construct
SEQUENCE: 37
QQGFSFWT                                                          8

SEQ ID NO: 38          moltype = AA  length = 122
FEATURE                Location/Qualifiers
source                 1..122
                       mol_type = protein
                       organism = synthetic construct
SEQUENCE: 38
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARLP SSGSYTAHFD YWGQGTLVTV  120
SS                                                                122

SEQ ID NO: 39          moltype = AA  length = 106
FEATURE                Location/Qualifiers
source                 1..106
                       mol_type = protein
                       organism = synthetic construct
SEQUENCE: 39
DIQMTQSPSS VSASVGDRVT ITCRASQGIS SWLAWYQQKP GKAPKLLIYA ASSLQSGVPS  60
```

-continued

```
RFSGSGSGTD FTLTISSLQP EDFATYYCQQ GFSFWTFGGG TKVEIK                 106

SEQ ID NO: 40           moltype = AA  length = 17
FEATURE                 Location/Qualifiers
source                  1..17
                        mol_type = protein
                        organism = synthetic construct
SEQUENCE: 40
EGSSSGYSRH GYDYFDY                                                 17

SEQ ID NO: 41           moltype = AA  length = 9
FEATURE                 Location/Qualifiers
source                  1..9
                        mol_type = protein
                        organism = synthetic construct
SEQUENCE: 41
QQYRSYPIT                                                          9

SEQ ID NO: 42           moltype = AA  length = 126
FEATURE                 Location/Qualifiers
source                  1..126
                        mol_type = protein
                        organism = synthetic construct
SEQUENCE: 42
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCAREG SSSGYSRHGY DYFDYWGQGT  120
LVTVSS                                                             126

SEQ ID NO: 43           moltype = AA  length = 107
FEATURE                 Location/Qualifiers
source                  1..107
                        mol_type = protein
                        organism = synthetic construct
SEQUENCE: 43
DIQMTQSPST LSASVGDRVT ITCRASQSIS SWLAWYQQKP GKAPKLLIYD ASSLESGVPS  60
RFSGSGSGTE FTLTISSLQP DDFATYYCQQ YRSYPITFGG GTKVEIK                107

SEQ ID NO: 44           moltype = AA  length = 10
FEATURE                 Location/Qualifiers
source                  1..10
                        mol_type = protein
                        organism = synthetic construct
SEQUENCE: 44
GFTFSNFNMK                                                         10

SEQ ID NO: 45           moltype = AA  length = 10
FEATURE                 Location/Qualifiers
source                  1..10
                        mol_type = protein
                        organism = synthetic construct
SEQUENCE: 45
SIISSGGTTG                                                         10

SEQ ID NO: 46           moltype = AA  length = 8
FEATURE                 Location/Qualifiers
source                  1..8
                        mol_type = protein
                        organism = synthetic construct
SEQUENCE: 46
RRRDSEDY                                                           8

SEQ ID NO: 47           moltype = AA  length = 117
FEATURE                 Location/Qualifiers
source                  1..117
                        mol_type = protein
                        organism = synthetic construct
SEQUENCE: 47
QLQLVESGGG LVQPGGSLRL SCAASGFTFS NFNMKWYRQV SGKERELVAS IISSGGTTGY  60
ADSVKGRFTI SRDNAKNTVY LQMNSLKTED TAVYYCNARR RDSEDYWGQG TQVTVSS     117

SEQ ID NO: 48           moltype = AA  length = 10
FEATURE                 Location/Qualifiers
source                  1..10
                        mol_type = protein
                        organism = synthetic construct
SEQUENCE: 48
GSFFRSIAMA                                                         10

SEQ ID NO: 49           moltype = AA  length = 9
```

```
FEATURE                 Location/Qualifiers
source                  1..9
                        mol_type = protein
                        organism = synthetic construct
SEQUENCE: 49
TITSDGDTN                                                        9

SEQ ID NO: 50           moltype = AA  length = 6
FEATURE                 Location/Qualifiers
source                  1..6
                        mol_type = protein
                        organism = synthetic construct
SEQUENCE: 50
PGSIGY                                                           6

SEQ ID NO: 51           moltype = AA  length = 114
FEATURE                 Location/Qualifiers
source                  1..114
                        mol_type = protein
                        organism = synthetic construct
SEQUENCE: 51
QVQLVESGGG LVQPGGSLRL SCAASGSFFR SIAMAWYRQA PGKQRVLVGT ITSDGDTNYA  60
DSVKGRFTIS RDNAKNTMYL QMNSLKPEDT AVYSCNVPGS IGYWSQGTQV TVSS        114

SEQ ID NO: 52           moltype = AA  length = 10
FEATURE                 Location/Qualifiers
source                  1..10
                        mol_type = protein
                        organism = synthetic construct
SEQUENCE: 52
GRTLSSYAMG                                                       10

SEQ ID NO: 53           moltype = AA  length = 7
FEATURE                 Location/Qualifiers
source                  1..7
                        mol_type = protein
                        organism = synthetic construct
SEQUENCE: 53
SIGRSTY                                                          7

SEQ ID NO: 54           moltype = AA  length = 14
FEATURE                 Location/Qualifiers
source                  1..14
                        mol_type = protein
                        organism = synthetic construct
SEQUENCE: 54
PIVAGFGTVV SGEY                                                  14

SEQ ID NO: 55           moltype = AA  length = 120
FEATURE                 Location/Qualifiers
source                  1..120
                        mol_type = protein
                        organism = synthetic construct
SEQUENCE: 55
QVQLVESGGG LVQAGGSLRL SCAASGRTLS SYAMGWFRQA PGKEREFVAS IGRSTYYADP  60
VKGRFTISRD NAKNTVYLQM NSLKSEDTAV YYCNAPIVAG FGTVVSGEYW GQGTQVTVSS  120

SEQ ID NO: 56           moltype = AA  length = 10
FEATURE                 Location/Qualifiers
source                  1..10
                        mol_type = protein
                        organism = synthetic construct
SEQUENCE: 56
GSIGNIYDLG                                                       10

SEQ ID NO: 57           moltype = AA  length = 9
FEATURE                 Location/Qualifiers
source                  1..9
                        mol_type = protein
                        organism = synthetic construct
SEQUENCE: 57
SITSGGRTI                                                        9

SEQ ID NO: 58           moltype = AA  length = 6
FEATURE                 Location/Qualifiers
source                  1..6
                        mol_type = protein
                        organism = synthetic construct
SEQUENCE: 58
```

```
GHELGY                                                           6

SEQ ID NO: 59           moltype = AA  length = 114
FEATURE                 Location/Qualifiers
source                  1..114
                        mol_type = protein
                        organism = synthetic construct
SEQUENCE: 59
QVQLVESGGG LVQPGESLTL SCTVSGSIGN IYDLGWYRQA SGKQRELVAS ITSGGRTIYA  60
DSVEGRFTIS RNNAKNTVVL QMNSLEPEDM AVYYCNLGHE LGYWGQGTQV TVSS        114

SEQ ID NO: 60           moltype = AA  length = 10
FEATURE                 Location/Qualifiers
source                  1..10
                        mol_type = protein
                        organism = synthetic construct
SEQUENCE: 60
GFTFSTYAMA                                                       10

SEQ ID NO: 61           moltype = AA  length = 10
FEATURE                 Location/Qualifiers
source                  1..10
                        mol_type = protein
                        organism = synthetic construct
SEQUENCE: 61
SIDTSGDNTH                                                       10

SEQ ID NO: 62           moltype = AA  length = 10
FEATURE                 Location/Qualifiers
source                  1..10
                        mol_type = protein
                        organism = synthetic construct
SEQUENCE: 62
PNTGWGTRRY                                                       10

SEQ ID NO: 63           moltype = AA  length = 119
FEATURE                 Location/Qualifiers
source                  1..119
                        mol_type = protein
                        organism = synthetic construct
SEQUENCE: 63
QLQLVESGGG LVQPGGSLRL SCVASGFTFS TYAMAWYRQR PGKERELVAS IDTSGDNTHY  60
VGAVKGRFTI SRDNAKNTVY LQMNGLKPED TAVYFCNAPN TGWGTRRYWG QGTQVTVSS   119

SEQ ID NO: 64           moltype = AA  length = 10
FEATURE                 Location/Qualifiers
source                  1..10
                        mol_type = protein
                        organism = synthetic construct
SEQUENCE: 64
GFAFSTYAMA                                                       10

SEQ ID NO: 65           moltype = AA  length = 10
FEATURE                 Location/Qualifiers
source                  1..10
                        mol_type = protein
                        organism = synthetic construct
SEQUENCE: 65
SIDSSGDNTH                                                       10

SEQ ID NO: 66           moltype = AA  length = 119
FEATURE                 Location/Qualifiers
source                  1..119
                        mol_type = protein
                        organism = synthetic construct
SEQUENCE: 66
QLQLVESGGG LVQPGGSLRL SCVASGFAFS TYAMAWYRQR PGKERELVGS IDSSGDNTHY  60
VDAVKGRFTI SRDNAKNTVY LQMNVLKPED TAVYYCNSPN TGWGTRRYWG QGTQVTVSS   119

SEQ ID NO: 67           moltype = AA  length = 10
FEATURE                 Location/Qualifiers
source                  1..10
                        mol_type = protein
                        organism = synthetic construct
SEQUENCE: 67
GFTFSSYAMA                                                       10

SEQ ID NO: 68           moltype = AA  length = 10
FEATURE                 Location/Qualifiers
```

```
source                  1..10
                        mol_type = protein
                        organism = synthetic construct
SEQUENCE: 68
SIDSSGYNTH                                                       10

SEQ ID NO: 69           moltype = AA  length = 10
FEATURE                 Location/Qualifiers
source                  1..10
                        mol_type = protein
                        organism = synthetic construct
SEQUENCE: 69
PNTGWGSRRY                                                       10

SEQ ID NO: 70           moltype = AA  length = 119
FEATURE                 Location/Qualifiers
source                  1..119
                        mol_type = protein
                        organism = synthetic construct
SEQUENCE: 70
QLQLVESGGG LVQPGGSLRL SCAASGFTFS SYAMAWYRQR SGKERELVAS IDSSGYNTHY  60
TDAGKGRFTI SRDNAKNTVY LQMNNLKPED TAVYYCNAPN TGWGSRRYWG QGTQVTVSS   119

SEQ ID NO: 71           moltype = AA  length = 10
FEATURE                 Location/Qualifiers
source                  1..10
                        mol_type = protein
                        organism = synthetic construct
SEQUENCE: 71
GNIGHIYDLG                                                       10

SEQ ID NO: 72           moltype = AA  length = 9
FEATURE                 Location/Qualifiers
source                  1..9
                        mol_type = protein
                        organism = synthetic construct
SEQUENCE: 72
SITDNGRTI                                                        9

SEQ ID NO: 73           moltype = AA  length = 6
FEATURE                 Location/Qualifiers
source                  1..6
                        mol_type = protein
                        organism = synthetic construct
SEQUENCE: 73
GHWLGY                                                           6

SEQ ID NO: 74           moltype = AA  length = 114
FEATURE                 Location/Qualifiers
source                  1..114
                        mol_type = protein
                        organism = synthetic construct
SEQUENCE: 74
QVQLVESGGG LVQPGESLRL SCSVSGNIGH IYDLGWYRQA SGKQRELVAS ITDNGRTIYG  60
DSVKGRFTIS RNNVKNTVNL QMNSLTPEDT AVYYCNLGHW LGYWGQGTQV TVSS        114

SEQ ID NO: 75           moltype = AA  length = 120
FEATURE                 Location/Qualifiers
source                  1..120
                        mol_type = protein
                        organism = synthetic construct
SEQUENCE: 75
QVQLLESGGG LVQAGGSLRL SCAASGRTLS SYAMGWFRQA PGKGLEFVAS IGRSTYYADP  60
VKGRFTISRD NSKNTVYLQM NSLRAEDTAV YYCNAPIVAG FGTVVSGEYW GQGTLVTVSS  120

SEQ ID NO: 76           moltype = AA  length = 120
FEATURE                 Location/Qualifiers
source                  1..120
                        mol_type = protein
                        organism = synthetic construct
SEQUENCE: 76
QVQLLESGGG LVQPGGSLRL SCAASGRTLS SYAMGWFRQA PGKGLEFVAS IGRSTYYADP  60
VKGRFTISRD NSKNTVYLQM NSLRAEDTAV YYCNAPIVAG FGTVVSGEYW GQGTLVTVSS  120

SEQ ID NO: 77           moltype = AA  length = 120
FEATURE                 Location/Qualifiers
source                  1..120
                        mol_type = protein
                        organism = synthetic construct
```

```
SEQUENCE: 77
EVQLLESGGG LVQPGGSLRL SCAASGRTLS SYAMGWFRQA PGKGLEFVAS IGRSTYYADP  60
VKGRFTISRD NSKNTVYLQM NSLRAEDTAV YYCNAPIVAG FGTVVSGEYW GQGTLVTVSS  120

SEQ ID NO: 78           moltype = AA  length = 120
FEATURE                 Location/Qualifiers
source                  1..120
                        mol_type = protein
                        organism = synthetic construct
SEQUENCE: 78
QVQLLESGGG LVQPGGSLRL SCAASGRTLS SYAMGWFRQA PGKGLEFVAS IGRSTYYADS  60
VKGRFTISRD NSKNTVYLQM NSLRAEDTAV YYCNAPIVAG FGTVVSGEYW GQGTLVTVSS  120

SEQ ID NO: 79           moltype = AA  length = 120
FEATURE                 Location/Qualifiers
source                  1..120
                        mol_type = protein
                        organism = synthetic construct
SEQUENCE: 79
QVQLLESGGG LVQPGGSLRL SCAASGRTLS SYAMGWFRQA PGKGLEFVAS IGRSTYYADP  60
VKGRFTISRD NSKNTVYLQM NSLRAEDTAV YYCAAPIVAG FGTVVSGEYW GQGTLVTVSS  120

SEQ ID NO: 80           moltype = AA  length = 330
FEATURE                 Location/Qualifiers
source                  1..330
                        mol_type = protein
                        organism = synthetic construct
SEQUENCE: 80
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 81           moltype = AA  length = 330
FEATURE                 Location/Qualifiers
source                  1..330
                        mol_type = protein
                        organism = synthetic construct
SEQUENCE: 81
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 82           moltype = AA  length = 107
FEATURE                 Location/Qualifiers
source                  1..107
                        mol_type = protein
                        organism = synthetic construct
SEQUENCE: 82
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 83           moltype = AA  length = 449
FEATURE                 Location/Qualifiers
source                  1..449
                        mol_type = protein
                        organism = synthetic construct
SEQUENCE: 83
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCARDS GAYVSFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 84           moltype = AA  length = 215
FEATURE                 Location/Qualifiers
source                  1..215
                        mol_type = protein
                        organism = synthetic construct
SEQUENCE: 84
DIQMTQSPSS LSASVGDRVT ITCRASQSIS SYLNWYQQKP GKAPKLLIYA ASSLQSGVPS  60
```

```
RFSGSGSGTD FTLTISSLQP EDFATYYCQE SYSYPPFTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 85          moltype = AA  length = 449
FEATURE                Location/Qualifiers
source                 1..449
                       mol_type = protein
                       organism = synthetic construct
SEQUENCE: 85
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARLE WLYGAFDIWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 86          moltype = AA  length = 215
FEATURE                Location/Qualifiers
source                 1..215
                       mol_type = protein
                       organism = synthetic construct
SEQUENCE: 86
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ ADSFPPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 87          moltype = AA  length = 449
FEATURE                Location/Qualifiers
source                 1..449
                       mol_type = protein
                       organism = synthetic construct
SEQUENCE: 87
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCARSY EDTAHFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 88          moltype = AA  length = 214
FEATURE                Location/Qualifiers
source                 1..214
                       mol_type = protein
                       organism = synthetic construct
SEQUENCE: 88
DIQMTQSPST LSASVGDRVT ITCRASQSIS SWLAWYQQKP GKAPKLLIYD ASSLESGVPS  60
RFSGSGSGTE FTLTISSLQP DDFATYYCQQ YNSFPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 89          moltype = AA  length = 450
FEATURE                Location/Qualifiers
source                 1..450
                       mol_type = protein
                       organism = synthetic construct
SEQUENCE: 89
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCAKGQ VAPLDHFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 90          moltype = AA  length = 214
FEATURE                Location/Qualifiers
source                 1..214
                       mol_type = protein
                       organism = synthetic construct
SEQUENCE: 90
DIQMTQSPST LSASVGDRVT ITCRASQSIS SWLAWYQQKP GKAPKLLIYD ASSLESGVPS  60
RFSGSGSGTE FTLTISSLQP DDFATYYCEQ YNSYPLTFGG GTKVEIKRTV AAPSVFIFPP  120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 91           moltype = AA  length = 450
FEATURE                 Location/Qualifiers
source                  1..450
                        mol_type = protein
                        organism = synthetic construct
SEQUENCE: 91
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARGQ VAILDYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 92           moltype = AA  length = 214
FEATURE                 Location/Qualifiers
source                  1..214
                        mol_type = protein
                        organism = synthetic construct
SEQUENCE: 92
DIQMTQSPST LSASVGDRVT ITCRASQSIS SWLAWYQQKP GKAPKLLIYD ASSLESGVPS  60
RFSGSGSGTE FTLTISSLQP DDFATYYCQQ YNSYPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 93           moltype = AA  length = 450
FEATURE                 Location/Qualifiers
source                  1..450
                        mol_type = protein
                        organism = synthetic construct
SEQUENCE: 93
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARLG DGVTYAFDIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 94           moltype = AA  length = 215
FEATURE                 Location/Qualifiers
source                  1..215
                        mol_type = protein
                        organism = synthetic construct
SEQUENCE: 94
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SLDFPPITFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 95           moltype = AA  length = 452
FEATURE                 Location/Qualifiers
source                  1..452
                        mol_type = protein
                        organism = synthetic construct
SEQUENCE: 95
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARLP SSGSYTAHFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 96           moltype = AA  length = 213
FEATURE                 Location/Qualifiers
source                  1..213
                        mol_type = protein
                        organism = synthetic construct
SEQUENCE: 96
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ GFSFWTFGGG TKVEIKRTVA APSVFIFPPS  120
DEQLKSGTAS VVCLLNNFYP REAKVQWKVD NALQSGNSQE SVTEQDSKDS TYSLSSTLTL  180
```

-continued

```
SKADYEKHKV YACEVTHQGL SSPVTKSFNR GEC                             213

SEQ ID NO: 97            moltype = AA  length = 456
FEATURE                  Location/Qualifiers
source                   1..456
                         mol_type = protein
                         organism = synthetic construct
SEQUENCE: 97
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCAREG SSSGYSRHGY DYFDYWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                          456

SEQ ID NO: 98            moltype = AA  length = 214
FEATURE                  Location/Qualifiers
source                   1..214
                         mol_type = protein
                         organism = synthetic construct
SEQUENCE: 98
DIQMTQSPST LSASVGDRVT ITCRASQSIS SWLAWYQQKP GKAPKLLIYD ASSLESGVPS  60
RFSGSGSGTE FTLTISSLQP DDFATYYCQQ YRSYPITFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 99            moltype = AA  length = 232
FEATURE                  Location/Qualifiers
source                   1..232
                         mol_type = protein
                         organism = synthetic construct
SEQUENCE: 99
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK        232

SEQ ID NO: 100           moltype = AA  length = 232
FEATURE                  Location/Qualifiers
source                   1..232
                         mol_type = protein
                         organism = synthetic construct
SEQUENCE: 100
EPKSADKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK        232

SEQ ID NO: 101           moltype = AA  length = 349
FEATURE                  Location/Qualifiers
source                   1..349
                         mol_type = protein
                         organism = synthetic construct
SEQUENCE: 101
QLQLVESGGG LVQPGGSLRL SCAASGFTFS NFNMKWYRQV SGKERELVAS IISSGGTTGY  60
ADSVKGRFTI SRDNAKNTVY LQMNSLKTED TAVYYCNARR RDSEDYWGQG TQVTVSSEPK  120
SADKTHTCPP CPAPEAAGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSREEM TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPGK             349

SEQ ID NO: 102           moltype = AA  length = 346
FEATURE                  Location/Qualifiers
source                   1..346
                         mol_type = protein
                         organism = synthetic construct
SEQUENCE: 102
QVQLVESGGG LVQPGGSLRL SCAASGSFFR SIAMAWYRQA PGKQRVLVGT ITSDGDTNYA  60
DSVKGRFTIS RDNAKNTMYL QMNSLKPEDT AVYSCNVPGS IGYWSQGTQV TVSSEPKSAD  120
KTHTCPPCPA PEAAGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPGK                346

SEQ ID NO: 103           moltype = AA  length = 352
FEATURE                  Location/Qualifiers
source                   1..352
```

```
                        mol_type = protein
                        organism = synthetic construct
SEQUENCE: 103
QVQLVESGGG LVQAGGSLRL SCAASGRTLS SYAMGWFRQA PGKEREFVAS IGRSTYYADP  60
VKGRFTISRD NAKNTVYLQM NSLKSEDTAV YYCNAPIVAG FGTVVSGEYW GQGTQVTVSS  120
EPKSADKTHT CPPCPAPEAA GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 104          moltype = AA  length = 346
FEATURE                 Location/Qualifiers
source                  1..346
                        mol_type = protein
                        organism = synthetic construct
SEQUENCE: 104
QVQLVESGGG LVQPGESLTL SCTVSGSIGN IYDLGWYRQA SGKQRELVAS ITSGGRTIYA  60
DSVEGRFTIS RNNAKNTVVL QMNSLEPEDM AVYYCNLGHE LGYWGQGTQV TVSSEPKSAD  120
KTHTCPPCPA PEAAGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPGK                 346

SEQ ID NO: 105          moltype = AA  length = 351
FEATURE                 Location/Qualifiers
source                  1..351
                        mol_type = protein
                        organism = synthetic construct
SEQUENCE: 105
QLQLVESGGG LVQPGGSLRL SCVASGFTFS TYAMAWYRQR PGKERELVAS IDTSGDNTHY  60
VGAVKGRFTI SRDNAKNTVY LQMNGLKPED TAVYFCNAPN TGWGTRRYWG QGTQVTVSSE  120
PKSADKTHTC PPCPAPEAAG GPSVFLFPPK PKDTLMISRT PEVTCVVVDV SHEDPEVKFN  180
WYVDGVEVHN AKTKPREEQY NSTYRVVSVL TVLHQDWLNG KEYKCKVSNK ALPAPIEKTI  240
SKAKGQPREP QVYTLPPSRE EMTKNQVSLT CLVKGFYPSD IAVEWESNGQ PENNYKTTPP  300
VLDSDGSFFL YSKLTVDKSR WQQGNVFSCS VMHEALHNHY TQKSLSLSPG K           351

SEQ ID NO: 106          moltype = AA  length = 351
FEATURE                 Location/Qualifiers
source                  1..351
                        mol_type = protein
                        organism = synthetic construct
SEQUENCE: 106
QLQLVESGGG LVQPGGSLRL SCVASGFAFS TYAMAWYRQR PGKERELVGS IDSSGDNTHY  60
VDAVKGRFTI SRDNAKNTVY LQMNVLKPED TAVYYCNSPN TGWGTRRYWG QGTQVTVSSE  120
PKSADKTHTC PPCPAPEAAG GPSVFLFPPK PKDTLMISRT PEVTCVVVDV SHEDPEVKFN  180
WYVDGVEVHN AKTKPREEQY NSTYRVVSVL TVLHQDWLNG KEYKCKVSNK ALPAPIEKTI  240
SKAKGQPREP QVYTLPPSRE EMTKNQVSLT CLVKGFYPSD IAVEWESNGQ PENNYKTTPP  300
VLDSDGSFFL YSKLTVDKSR WQQGNVFSCS VMHEALHNHY TQKSLSLSPG K           351

SEQ ID NO: 107          moltype = AA  length = 351
FEATURE                 Location/Qualifiers
source                  1..351
                        mol_type = protein
                        organism = synthetic construct
SEQUENCE: 107
QLQLVESGGG LVQPGGSLRL SCAASGFTFS SYAMAWYRQR SGKERELVAS IDSSGYNTHY  60
TDAGKGRFTI SRDNAKNTVY LQMNNLKPED TAVYYCNAPN TGWGSRRYWG QGTQVTVSSE  120
PKSADKTHTC PPCPAPEAAG GPSVFLFPPK PKDTLMISRT PEVTCVVVDV SHEDPEVKFN  180
WYVDGVEVHN AKTKPREEQY NSTYRVVSVL TVLHQDWLNG KEYKCKVSNK ALPAPIEKTI  240
SKAKGQPREP QVYTLPPSRE EMTKNQVSLT CLVKGFYPSD IAVEWESNGQ PENNYKTTPP  300
VLDSDGSFFL YSKLTVDKSR WQQGNVFSCS VMHEALHNHY TQKSLSLSPG K           351

SEQ ID NO: 108          moltype = AA  length = 346
FEATURE                 Location/Qualifiers
source                  1..346
                        mol_type = protein
                        organism = synthetic construct
SEQUENCE: 108
QVQLVESGGG LVQPGESLRL SCSVSGNIGH IYDLGWYRQA SGKQRELVAS ITDNGRTIYG  60
DSVKGRFTIS RNNVKNTVNL QMNSLTPEDT AVYYCNLGHW LGYWGQGTQV TVSSEPKSAD  120
KTHTCPPCPA PEAAGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPGK                 346

SEQ ID NO: 109          moltype = AA  length = 352
FEATURE                 Location/Qualifiers
source                  1..352
                        mol_type = protein
```

```
                         organism = synthetic construct
SEQUENCE: 109
QVQLLESGGG LVQAGGSLRL SCAASGRTLS SYAMGWFRQA PGKGLEFVAS IGRSTYYADP  60
VKGRFTISRD NSKNTVYLQM NSLRAEDTAV YYCNAPIVAG FGTVVSGEYW GQGTLVTVSS  120
EPKSADKTHT CPPCPAPEAA GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 110           moltype = AA  length = 352
FEATURE                  Location/Qualifiers
source                   1..352
                         mol_type = protein
                         organism = synthetic construct
SEQUENCE: 110
QVQLLESGGG LVQPGGSLRL SCAASGRTLS SYAMGWFRQA PGKGLEFVAS IGRSTYYADP  60
VKGRFTISRD NSKNTVYLQM NSLRAEDTAV YYCNAPIVAG FGTVVSGEYW GQGTLVTVSS  120
EPKSADKTHT CPPCPAPEAA GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 111           moltype = AA  length = 352
FEATURE                  Location/Qualifiers
source                   1..352
                         mol_type = protein
                         organism = synthetic construct
SEQUENCE: 111
EVQLLESGGG LVQPGGSLRL SCAASGRTLS SYAMGWFRQA PGKGLEFVAS IGRSTYYADP  60
VKGRFTISRD NSKNTVYLQM NSLRAEDTAV YYCNAPIVAG FGTVVSGEYW GQGTLVTVSS  120
EPKSADKTHT CPPCPAPEAA GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 112           moltype = AA  length = 352
FEATURE                  Location/Qualifiers
source                   1..352
                         mol_type = protein
                         organism = synthetic construct
SEQUENCE: 112
QVQLLESGGG LVQPGGSLRL SCAASGRTLS SYAMGWFRQA PGKGLEFVAS IGRSTYYADS  60
VKGRFTISRD NSKNTVYLQM NSLRAEDTAV YYCNAPIVAG FGTVVSGEYW GQGTLVTVSS  120
EPKSADKTHT CPPCPAPEAA GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 113           moltype = AA  length = 352
FEATURE                  Location/Qualifiers
source                   1..352
                         mol_type = protein
                         organism = synthetic construct
SEQUENCE: 113
QVQLLESGGG LVQPGGSLRL SCAASGRTLS SYAMGWFRQA PGKGLEFVAS IGRSTYYADP  60
VKGRFTISRD NSKNTVYLQM NSLRAEDTAV YYCAAPIVAG FGTVVSGEYW GQGTLVTVSS  120
EPKSADKTHT CPPCPAPEAA GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 114           moltype = AA  length = 329
FEATURE                  Location/Qualifiers
source                   1..329
                         mol_type = protein
                         organism = synthetic construct
SEQUENCE: 114
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 115           moltype = AA  length = 585
FEATURE                  Location/Qualifiers
source                   1..585
                         mol_type = protein
                         organism = synthetic construct
```

-continued

```
SEQUENCE: 115
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARGQ VAILDYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGG GGGSGGGGSG GGGSEVQLLE SGGGLVQPGG  480
SLRLSCAASG RTLSSYAMGW FRQAPGKGLE FVASIGRSTY YADPVKGRFT ISRDNSKNTV  540
YLQMNSLRAE DTAVYYCNAP IVAGFGTVVS GEYWGQGTLV TVSSA                  585

SEQ ID NO: 116         moltype = AA  length = 590
FEATURE                Location/Qualifiers
source                 1..590
                       mol_type = protein
                       organism = synthetic construct
SEQUENCE: 116
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARGQ VAILDYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGG GGGSGGGGSG GGGSGGGGSE VQLLESGGGL  480
VQPGGSLRLS CAASGRTLSS YAMGWFRQAP GKGLEFVASI GRSTYYADPV KGRFTISRDN  540
SKNTVYLQMN SLRAEDTAVY YCNAPIVAGF GTVVSGEYWG QGTLVTVSSA             590

SEQ ID NO: 117         moltype = AA  length = 98
FEATURE                Location/Qualifiers
source                 1..98
                       mol_type = protein
                       organism = synthetic construct
SEQUENCE: 117
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKV                          98

SEQ ID NO: 118         moltype = AA  length = 232
FEATURE                Location/Qualifiers
source                 1..232
                       mol_type = protein
                       organism = synthetic construct
SEQUENCE: 118
EPKSCDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 119         moltype = AA  length = 231
FEATURE                Location/Qualifiers
source                 1..231
                       mol_type = protein
                       organism = synthetic construct
SEQUENCE: 119
EPKSCDKTHT CPPCPAPEAA GGPSVFLFPP KPKDTLYITR EPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP G           231
```

TL1A-BINDING MOLECULES, IL-23p19-BINDING MOLECULES, AND BISPECIFIC ANTIGEN-BINDING MOLECULES, AND USES THEREOF

CROSS-REFERENCE TO RELATED APPLICATIONS

The present application is based upon and claims the right of priority to CN Patent Application No. 2025100521083, filed Jan. 13, 2025, the disclosure of which is hereby incorporated by reference herein in its entirety for all purposes.

SEQUENCE LISTING

The instant application contains a Sequence Listing which has been submitted electronically in XML format and is hereby incorporated by reference in its entirety. Said XML copy, created on Feb. 27, 2025, is named CIE25S6002US-ST26.xml and is 120,044 bytes in size.

TECHNICAL FIELD

The application relates to the field of immunology. More specifically, the application relates to TL1A-binding molecules, IL-23p19-binding molecules, and bispecific antigen-binding molecules that simultaneously target TL1A and IL-23p19.

BACKGROUND

The occurrence of inflammatory and autoimmune diseases often involves abnormal activation of the immune system, leading to its attack on autologous tissues and induction of chronic inflammatory responses. An imbalance in the cytokine network is an important factor contributing to these diseases, with tumor necrosis factor-like ligand TA (TL1A) and interleukin-23 (IL-23) being key cytokines involved in immune regulation and inflammatory responses.

TL1A and its functional receptor DR3 (death receptor 3) are members of the TNF/TNFR protein superfamily. TL1A, also known as TNFSF15, is a type II transmembrane protein that can be present in a membrane-bound form (mTL1A) or be cleaved by matrix metalloproteinases and released as a soluble secreted form (sTL1A). TL1A is expressed on various cells, including antigen-presenting cells (such as dendritic cells and macrophages), lymphocytes, plasma cells, and fibroblasts, whereas the expression of DR3 is mainly restricted to activated lymphocytes. The binding of TL1A to DR3 may activate the TRADD pathway, which subsequently regulates TRAF2 and RIP1 to promote PI3K, MAPKs, and NF-κB, thereby exerting the pro-inflammatory effects. This process promotes the proliferation of lymphocytes, stimulates T cell polarization towards Th1 and Th17 cells, and induces the secretion of Th1, Th2, and Th17 cytokines. TL1A can also synergistically promote the production of IL-4, IL-12, and IL-23, and increase DR3 expression through Th1, Th2, and Th17 cells, thereby further enhancing inflammation. Additionally, TL1A can participate in apoptosis and necroptosis through the activation of the FADD, RIP3, and Caspase-8/3/7 pathways.

IL-23 is a heterodimeric cytokine composed of a unique p19 subunit (IL-23p19) and a p40 subunit shared with IL-12. IL-23 is mainly produced by activated dendritic cells and macrophages, and binds to the heterodimeric IL-23 receptor (composed of the IL-23R chain and the IL-12Rβ1 chain) to activate the JAK-STAT signaling pathway, thereby promoting the secretion of IL-17A and the proliferation and maintenance of Th17 cells, and enhancing Th17 cell-mediated inflammatory responses. IL-23 can also induce the generation of Th17 cells, thereby further exacerbating the inflammatory responses.

Research has demonstrated that TL1A and IL-23 can synergistically promote the Th17-mediated immune responses. After the differentiation of Th17 cells, TL1A/DR3 works in synergy with IL-23 to enhance the proliferative effect of IL-23 on Th17 cells and induces the production of IL-17A, thereby exacerbating the inflammatory responses.

Given the key roles of TLTA and IL-23 in pro-inflammatory pathways and their synergistic effects, simultaneous blockade of TL1A and IL-23 may be more effective in reducing the inflammatory responses than blocking either pathway alone. This strategy may provide a new therapeutic approach for the treatment of inflammatory and autoimmune diseases.

CONTENT OF THE DISCLOSURE

After in-depth research and creative work, the inventors identified monoclonal antibodies that can specifically bind to human TL1A and human IL-23p19 respectively through phage display and alpaca immunization. These antibodies can more effectively block the binding of human TL1A or human IL-23p19 to their receptors and inhibit their signaling pathways than anti-TL1A antibodies (such as Duvakitug, 1D1, and PRA-023) and anti-IL-23p19 antibodies (such as Risankizumab) in the prior art. Furthermore, based on the anti-TL1A antibodies and anti-IL-23p19 antibodies, the inventors constructed bispecific antibodies that simultaneously target human TL1A and human IL-23p19, which can more effectively inhibit or block the biological activities of TL1A and IL-23p19, thereby suppressing the inflammatory responses, compared to using anti-TL1A antibodies or anti-IL-23p19 antibodies alone. Therefore, the monoclonal and bispecific antibodies provided by the present disclosure have the potentials for the treatment, prevention, or alleviation of inflammatory diseases.

Therefore, in a first aspect, the present disclosure provides a tumor necrosis factor-like ligand 1A (TL1A)-binding molecule, which comprises at least one antigen-binding unit targeting TL1A comprising an immunoglobulin heavy chain variable domain (VH) and an immunoglobulin light chain variable domain (VL), wherein:

1) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 3, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 6;
2) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 11, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 13;

3) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 16, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 19;

4) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 22, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 23;

5) the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29;

6) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 32, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 33;

7) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 36, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 37; or 8) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 40, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 41.

In some embodiments, the VH comprises the amino acid sequence set forth in SEQ ID NO: 7, 14, 20, 24, 30, 34, 38 or 42, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 7, 14, 20, 24, 30, 34, 38 or 42.

In some embodiments, the VL comprises the amino acid sequence set forth in SEQ ID NO: 8, 15, 21, 25, 31, 35, 39 or 43, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 8, 15, 21, 25, 31, 35, 39 or 43.

In some embodiments, wherein:

1) the VH comprises the amino acid sequence set forth in SEQ ID NO: 7, and the VL comprises the amino acid sequence set forth in SEQ ID NO: 8;

2) the VH comprises the amino acid sequence set forth in SEQ ID NO: 14, and the VL comprises the amino acid sequence set forth in SEQ ID NO: 15;

3) the VH comprises the amino acid sequence set forth in SEQ ID NO: 20, and the VL comprises the amino acid sequence set forth in SEQ ID NO: 21;

4) the VH comprises the amino acid sequence set forth in SEQ ID NO: 24, and the VL comprises the amino acid sequence set forth in SEQ ID NO: 25;

5) the VH comprises the amino acid sequence set forth in SEQ ID NO: 30, and the VL comprises the amino acid sequence set forth in SEQ ID NO: 31;

6) the VH comprises the amino acid sequence set forth in SEQ ID NO: 34, and the VL comprises the amino acid sequence set forth in SEQ ID NO: 35;

7) the VH comprises the amino acid sequence set forth in SEQ ID NO: 38, and the VL comprises the amino acid sequence set forth in SEQ ID NO: 39; or 8) the VH comprises the amino acid sequence set forth in SEQ ID NO: 42, and the VL comprises the amino acid sequence set forth in SEQ ID NO: 43.

In some embodiments, the VH and/or the VL further comprise one or more substitutions, additions and/or deletions of amino acid residues and maintain the specific binding to TL1A, wherein the one or more substitutions, additions and/or deletions of amino acid residues occur in the sequences of the VH and/or the VL but not in the sequences of any CDR. In some embodiments, the TL1A-binding molecule is an anti-TL1A antibody or antigen-binding fragment thereof.

In some embodiments, the TL1A-binding molecule is a monoclonal antibody, a chimeric antibody, a humanized antibody or a fully human antibody, or antigen-binding fragments thereof.

In some embodiments, the TL1A-binding molecule is F(ab), F(ab'), $F(ab')_2$, scFab, Fd, Fv, dsFv, dAb, diabody or scFv.

In some embodiments, the TL1A-binding molecule further comprises an immunoglobulin heavy chain constant domain.

In some embodiments, the immunoglobulin heavy chain constant domain is a human immunoglobulin heavy chain constant domain, preferably a heavy chain constant domain derived from a human IgG, more preferably a heavy chain constant domain derived from a human IgG1 or IgG4.

In some embodiments, the immunoglobulin heavy chain constant domain further comprises one or more amino acid mutations selected from $L_{234}A$, $L_{235}A$, $M_{252}Y$, $S_{254}T$, $T_{256}E$ and $K_{447}del$.

In some embodiments, the immunoglobulin heavy chain constant domain sequence comprises the amino acid sequence set forth in SEQ ID NO: 80, 81 or 114, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 80, 81 or 114.

In some embodiments, the TL1A-binding molecule further comprises an immunoglobulin light chain constant domain.

In some embodiments, the immunoglobulin light chain constant domain is derived from a human λ light chain constant domain or a human κ light chain constant domain.

In some embodiments, the immunoglobulin light chain constant domain sequence comprises the amino acid sequence set forth in SEQ ID NO: 82, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 82.

In some embodiments, the TL1A-binding molecule comprises a plurality of antigen-binding units targeting TL1A.

In some embodiments, wherein the antigen-binding unit targeting TL1A comprises an immunoglobulin heavy chain, the heavy chain comprises the amino acid sequence set forth in SEQ ID NO: 83, 85, 87, 89, 91, 93, 95 or 97, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 83, 85, 87, 89, 91, 93, 95 or 97.

In some embodiments, wherein the antigen-binding unit targeting TL1A comprises an immunoglobulin light chain, the light chain comprises the amino acid sequence set forth in SEQ ID NO: 84, 86, 88, 90, 92, 94, 96 or 98, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 84, 86, 88, 90, 92, 94, 96 or 98.

In some embodiments, wherein the antigen-binding unit targeting TL1A comprises an immunoglobulin heavy chain and an immunoglobulin light chain, wherein:

1) the immunoglobulin heavy chain comprises the amino acid sequence set forth in SEQ ID NO: 83, and the immunoglobulin light chain comprises the amino acid sequence set forth in SEQ ID NO: 84;
2) the immunoglobulin heavy chain comprises the amino acid sequence set forth in SEQ ID NO: 85, and the immunoglobulin light chain comprises the amino acid sequence set forth in SEQ ID NO: 86;
3) the immunoglobulin heavy chain comprises the amino acid sequence set forth in SEQ ID NO: 87, and the immunoglobulin light chain comprises the amino acid sequence set forth in SEQ ID NO: 88;
4) the immunoglobulin heavy chain comprises the amino acid sequence set forth in SEQ ID NO: 89, and the immunoglobulin light chain comprises the amino acid sequence set forth in SEQ ID NO: 90;
5) the immunoglobulin heavy chain comprises the amino acid sequence set forth in SEQ ID NO: 91, and the immunoglobulin light chain comprises the amino acid sequence set forth in SEQ ID NO: 92;
6) the immunoglobulin heavy chain comprises the amino acid sequence set forth in SEQ ID NO: 93, and the immunoglobulin light chain comprises the amino acid sequence set forth in SEQ ID NO: 94;
7) the immunoglobulin heavy chain comprises the amino acid sequence set forth in SEQ ID NO: 95, and the immunoglobulin light chain comprises the amino acid sequence set forth in SEQ ID NO: 96; or
8) the immunoglobulin heavy chain comprises the amino acid sequence set forth in SEQ ID NO: 97, and the immunoglobulin light chain comprises the amino acid sequence set forth in SEQ ID NO: 98.

In a second aspect, the present disclosure provides an interleukin-23p19 subunit (IL-23p19)-binding molecule, which comprises at least one immunoglobulin single variable domain specifically binding to IL-23p19, the immunoglobulin single variable domain specifically binding to IL-23p19 comprises:

1) a CDR1 comprising the amino acid sequence set forth in SEQ ID NO: 44, a CDR2 comprising the amino acid sequence set forth in SEQ ID NO: 45, and a CDR3 comprising the amino acid sequence set forth in SEQ ID NO: 46;
2) a CDR1 comprising the amino acid sequence set forth in SEQ ID NO: 48, a CDR2 comprising the amino acid sequence set forth in SEQ ID NO: 49, and a CDR3 comprising the amino acid sequence set forth in SEQ ID NO: 50;
3) a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54;
4) a CDR1 comprising the amino acid sequence set forth in SEQ ID NO: 56, a CDR2 comprising the amino acid sequence set forth in SEQ ID NO: 57, and a CDR3 comprising the amino acid sequence set forth in SEQ ID NO: 58;
5) a CDR1 comprising the amino acid sequence set forth in SEQ ID NO: 60, a CDR2 comprising the amino acid sequence set forth in SEQ ID NO: 61, and a CDR3 comprising the amino acid sequence set forth in SEQ ID NO: 62;
6) a CDR1 comprising the amino acid sequence set forth in SEQ ID NO: 64, a CDR2 comprising the amino acid sequence set forth in SEQ ID NO: 65, and a CDR3 comprising the amino acid sequence set forth in SEQ ID NO: 62;
7) a CDR1 comprising the amino acid sequence set forth in SEQ ID NO: 67, a CDR2 comprising the amino acid sequence set forth in SEQ ID NO: 68, and a CDR3 comprising the amino acid sequence set forth in SEQ ID NO: 69; or
8) a CDR1 comprising the amino acid sequence set forth in SEQ ID NO: 71, a CDR2 comprising the amino acid sequence set forth in SEQ ID NO: 72, and a CDR3 comprising the amino acid sequence set forth in SEQ ID NO: 73.

In some embodiments, the immunoglobulin single variable domain specifically binding to IL-23p19 comprises the amino acid sequence set forth in SEQ ID NO: 47, 51, 55, 59, 63, 66, 70, 74, 75, 76, 77, 78 or 79, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 47, 51, 55, 59, 63, 66, 70, 74, 75, 76, 77, 78 or 79 and maintaining the specific binding to IL-23p19.

In some embodiments, the immunoglobulin single variable domain further comprises one or more substitutions, additions and/or deletions of amino acid residues and maintains the specific binding to IL-23p19, the one or more substitutions, additions and/or deletions of amino acid residues occur in the sequences of the immunoglobulin single variable domain but not in the sequences of any CDR.

In some embodiments, the immunoglobulin single variable domain is a VHH.

In some embodiments, the immunoglobulin single variable domain is a VHH derived from a camelid, and the camelid preferably is an alpaca or a llama.

In some embodiments, the immunoglobulin single variable domain is a humanized VHH.

In some embodiments, the IL-23p19-binding molecule is an anti-IL-23p19 antibody or an antigen-binding fragment thereof.

In some embodiments, the IL-23p19-binding molecule is a heavy chain antibody, a heavy chain single domain antibody, a chimeric antibody or a humanized antibody.

In some embodiments, the IL-23p19-binding molecule further comprises an immunoglobulin Fc domain.

In some embodiments, the immunoglobulin Fc domain is a human immunoglobulin Fc domain, preferably an Fc domain derived from a human IgG, more preferably an Fc domain derived from a human IgG1 or IgG4.

In some embodiments, the immunoglobulin Fc domain further comprises one or more amino acid mutations selected from $C_{220}A$, $L_{234}A$, $L_{235}A$, $M_{252}Y$, $S_{254}T$, $T_{256}E$ and $K_{447}del$.

In some embodiments, the immunoglobulin Fc domain comprises the amino acid sequence set forth in SEQ ID NO: 99, 100, 118 or 119, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 99, 100, 118 or 119.

In some embodiments, the immunoglobulin Fc domain is optionally connected to the immunoglobulin single variable domain via an immunoglobulin hinge region or a linker, preferably the linker is (GS)n, (GGS)n, (GGGS)n or (GGGGS)n, wherein n is 1, 2, 3, 4 or 5.

In some embodiments, the IL-23p19-binding molecule comprises a plurality of immunoglobulin single variable domains specifically binding to IL-23p19.

In some embodiments, the plurality of immunoglobulin single variable domains specifically binding to IL-23p19 are optionally connected via a linker, preferably the linker is (GS)n, (GGS)n, (GGGS)n or (GGGGS)n, wherein n is selected from 1, 2, 3, 4 or 5.

In some embodiments, the IL-23p19-binding molecule comprises the amino acid sequence set forth in any one of SEQ ID NOs: 101-113, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence of any one of SEQ ID NOs: 101-113, and maintaining the specific binding to IL-23p19.

In a third aspect, the present disclosure provides a multispecific antigen-binding molecule, which comprises the TL1A-binding molecule provided in the first aspect of the present disclosure and/or the IL-23p19-binding molecule provided in the second aspect of the present disclosure, and one or more additional antigen-binding functional regions, the one or more additional antigen-binding functional regions bind to different antigens or different epitopes of the same antigen from the TL1A-binding molecule and/or the IL-23p19-binding molecule.

In a fourth aspect, the present disclosure provides a bispecific antigen-binding molecule, which comprises the TL1A-binding molecule provided in the first aspect of the present disclosure and the IL-23p19-binding molecule provided in the second aspect of the present disclosure.

In some embodiments, the present disclosure provides a bispecific antigen-binding molecule, which comprises a first antigen-binding functional region and a second antigen-binding functional region, wherein the first antigen-binding functional region comprises at least one antigen-binding unit targeting TL1A comprising an immunoglobulin heavy chain variable domain (VH) and an immunoglobulin light chain variable domain (VL), wherein:

1) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 3, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 6;
2) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 11, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 13;
3) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 16, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 19;
4) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 22, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 23;

5) the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29;

6) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 32, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 33;

7) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 36, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 37; or 8) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 40, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 41;

and the second antigen-binding functional region comprises at least one immunoglobulin single variable domain specifically binding to IL-23p19 comprising:

1) a CDR1 comprising the amino acid sequence set forth in SEQ ID NO: 44, a CDR2 comprising the amino acid sequence set forth in SEQ ID NO: 45, and a CDR3 comprising the amino acid sequence set forth in SEQ ID NO: 46;

2) a CDR1 comprising the amino acid sequence set forth in SEQ ID NO: 48, a CDR2 comprising the amino acid sequence set forth in SEQ ID NO: 49, and a CDR3 comprising the amino acid sequence set forth in SEQ ID NO: 50;

3) a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54;

4) a CDR1 comprising the amino acid sequence set forth in SEQ ID NO: 56, a CDR2 comprising the amino acid sequence set forth in SEQ ID NO: 57, and a CDR3 comprising the amino acid sequence set forth in SEQ ID NO: 58;

5) a CDR1 comprising the amino acid sequence set forth in SEQ ID NO: 60, a CDR2 comprising the amino acid sequence set forth in SEQ ID NO: 61, and a CDR3 comprising the amino acid sequence set forth in SEQ ID NO: 62;

6) a CDR1 comprising the amino acid sequence set forth in SEQ ID NO: 64, a CDR2 comprising the amino acid sequence set forth in SEQ ID NO: 65, and a CDR3 comprising the amino acid sequence set forth in SEQ ID NO: 62;

7) a CDR1 comprising the amino acid sequence set forth in SEQ ID NO: 67, a CDR2 comprising the amino acid sequence set forth in SEQ ID NO: 68, and a CDR3 comprising the amino acid sequence set forth in SEQ ID NO: 69; or 8) a CDR1 comprising the amino acid sequence set forth in SEQ ID NO: 71, a CDR2 comprising the amino acid sequence set forth in SEQ ID NO: 72, and a CDR3 comprising the amino acid sequence set forth in SEQ ID NO: 73.

In some embodiments, the bispecific antigen-binding molecule comprises a first antigen-binding functional region and a second antigen-binding functional region, wherein the first antigen-binding functional region comprises at least one antigen-binding unit targeting TL1A comprising an immunoglobulin heavy chain variable domain (VH) and an immunoglobulin light chain variable domain (VL), wherein:

1) the VH comprises the amino acid sequence set forth in SEQ ID NO: 7, and the VL comprises the amino acid sequence set forth in SEQ ID NO: 8;

2) the VH comprises the amino acid sequence set forth in SEQ ID NO: 14, and the VL comprises the amino acid sequence set forth in SEQ ID NO: 15;

3) the VH comprises the amino acid sequence set forth in SEQ ID NO: 20, and the VL comprises the amino acid sequence set forth in SEQ ID NO: 21;

4) the VH comprises the amino acid sequence set forth in SEQ ID NO: 24, and the VL comprises the amino acid sequence set forth in SEQ ID NO: 25;

5) the VH comprises the amino acid sequence set forth in SEQ ID NO: 30, and the VL comprises the amino acid sequence set forth in SEQ ID NO: 31;

6) the VH comprises the amino acid sequence set forth in SEQ ID NO: 34, and the VL comprises the amino acid sequence set forth in SEQ ID NO: 35;

7) the VH comprises the amino acid sequence set forth in SEQ ID NO: 38, and the VL comprises the amino acid sequence set forth in SEQ ID NO: 39;

8) the VH comprises the amino acid sequence set forth in SEQ ID NO: 42, and the VL comprises the amino acid sequence set forth in SEQ ID NO: 43; or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the above-mentioned amino acid sequences, and maintains the specific binding to TL1A;

and the second antigen-binding functional region comprises at least one immunoglobulin single variable domain specifically binding to IL-23p19 comprising the amino acid sequence set forth in SEQ ID NO: 47, 51, 55, 59, 63, 66, 70, 74, 75, 76, 77, 78 or 79, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 47, 51, 55, 59, 63, 66, 70, 74, 75, 76, 77, 78 or 79, and maintaining the specific binding to IL-23p19.

In some embodiments, the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29.

In some embodiments, wherein the VH comprises the amino acid sequence set forth in SEQ ID NO: 30, and the VL comprises the amino acid sequence set forth in SEQ ID NO: 31, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 30 or 31, and maintaining the specific binding to TL1A.

In some embodiments, the immunoglobulin single variable domain comprises a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54.

In some embodiments, the immunoglobulin single variable domain comprises the amino acid sequence set forth in SEQ ID NO: 77, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 77, and maintaining the specific binding to IL-23p19.

In some embodiments, the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29; and the immunoglobulin single variable domain comprises a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54.

In some embodiments, the VH comprises the amino acid sequence set forth in SEQ ID NO: 30, and the VL comprises the amino acid sequence set forth in SEQ ID NO: 31, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 30 or 31, and maintaining the specific binding to TL1A; and the immunoglobulin single variable domain comprises the amino acid sequence set forth in SEQ ID NO: 77, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 77, and maintaining the specific binding to IL-23p19.

In some embodiments, the VH, the VL and/or the immunoglobulin single variable domain further comprise one or more substitutions, additions and/or deletions of amino acid residues and maintain the specific binding to TL1A and/or IL-23p19, and the one or more substitutions, additions and/or deletions of amino acid residues occur in the sequences of the VH, the VL and/or the immunoglobulin single variable domain but not in the sequences of any CDR.

In some embodiments, the immunoglobulin single variable domain further comprises one or more amino acid mutations that reduce immunogenicity.

In some embodiments, the immunoglobulin single variable domain is a VHH.

In some embodiments, the immunoglobulin single variable domain is a VHH derived from a camelid, the camelid preferably is an alpaca or a llama.

In some embodiments, the immunoglobulin single variable domain is a humanized VHH.

In some embodiments, the antigen-binding unit targeting TL1A is F(ab), F(ab'), $F(ab')_2$, scFab, Fd, Fv, dsFv, dAb, diabody or scFv.

In some embodiments, the antigen-binding unit targeting TL1A is F(ab), and the VH is connected to the immunoglobulin CH1 domain, and the VL is connected to the immunoglobulin light chain constant domain.

In some embodiments, the immunoglobulin CH1 domain is a human immunoglobulin CH1 domain, preferably a CH1 domain derived from a human IgG, more preferably a CH1 domain derived from a human IgG1 or IgG4; and/or, the immunoglobulin light chain constant domain is derived from a human λ light chain constant domain or a human κ light chain constant domain.

In some embodiments, the immunoglobulin CH1 domain sequence comprises the amino acid sequence set forth in SEQ ID NO: 117, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 117; and/or, the immunoglobulin light chain constant domain sequence comprises the amino acid sequence set forth in SEQ ID NO: 82, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 82.

In some embodiments, the bispecific antigen-binding molecule further comprises an immunoglobulin Fc domain.

In some embodiments, the immunoglobulin Fc domain is a human immunoglobulin Fc domain, preferably an Fc domain derived from a human IgG, more preferably an Fc domain derived from a human IgG1 or IgG4.

In some embodiments, the immunoglobulin Fc domain further comprises one or more amino acid mutations selected from $L_{234}A$, $L_{235}A$, $M_{252}Y$, $S_{254}T$, $T_{256}E$ and $K_{447}$del.

In some embodiments, the immunoglobulin Fc domain comprises the amino acid sequence set forth in SEQ ID NO: 99, 100, 118 or 119, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 99, 100, 118 or 119.

In some embodiments, the first antigen-binding functional region comprises a plurality of antigen-binding units targeting TL1A, and/or the second antigen-binding functional region comprises a plurality of immunoglobulin single variable domains specifically binding to IL-23p19.

In some embodiments, the numbers of the first antigen-binding functional region and the second antigen-binding functional region are each independently 1, 2 or more than 2.

In some embodiments, the plurality of antigen-binding units, the plurality of immunoglobulin single variable domains, and/or the plurality of antigen-binding functional regions are optionally connected via a linker, preferably the linker is (GS)n, (GGS)n, (GGGS)n or (GGGGS)n, wherein n is selected from 1, 2, 3, 4 or 5.

In some embodiments, the bispecific antigen-binding molecule comprises:

an immunoglobulin heavy chain, which comprises from the N-terminus to the C-terminus: the VH, the immunoglobulin CH1 domain, the Fc domain, an optional linker and the immunoglobulin single variable domain; and an immunoglobulin light chain, which comprises from the N-terminus to the C-terminus: the VL and the immunoglobulin light chain constant domain.

In some embodiments, the linker is (GS)n, (GGS)n, (GGGS)n or (GGGGS)n, wherein n is selected from 1, 2, 3, 4 or 5.

In some embodiments, the immunoglobulin heavy chain comprises the amino acid sequence set forth in SEQ ID NO: 115 or 116, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 115 or 116; and the immunoglobulin light chain comprises the amino acid sequence set forth in SEQ ID NO: 92, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 92.

In a fifth aspect, the present disclosure provides a fusion protein, which comprises the TLTA-binding molecule provided in the first aspect of the present disclosure, the IL-23p19-binding molecule provided in the second aspect of the present disclosure, the multispecific antigen-binding molecule provided in the third aspect of the present disclosure, and/or the bispecific antigen-binding molecule provided in the fourth aspect of the present disclosure, and a polypeptide or protein that is expressed in fusion therewith.

In a sixth aspect, the present disclosure provides a conjugate, which comprises the TL1A-binding molecule provided in the first aspect of the present disclosure, the IL-23p19-binding molecule provided in the second aspect of the present disclosure, the multispecific antigen-binding molecule provided in the third aspect of the present disclosure, the bispecific antigen-binding molecule provided in the fourth aspect of the present disclosure, and/or the fusion protein provided in the fifth aspect of the present disclosure, and a conjugate that is conjugated thereto.

In a seventh aspect, the present disclosure provides a nucleic acid molecule, which comprises a nucleotide sequence encoding the TL1A-binding molecule provided in the first aspect of the present disclosure, the IL-23p19-binding molecule provided in the second aspect of the present disclosure, the multispecific antigen-binding molecule provided in the third aspect of the present disclosure, the bispecific antigen-binding molecule provided in the fourth aspect of the present disclosure, and/or a nucleotide sequence of the fusion protein provided in the fifth aspect of the present disclosure.

In an eighth aspect, the present disclosure provides an expression vector, which comprises the nucleic acid molecule provided in the seventh aspect of the present disclosure operably linked to an expression regulatory element.

In a ninth aspect, the present disclosure provides a host cell, which comprises the nucleic acid molecule provided in the seventh aspect of the present disclosure and/or the expression vector provided in the eighth aspect of the present disclosure.

In a tenth aspect, the present disclosure provides a method for preparing the TL1A-binding molecule provided in the first aspect of the present disclosure, the IL-23p19-binding molecule provided in the second aspect of the present disclosure, the multispecific antigen-binding molecule provided in the third aspect of the present disclosure, the bispecific antigen-binding molecule provided in the fourth aspect of the present disclosure, and/or the fusion protein provided in the fifth aspect of the present disclosure, the method comprises:

culturing the host cell provided in the ninth aspect of the present disclosure under conditions suitable for expressing the vector provided in the eighth aspect of the present disclosure, and optionally separating and/or purifying the TL1A-binding molecule, the IL-23p19-binding molecule, the multispecific antigen-binding molecule, the bispecific antigen-binding molecule and/or the fusion protein from the host cell or the host cell culture.

In an eleventh aspect, the present disclosure provides a composition, which comprises the TLTA-binding molecule provided in the first aspect of the present disclosure, the IL-23p19-binding molecule provided in the second aspect of the present disclosure, the multispecific antigen-binding molecule provided in the third aspect of the present disclosure, the bispecific antigen-binding molecule provided in the fourth aspect of the present disclosure, the fusion protein provided in the fifth aspect of the present disclosure, and/or the conjugate provided in the sixth aspect of the present disclosure.

In some embodiments, the composition is a pharmaceutical composition, the pharmaceutical composition further comprises at least one pharmaceutically acceptable carrier and/or excipient, and optionally comprises one or more other pharmaceutically active therapeutic agents.

In a twelfth aspect, the present disclosure provides a use of the TL1A-binding molecule provided in the first aspect of the present disclosure, the IL-23p19-binding molecule provided in the second aspect of the present disclosure, the multispecific antigen-binding molecule provided in the third aspect of the present disclosure, the bispecific antigen-binding molecule provided in the fourth aspect of the present disclosure, the fusion protein provided in the fifth aspect of the present disclosure, the conjugate provided in the sixth aspect of the present disclosure, and/or the composition provided in the eleventh aspect of the present disclosure in the preparation of a medicament for treating, preventing or alleviating inflammatory diseases and/or autoimmune diseases.

In some embodiments, the inflammatory diseases and/or autoimmune diseases are selected from asthma, rheumatoid arthritis, multiple sclerosis, inflammatory bowel disease, systemic lupus erythematosus, ankylosing spondylitis or psoriasis.

In some embodiments, the inflammatory bowel disease is selected from Crohn's disease or ulcerative colitis.

In some embodiments, the medicament further comprises one or more other therapeutic agents for treating inflammatory diseases and/or autoimmune diseases.

In a thirteenth aspect, the present disclosure provides a method for treating, preventing or alleviating inflammatory diseases and/or autoimmune diseases, which comprises administering a therapeutically effective amount of the TL1A-binding molecule provided in the first aspect of the present disclosure, the IL-23p19-binding molecule provided in the second aspect of the present disclosure, the multispecific antigen-binding molecule provided in the third aspect of the present disclosure, the bispecific antigen-binding molecule provided in the fourth aspect of the present disclosure, the fusion protein provided in the fifth aspect of the present disclosure, the conjugate provided in the sixth aspect of the present disclosure, and/or the composition provided in the eleventh aspect of the present disclosure to a subject in need thereof.

In some embodiments, the inflammatory diseases and/or autoimmune diseases are selected from asthma, rheumatoid arthritis, multiple sclerosis, inflammatory bowel disease, systemic lupus erythematosus, ankylosing spondylitis or psoriasis.

In some embodiments, the inflammatory bowel disease is selected from Crohn's disease or ulcerative colitis.

In some embodiments, the method further comprises using in combination with one or more other therapeutic agents for treating inflammatory diseases and/or autoimmune diseases.

In a fourteenth aspect, the present disclosure provides a use of the TL1A-binding molecule provided in the first aspect of the present disclosure, the IL-23p19-binding molecule provided in the second aspect of the present disclosure, the multispecific antigen-binding molecule provided in the third aspect of the present disclosure, the bispecific antigen-binding molecule provided in the fourth aspect of the present disclosure, the fusion protein provided in the fifth aspect of the present disclosure, the conjugate provided in the sixth aspect of the present disclosure, and/or the composition provided in the eleventh aspect of the present disclosure in inhibiting or blocking TL1A and/or IL-23p19 signaling in vivo or in vitro.

DETAILED DESCRIPTION OF THE PREFERRED EMBODIMENT

Figure 1:
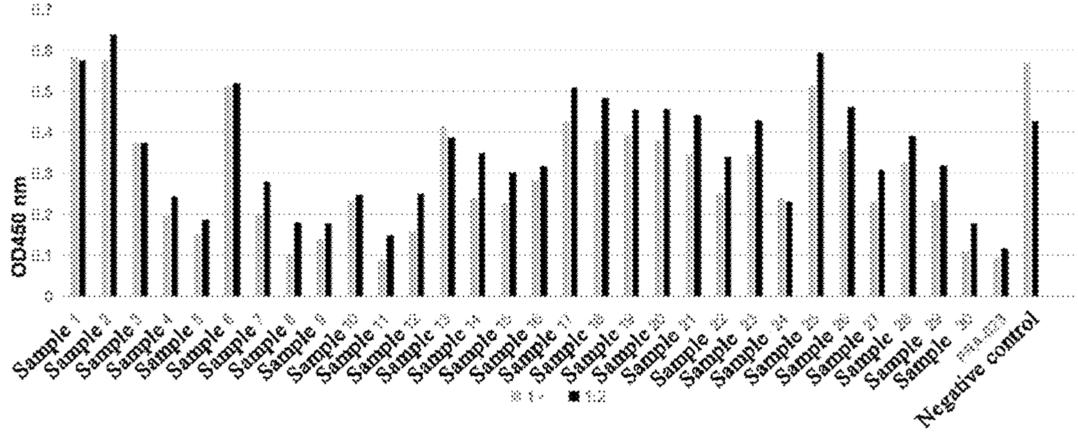
FIG. 1: Blocking assay of anti-TL1A-F(ab) crude extracts on the binding of human TL1A-DR3, wherein eight clones (clones 4, 5, 8, 9, 11, 12, 24, and 30) exhibit a significant blocking efficacy.

Although the present disclosure can be implemented in many different forms, the specific illustrative embodiments disclosed herein are intended to verify the principles of the present disclosure. It should be noted that the present disclosure is not limited to the specific embodiments illustrated. It would be obvious to those skilled in the art that various equivalent forms, modifications, or changes can be made without departing from the scope of the present disclosure as disclosed, and it should be understood that these equivalent embodiments are included herein. All references cited herein, including patent publications, patents, and patent applications, are incorporated herein by reference in their entirety. In addition, any section headings used herein are for organizational purposes only and are not to be interpreted as limiting the subject matter described.

Unless otherwise defined herein, scientific and technical terms used in conjunction with the present disclosure shall have the meanings that are commonly understood by those of ordinary skill in the art. Moreover, unless otherwise required in the context, terms in the singular shall include the plural, and vice versa. More specifically, as used in the specification and the appended claims, unless otherwise specified in the context, the singular forms "a," "an," and "the" include plural referents. In this application, unless otherwise stated, the use of "or" means "and/or." In this application, terms "first," "second," and the like have no substantive meaning and are used merely to distinguish identical terms. In addition, the use of the terms "comprising," "including," "containing," and the like is not restrictive. Furthermore, the ranges provided in the specification and the appended claims include the endpoints and all values between the endpoints. The term "about," when used in conjunction with numerical values, means a range of numerical values that are within 10% below and 10% above the specified numerical value.

Generally, the terms and techniques related to cell and tissue culture, molecular biology, immunology, microbiology, genetics, and protein and nucleic acid chemistry and hybridization described herein are well-known and commonly used terms in the art. Unless otherwise specified, the methods and techniques of the present disclosure are generally performed according to conventional methods known in the art and as described in the various general and more specific references cited and discussed throughout the specification. See, for example, Sambrook J. & Russell D., Molecular Cloning: A Laboratory Manual, 3rd ed., Cold Spring Harbor Laboratory Press, Cold Spring Harbor, N.Y. (2000); Abbas et al., Cellular and Molecular Immunology, 6th ed., W.B. Saunders Company (2010); Harlow and Lane, Using Antibodies: A Laboratory Manual, Cold Spring Harbor Laboratory Press, Cold Spring Harbor, N.Y. (1998); Ausubel et al., Short Protocols in Molecular Biology: A Compendium of Methods from Current Protocols in Molecular Biology, Wiley, John & Sons, Inc. (2002); and Coligan et al., Short Protocols in Protein Science, Wiley, John & Sons, Inc. (2003). The terms and laboratory procedures and techniques related to analytical chemistry, synthetic organic chemistry, and pharmaceutical and medicinal chemistry described herein are also well-known and commonly used terms in the art.

Definitions

To better understand the present disclosure, the definitions and explanations of relevant terms are provided as follows.

As used herein, the term "antigen-binding molecule" may encompass any molecule that specifically binds to a particular antigen. In some cases, "antigen-binding molecule" may encompass "antigen antagonist." "Antigen antagonist" refers to any compound or biomolecule that blocks the specific binding of a particular antigen to its natural receptor. Antigen-binding molecules or antigen antagonists can be antigen-binding proteins. "Antigen-binding protein" generally refers to a protein molecule that comprises an antigen-binding portion, and optionally a scaffold or framework portion that allows the antigen-binding portion to adopt a conformation that facilitates the binding of the antigen-binding molecule to the antigen. Antigen-binding proteins may typically include the antibody light chain variable domain (VL), the antibody heavy chain variable domain (VH), or both, and functional fragments thereof. The variable domains of the heavy and light chains contain the binding domains that interact with the antigen. In this disclosure, the term "antigen-binding molecule" also encompasses heavy chain single-domain antibodies and proteins containing immunoglobulin single variable domains. Examples of antigen-binding molecules include, but are not limited to, antibodies, antigen-binding fragments, heavy chain single-domain antibodies, immunoglobulin conjugates, multispecific antibodies (e.g., bispecific antibodies), antibody fragments, antibody derivatives, antibody analogs, or fusion proteins, etc., as long as they exhibit the desired antigen-binding activity.

As used herein, the term "antibody" or "immunoglobulin," whether referring to a heavy chain antibody or a conventional four-chain antibody herein, are used as general term to include full-length antibodies, their individual chains, and all parts, domains, or fragments thereof (including, but not limited to, antigen-binding domains or fragments, such as the VHH domain or the VH/VL domains, respectively). The conventional four-chain antibodies include glycoproteins of at least two heavy chains (H) and two light chains (L) interconnected by disulfide bonds, or antigen-binding fragments thereof. Each heavy chain consists of a heavy chain variable region (abbreviated as VH herein) and a heavy chain constant region. The heavy chain constant region is composed of three domains: CH1, CH2, and CH3. Each light chain consists of a light chain variable region (abbreviated as VL herein) and a light chain constant region. The light chain constant region is composed of a single domain, CL. In addition, the term "sequence" (such as in terms "immunoglobulin sequence," "antibody sequence," "single variable domain sequence," "VHH sequence," or "protein sequence," etc.) generally should be understood to comprise both the relevant amino acid sequence and the nucleic acid sequence or nucleotide sequence encoding said sequence, unless a more limited interpretation is required herein.

As used herein, the term "domain" (of a polypeptide or protein) refers to a folded protein structure that can maintain its tertiary structure independently of the rest of the protein. Generally, domains are responsible for a single functional property of a protein, and in many cases, domains can be added, removed, or transferred to other proteins without losing the function of the rest of the protein and/or the domain.

As used herein, the term "immunoglobulin domain" refers to a globular region of an antibody chain (e.g., the chain of a conventional four-chain antibody or the chain of a heavy chain antibody), or refers to a polypeptide that is essentially composed of such a globular region. Immunoglobulin domains are characterized by their maintenance of the immunoglobulin fold characteristic of the antibody molecule.

As used herein, the term "immunoglobulin variable domain" or "variable domain" refers to an immunoglobulin domain that is essentially composed of four "framework regions" known in the art and hereinafter as "Framework Region 1" or "FR1," "Framework Region 2" or "FR2," "Framework Region 3" or "FR3," and "Framework Region 4" or "FR4," wherein said framework regions are separated by three "complementarity-determining regions" or "CDRs" known in the art and hereinafter as "Complementarity-Determining Region 1" or "CDR1," "Complementarity-Determining Region 2" or "CDR2," and "Complementarity-Determining Region 3" or "CDR3." Thus, the general structure or sequence of an immunoglobulin variable domain can be represented as: FR1-CDR1-FR2-CDR2-FR3-CDR3-FR4. The amino acid sequences of FR1, FR2, FR3, and FR4 all constitute the "non-CDR regions" of the VH or VL described herein. The immunoglobulin variable domain is endowed with the specificity of the antibody against the antigen due to its antigen-binding site.

Methods for numbering the amino acid residues of VH and VL domains are known in the art, and these methods can also be similarly applied to VHH domains. For example, the Chothia numbering based on the three-dimensional structure of the antibody and the topology of the CDR loops (Chothia et al. (1989) Nature 342:877-883; Al-Lazikani et al., "Standard conformations for the canonical structures of immunoglobulins," Journal of Molecular Biology, 273, 927-948 (1997)), the Kabat numbering based on the variability of the antibody sequence (Kabat et al., Sequences of Proteins of Immunological Interest, 4th edition, U.S. Department of Health and Human Services, National Institutes of Health (1987)), the AbM numbering (University of Bath), the Contact numbering (University College London), the International ImMunoGeneTics database (IMGT numbering) (1999 Nucleic Acids Research, 27, 209-212), and the North numbering based on affinity propagation clustering using a large number of crystal structures. The variable domains and CDRs in antibody sequences can be identified according to the general rules developed in the art (as mentioned above, for example, the AbM numbering scheme) or by comparing the sequence with a database of known variable domains. The precise amino acid sequence boundaries of the CDRs of the variable domains of the antibodies provided by the disclosure can be determined by those skilled in the art according to any scheme in the art (for example, different numbering schemes or combinations).

It should be noted that the boundaries of the CDRs of the variable domains of the same antibody obtained based on different numbering schemes may vary. That is, the CDR sequences of the same antibody variable domain defined under different numbering schemes are different. Therefore, when involving the use of specific CDR sequences of antibodies defined by the disclosure, the scope of the antibody also encompasses such antibodies whose variable domain sequences contain the specific CDR sequences, but due to the application of different schemes (for example, different numbering schemes or combinations), the claimed CDR boundaries are different from the specific CDR boundaries defined by the disclosure. Unless otherwise stated, all CDR amino acid residues in immunoglobulin variable domains described herein are numbered and located according to the AbM numbering scheme.

Antibodies are classified based on the genetics of the constant region, also known as isotype. Human constant light chains are divided into κ (Cκ) and λ (Cλ) light chains. Heavy chains are divided into μ, δ, γ, α, or ε, and the antibody isotypes are defined as IgM, IgD, IgG, IgA, and IgE, respectively. Therefore, the term "isotype" used herein refers to any class and/or subclass of immunoglobulin defined by the chemical and antigenic characteristics of the constant region thereof. The known human immunoglobulin isotypes are IgG1 (IGHG1), IgG2 (IGHG2), IgG3 (IGHG3), IgG4 (IGHG4), IgAQ1 (IGHA1), IgA2 (IGHA2), IgM (IGHM), IgD (IGHD), and IgE (IGHE). The IgG class is the most commonly used human immunoglobulin isotype for therapeutic purposes. In humans, this class includes the subclasses IgG1, IgG2, IgG3, and IgG4.

As used herein, the term "chimeric antibody" includes antibodies whose variable region sequence is derived from one species and whose constant region sequence is derived from another species, for example, antibodies whose variable region sequence is derived from camelid antibodies and whose constant region sequence is derived from human antibodies.

As used herein, the term "Fab" includes a polypeptide containing the VH, CH1, VL, and CL immunoglobulin domains. Fab can refer to this region in isolation, or this region in the context of a full-length antibody or antibody fragment. Fab can include the F(ab) fragment produced by papain digestion of a whole antibody, F(ab') fragment produced by pepsin treatment of a whole antibody followed by reduction, or $F(ab')_2$ fragment produced by pepsin treatment of a whole antibody without reduction, where $F(ab')_2$ is a dimer of two F(ab') fragments connected by two disulfide bonds.

As used herein, the term "Fc" or "Fc domain" includes a polypeptide containing the constant region of the antibody heavy chain, excepting for the first constant immunoglobulin domain (CH1). Thus, Fc refers to the last two constant immunoglobulin domains of IgA, IgD, and IgG, the last three constant immunoglobulin domains of IgE and IgM, and the flexible hinge at the N-terminus of these domains. Fc can refer to this region in isolation, or this region in the context of an Fc polypeptide (e.g., an antibody).

As used herein, the term "hinge region" includes a flexible polypeptide comprising the amino acids between the first and second constant domains of the antibody. The "hinge region" described herein is a sequence region of 6-62 amino acids in length that is present only in IgA, IgD, and IgG, and encompasses the cysteine residues bridging the two heavy chains.

Unless otherwise stated, all human immunoglobulin heavy chain constant domains described herein are numbered according to the "EU numbering system" (Edelman G M et al., (1969) Proc Natl Acad Sci USA, 63(1): 78-85).

As used herein, the term "immunoglobulin single variable domain" or "single variable domain" refers to an immunoglobulin variable domain that can specifically bind to an antigenic epitope without pairing with another immunoglobulin variable domain. Typically, in conventional immunoglobulins, the heavy chain variable domain (VH) and the light chain variable domain (VL) interact to form the antigen-binding site. In contrast, an immunoglobulin single variable domain can specifically bind to an antigenic epitope without pairing with another immunoglobulin variable domain. Therefore, an example of the immunoglobulin single variable domain described herein is a "single-domain antibody," such as the immunoglobulin single variable domains VH and VL (VH and VL domains); another example of the immunoglobulin single variable domain is a "VHH domain" of camelids as defined below (or simply referred to as "VHH").

The "VHH domain," also known as heavy chain single-domain antibody, VHH, VHH antibody fragment, VHH antibody, or sdAb, is the variable domain of the antigen-binding immunoglobulin known as "heavy chain antibody (HCab)" (i.e., "antibody lacking light chains"). The term "VHH domain" is used to distinguish this variable domain from the heavy chain variable domain present in conventional four-chain antibodies (referred to herein as "VH domain") and the light chain variable domain present in conventional four-chain antibodies (referred to herein as "VL domain"). The VHH domain specifically binds to epitopes without the cooperation of other antigen-binding domains (which is in contrast to the VH or VL domains in conventional four-chain antibodies, wherein the epitope is recognized together with the VL domain and VH domain). The VHH domain is a small, stable, and efficient antigen recognition unit formed by a single immunoglobulin domain.

In the context of this disclosure, the terms "heavy chain single-domain antibody," "VHH domain," "VHH," "VHH antibody fragment," "VHH antibody," and "sdAb" are used interchangeably.

The VHH domain (which has been naturally "designed" to functionally bind to antigens in the absence of a light chain variable domain and without interacting with a light chain variable domain) can be used as a single, relatively small functional antigen-binding structural unit, domain, or polypeptide. This characteristic distinguishes the VHH domain from the VH and VL domains of conventional four-chain antibodies. These VH and VL domains themselves are generally not suitable for practical application as single antigen-binding proteins or immunoglobulin single variable domains and need to be combined in certain form or another form to provide a functional antigen-binding unit (e.g., in the form of conventional antibody fragments such as Fab fragments; or in the form of scFv composed of a VH domain covalently linked to a VL domain).

Due to these unique properties, the use of the VHH domain—alone or as a part of a larger polypeptide—provides many significant advantages over the use of conventional VH and VL domains, scFv, or conventional antibody fragments (e.g., F(ab) or $F(ab')_2$ fragments): only a single domain is required to bind antigens with a high affinity and a high selectivity, thus eliminating the need for the presence of two separate domains and the need to ensure that these two domains are in the proper spatial conformation and configuration (for example, scFv generally requires the use of a specially designed linker); the VHH domain can be expressed from a single gene and does not require post-translational folding or modification; the VHH domain can be easily engineered into multivalent and multispecific (formatting); the VHH domain is highly soluble and do not have a tendency to aggregate; the VHH domain is highly stable to heat, pH, proteases, and other denaturing agents or conditions, and therefore can be prepared, stored, or transported without the need for refrigeration equipment, thereby achieving cost, time, and environmental savings; the VHH domain is easy to prepare and relatively inexpensive, even on a scale required for production; the VHH domain is relatively small (approximately 15 kDa or one-tenth the size of a conventional IgG) than conventional four-chain antibodies and antigen-binding fragments thereof, thus showing a relatively higher tissue permeability and the ability to be administered at higher doses compared to conventional four-chain antibodies and antigen-binding fragments thereof; the VHH domain can exhibit so-called cavity-binding properties (especially due to its extended CDR3 loop compared to conventional VH domains), so that they can access targets and epitopes that are inaccessible to conventional four-chain antibodies and antigen-binding fragments thereof.

The heavy chain single-domain antibodies disclosed herein can be prepared by those skilled in the art according to known methods in the art or any future methods. Methods for obtaining VHH that binds to a specific antigen or epitope have previously been disclosed in, for example, the following documents: R. van der Linden et al., Journal of Immunological Methods, 240(2000)185-195; Li et al., J Biol Chem., 287(2012)13713-13721; Deffar et al., African Journal of Biotechnology, Vol. 8, (12), pp. 2645-2652, 17 Jun. 2009 and WO94/04678.

The present disclosure is not limited in terms of the origin of the immunoglobulin single variable domain sequence (or of the nucleotide sequence used to express it), nor in terms of the way in which the immunoglobulin single variable domain sequence or nucleotide sequence is (or has been) generated or obtained. The present disclosure can use immunoglobulin sequences from different origins, such as camelid immunoglobulin sequences. The present disclosure also includes fully human, humanized, or chimeric sequences. For example, the present disclosure includes camelid immunoglobulin sequences, humanized camelid immunoglobulin sequences, and chimeric sequences wherein the single variable domain sequence is derived from camelid immunoglobulin and the constant region sequence (e.g., the Fc domain) is derived from a human immunoglobulin. In addition, the present disclosure also uses fused immunoglobulin sequences to form, for example, multivalent and/or multispecific antigen-binding molecules; and immunoglobulin sequences containing labels or other functional portions (e.g., biologically active compounds or peptides, detectable labels, water-soluble polymers, etc.) derived from the immunoglobulin sequences of the present disclosure.

When the most effective animal-derived immunoglobulin is identified, its amino acid sequence can be optimized, for example, by affinity maturation or humanization.

The VHH domain derived from camelids can be "humanized" (also referred to herein as "sequence optimization") by replacing one or more amino acid residues in the original VHH sequence with one or more amino acid residues present at the corresponding positions in the VH domain of a human conventional four-chain antibody. In addition to humanization, "sequence optimization" can also encompass other modifications to the sequence that provide improved properties for the VHH, such as increased transient transfection expression yield. Humanization can prevent an immune response in humans to animal-derived VHH. The humanized VHH domain may contain one or more fully human framework region sequences. Humanization can be carried out in a manner known in the art, which is clear to those skilled in the art, for example, based on the further description herein and the prior art (e.g., WO2008/020079). In addition, it should be noted that such humanized VHH can be obtained in any suitable manner known in the art and is therefore not strictly limited to peptides obtained using naturally occurring VHH domains as starting materials.

As used herein, the term "full-length antibody" includes the structure that constructs the natural biological form of an antibody, including the variable and constant regions. For example, in most mammals, including humans and mice, the full-length antibody of the IgG class is a tetramer and is composed of two identical pairs of immunoglobulin chains, each pair having one light chain and one heavy chain. Each light chain comprises the immunoglobulin domains VL and CL, and each heavy chain comprises the immunoglobulin domains VH, CH1 (Cγ1), CH2 (Cγ2), and CH3 (Cγ3). In some camelids, such as llamas or alpacas, IgG antibodies can be composed of only two heavy chains, each heavy chain comprising an immunoglobulin single variable domain connected to the Fc region.

Those skilled in the art will understand that once the VH and VL domain sequences of an antibody are obtained, these domains can be further manipulated by conventional molecular biology means, for example, to reconstruct the VH and VL domains into antibody fragments with antigen-binding activities. Antibody fragments include, but are not limited to, Fab fragments composed of the VL, VH, CL, and CH1 domains, such as F(ab), F(ab'), $F(ab')_2$, and scFab connected via a peptide linker (e.g., a long flexible linker); Fd fragments composed of the VH and CH1 domains of a single antibody; Fv fragments composed of the VL and VH domains of a single antibody, such as disulfide bonds-stabilized Fv fragments (dsFv) connected via disulfide bonds and single-chain Fv fragments (scFv) connected via a peptide linker (e.g., a long flexible linker), wherein both variable domains can associate to form an antigen-binding site; diabodies formed by connecting the VH and VH domains of a single antibody via a short linker to produce two antigen-binding sites by dimerization (Holliger P et al., Proc. Natl.

Acad. Sci. USA (1993) 90: 6444-6448; EP 404,097; WO 93/11161); and dAb fragments composed of a single variable region.

As used herein, the term "specificity" refers to the non-random binding interaction between two molecules, such as a particular antigen and its natural receptor, and/or a particular antigen and an antigen-binding molecule (e.g., the immunoglobulin single variable domain, heavy chain single-domain antibody, TL1A-binding molecule, or IL-23p19-binding molecule of the present disclosure). The specificity can be determined based on the affinity and/or avidity of the antigen-binding molecule. The affinity, represented by the equilibrium dissociation constant ($K_D$) of the antigen and the antigen-binding molecule, is a measure of the strength of the binding between the epitope and the antigen-binding site on the antigen-binding molecule: the smaller the $K_D$ value, the stronger the binding strength between the epitope and the antigen-binding molecule (or, affinity can also be expressed as the association constant ($K_A$), which is $1/K_D$). As those skilled in the art will understand, depending on the specific antigen of interest, affinity can be measured in known ways. Avidity is a measure of the strength of the binding between an antigen-binding molecule (e.g., immunoglobulin, antibody, immunoglobulin single variable domain, or peptide containing the same) and the relevant antigen. Avidity is related to both the affinity between the antigen-binding site on the antigen-binding molecule and the relevant antigen, and the number of relevant binding sites present on the antigen-binding molecule.

As used herein, the ability to "block" refers to the ability of an antigen-binding molecule to inhibit the specific binding interaction between two molecules (e.g., a particular target antigen and its natural receptor) to any detectable extent. In some embodiments, an antigen-binding molecule that blocks the specific binding interaction between two molecules inhibits the binding interaction between the two molecules by at least 50%. In some embodiments, the inhibition can be greater than 60%, greater than 70%, greater than 80%, or greater than 90%.

As used herein, the term "TL1A" includes variants, isoforms, and species homologs of TL1A. Therefore, the TL1A-binding molecule of the present disclosure can bind to human TL1A and can cross-react with TL1A from species other than humans, such as *Macaca fascicularis*. The use of "TL1A" herein encompasses all known or yet-to-be-discovered alleles and polymorphic forms of TL1A, with human TL1A being preferred.

The "TL1A-binding molecule" involved in the present disclosure refers to any molecule that can specifically bind to thymic stromal lymphopoietin (TL1A) and block the binding interaction between TL1A and DR3. In some cases, the "TL1A-binding molecule" can comprise at least one antigen-binding domain that binds to TL1A and blocks the binding interaction between TL1A and DR3.

As used herein, the term "IL-23p19" includes variants, isoforms, and species homologs of IL-23p19. Therefore, the IL-23p19-binding molecule of the present disclosure can bind to human IL-23p19 and can cross-react with IL-23p19 from species other than humans, such as *Macaca fascicularis*. The use of "IL-23p19" herein encompasses all known or yet-to-be-discovered alleles and polymorphic forms of IL-23p19, with human IL-23p19 being preferred.

The "IL-23p19-binding molecule" involved in the present disclosure refers to any molecule that can specifically bind to interleukin-23 (IL-23p19) and block the binding interaction between IL-23p19 and IL-23R and/or IL-12Rβ1. In some cases, the "IL-23p19-binding molecule" can comprise at least one antigen-binding domain that binds to IL-23p19 and blocks the binding interaction between IL-23p19 and IL-23R and/or IL-12Rβ1, such as the immunoglobulin single variable domain defined herein, such as VHH.

In some embodiments, the "TL1A-binding molecule" or "IL-23p19-binding molecule" of the present disclosure can independently contain 2, 3, 4, or more antigen-binding domains targeting the antigen.

As used herein, the term "valency" refers to the presence of a specified number of antigen-binding sites in a given molecule. The term "monovalent" refers to an antigen-binding molecule that has only a single antigen-binding site; and the term "multivalent" refers to an antigen-binding molecule that has multiple antigen-binding sites. Accordingly, the terms "bivalent," "tetravalent," and "hexavalent" respectively indicate the presence of 2, 4, and 6 binding sites in the antigen-binding molecule. In some embodiments, the TL1A-binding molecule or IL-23p19-binding molecule provided herein is bivalent.

In some embodiments, the "TL1A-binding molecule" or "IL-23p19-binding molecule" of the present disclosure also encompasses multispecific antigen-binding molecules, which comprise at least one antigen-binding domain that specifically binds to TL1A and blocks the binding interaction between TL1A and DR3, and/or at least one immunoglobulin single variable domain that specifically binds to IL-23p19 and blocks the binding interaction between IL-23p19 and IL-23R and/or IL-12Rβ1, and further comprise antigen-binding domains that bind to different antigens or different regions of the same antigen (e.g., different epitopes).

In some embodiments, the present disclosure also encompasses "TL1A/IL-23p19 bispecific antigen-binding molecules," which comprise at least one immunoglobulin single variable domain that specifically binds to TL1A and blocks the binding interaction between TL1A and DR3, and at least one immunoglobulin single variable domain that specifically binds to IL-23p19 and blocks the binding interaction between IL-23p19 and IL-23R and/or IL-12Rβ1.

In addition to the immunoglobulin single variable domains that bind to targeted antigens, the "TL1A-binding molecule," "IL-23p19-binding molecule," and/or "TL1A/IL-23p19 bispecific antigen-binding molecule" of the present disclosure may also comprise linkers and/or functional portions, such as biologically active compounds or peptides (e.g., Fc domain) and/or conjugates that can modulate (e.g., increase or decrease) the natural activity of the antigen-binding molecule or confer novel activity on the molecule.

As used herein, the term "isolated" generally refers to a biological material (e.g., a virus, nucleic acid, or protein) that is substantially free of components that normally accompany or interact with it in its naturally occurring environment. The isolated biological material may optionally contain additional materials that are not found in its natural environment (e.g., nucleic acids or proteins). Herein, when referring to proteins, "isolated" generally means that the molecule is separated and isolated from the whole organism in which the molecule naturally exists, or that it is essentially free of other biological macromolecules of the same type. When referring to nucleic acid molecules, it is completely or partially separated from the sequences with which it is naturally associated, or the nucleic acid has heterologous sequences associated with it, or the nucleic acid is separated from the chromosome.

As used herein, the terms "polypeptide" and "protein" are used interchangeably and generally refer to a polymer of amino acid residues. The term also applies to amino acid polymers in which one or more amino acid residues are analogs or mimetics of the corresponding naturally occurring amino acids, as well as naturally occurring amino acid polymers. The term also includes modified amino acid polymers, for example, by adding glycosyl residues to form glycoproteins or by phosphorylation modification. Polypeptides and proteins can be produced by naturally occurring and non-recombinant cells or by genetically engineered or recombinant cells, and can comprise molecules with the amino acid sequence of a natural protein, or molecules with one or more amino acids deleted, added, and/or substituted from the natural sequence. The terms "polypeptide" and "protein" particularly include sequences in which one or more amino acids in the antigen-binding protein described in the present disclosure are deleted, added, and/or substituted.

Amino acid residues will be represented according to the standard three-letter or one-letter amino acid codes known and agreed upon in the art. When comparing two amino acid sequences, the term "amino acid difference" refers to the insertion, deletion, or substitution of a specified number of amino acid residues at a particular position in the reference sequence compared to another sequence. In the case of substitution, the substitution will preferably be a conservative amino acid substitution, which refers to the replacement of an amino acid residue with another amino acid residue of similar chemical structure, which has little or essentially no effect on the function, activity, or other biological properties of the polypeptide. Conservative amino acid substitutions are well known in the art, for example, conservative amino acid substitutions are preferably one amino acid within groups (i) to (v) being replaced by another amino acid within the same group: (i) small aliphatic non-polar or weakly polar residues: Ala, Ser, Thr, Pro, and Gly; (ii) polar negatively charged residues and their (uncharged) amides: Asp, Asn, Glu, and Gln; (iii) polar positively charged residues: His, Arg, and Lys; (iv) larger aliphatic non-polar residues: Met, Leu, Ile, Val, and Cys; and (v) aromatic residues: Phe, Tyr, and Trp. Particularly preferred conservative amino acid substitutions are as follows: Ala substituted by Gly or Ser; Arg substituted by Lys; Asn substituted by Gln or His; Asp substituted by Glu; Cys substituted by Ser; Gln substituted by Asn; Glu substituted by Asp; Gly substituted by Ala or Pro; His substituted by Asn or Gln; Ile substituted by Leu or Val; Leu substituted by Ile or Val; Lys substituted by Arg, Gln, or Glu; Met substituted by Leu, Tyr, or Ile; Phe substituted by Met, Leu, or Tyr; Ser substituted by Thr; Thr substituted by Ser; Trp substituted by Tyr; Tyr substituted by Trp or Phe; or Val substituted by Ile or Leu.

"Sequence identity" between two polypeptide sequences indicates the percentage of identical amino acids between the sequences. "Sequence similarity" indicates the percentage of amino acids that are identical or represent conserved amino acid substitutions. Methods for evaluating the degree of sequence identity between amino acids or nucleotides are known to those skilled in the art. For example, amino acid sequence identity is usually measured using sequence analysis software. For example, the BLAST program in the NCBI database can be used to determine identity. For the determination of sequence identity, see, for example: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987 and Sequence Analysis Primer, Gribskov, M. and Devereux, J., eds., M Stockton Press, New York, 1991.

As used herein, the term "$EC_{50}$," also known as "half-maximum effective concentration," refers to the concentration of a drug, an antibody, or a toxic agent that induces a response of 50% between the baseline and the maximum after a specific exposure time. In the context of the application, the unit of $EC_{50}$ is "μg/mL."

As used herein, the term "operably linked" generally means that at least one nucleic acid molecule and at least one regulatory element are in a functional relationship with each other. For example, if a promoter can initiate or otherwise control/regulate the transcription and/or expression of a coding sequence, the promoter is considered to be "operably linked" to the coding sequence (where the coding sequence should be understood to be "under the control" of the promoter). Typically, when two nucleotide sequences are operably linked, they will be in the same orientation and usually also in the same reading frame. They are also generally substantially contiguous.

As used herein, the term "subject" includes any animal, and more specifically, mammals. Among mammals, humans and non-human mammals can be distinguished. Non-human animals can be, for example, companion animals (e.g., dogs, cats, etc.), livestock (e.g., cattle, pigs, horses, sheep, goats, etc.), and experimental animals commonly used for research purposes and/or for the production of antibodies (e.g., rats, mice, guinea pigs, non-human primates (such as *Macaca fascicularis*), or camelids, etc.). In the context of prophylactic and/or therapeutic purposes, the subject is preferably a human.

As used herein, the terms "prevent," "preventing," and "prevention" refer to the method of preventing or delaying the occurrence of a disease or condition or symptom (e.g., inflammatory disease) in a subject. The terms "treat," "treating," and "treatment" refer to obtaining the desired pharmacological and/or physiological effect. The effect can be prophylactic in terms of completely or partially preventing the disease or its symptoms, and/or therapeutic in terms of partially or completely curing the disease and/or adverse effects caused by the disease. The "treatment" used herein encompasses diseases in mammals, particularly humans, and includes: (a) preventing the occurrence of a disease or condition in an individual who is susceptible to the disease but has not yet been diagnosed with the disease; (b) inhibiting the disease, such as arresting the progression of the disease; or (c) alleviating the disease, such as alleviating the symptoms associated with the disease. The "treatment" used herein includes the administration of drugs or compounds to individuals to treat, cure, alleviate, improve, mitigate, or inhibit the disease of the individual, including but not limited to administering drugs containing the compounds described herein to individuals in need.

As used herein, the term "effective amount" refers to the amount sufficient to achieve or at least partially achieve the desired effect. For example, an effective amount for preventing disease refers to the amount sufficient to prevent, stop, or delay the occurrence of the disease; an effective amount for treating disease refers to the amount sufficient to cure or at least partially prevent the disease and its complications in patients who already affected with the disease. Determining such an effective amount is well within the capabilities of those skilled in the art. For example, the effective amount for therapeutic use will depend on the severity of the disease to be treated, the overall state of the patient's own immune system, the patient's general condition such as age, weight, and gender, the route of administration of the drug, and other treatments administered concurrently, etc.

As used herein, the term "pharmaceutical composition" can be used for the treatment of disease, as well as in vitro cell culture experiments. When used for the treatment of disease, the term "pharmaceutical composition" usually refers to a unit dose form and can be prepared by any of the well-known methods in the pharmaceutical field. All methods include the step of combining the active ingredient with excipients that constitute one or more auxiliary components. Typically, the composition is prepared by uniformly and thoroughly combining the active compound with liquid excipients, finely divided solid excipients, or both.

The present disclosure aims to provide novel drugs for the treatment, prevention, or alleviation of inflammatory diseases and/or autoimmune diseases (such as inflammatory bowel disease, typically including Crohn's disease and ulcerative colitis).

In some embodiments, the present disclosure relates to TL1A-binding molecules, IL-23p19-binding molecules, and bispecific antigen-binding molecules targeting both TL1A and IL-23p19. The TL1A-binding molecules and IL-23p19-binding molecules can more effectively block the binding of human TL1A or human IL-23p19 with their receptors and inhibit their signaling than anti-TL1A antibodies (such as Duvakitug, 1D1, and PRA-023) and anti-IL-23p19 antibodies (such as Risankizumab) in the prior art. The bispecific antigen-binding molecules can more effectively inhibit or block the biological activities of TL1A and IL-23p19, and inhibit inflammatory responses, compared with the use of TL1A antibodies or IL-23p19 antibodies alone.

TL1A-Binding Molecules

The TL1A-binding molecules provided by the present disclosure can more effectively block the binding of both membrane-bound and secreted human TL1A with DR3 than anti-TL1A antibodies in the prior art (such as Duvakitug, 1D1, and PRA-023), thereby providing biological activity, including, for example, inhibiting the production of inflammatory cytokines and thus alleviating inflammatory responses. Moreover, the TL1A-binding molecules provided by the present disclosure do not completely block the binding of human TL1A with DcR3 that negatively regulates the TL1A-DR3 signaling pathway, and thus are expected to have superior clinical development potential.

Therefore, in some aspects, the present disclosure provides a TL1A-binding molecule, which comprises at least one antigen-binding unit targeting TL1A, the antigen-binding unit targeting TL1A comprises an immunoglobulin heavy chain variable domain (VH) and an immunoglobulin light chain variable domain (VL).

In some embodiments, the at least one antigen-binding unit targeting TL1A may comprise an HCDR1, an HCDR2, and an HCDR3 in the VH as shown in SEQ ID NO: 7, 14, 20, 24, 30, 34, 38, or 42, and an LCDR1, an LCDR2, and an LCDR3 in the VL as shown in SEQ ID NO: 8, 15, 21, 25, 31, 35, 39, or 43, wherein the CDRs may be defined according to any of the following definition systems: Kabat CDR, AbM CDR, Chothia CDR, or IMGT CDR.

In some embodiments, the at least one antigen-binding unit targeting TL1A may comprise:

1) an HCDR1, an HCDR2, and an HCDR3 in the VH as shown in SEQ ID NO: 7, and an LCDR1, an LCDR2, and an LCDR3 in the VL as shown in SEQ ID NO: 8;
2) an HCDR1, an HCDR2, and an HCDR3 in the VH as shown in SEQ ID NO: 14, and an LCDR1, an LCDR2, and an LCDR3 in the VL as shown in SEQ ID NO: 15;
3) an HCDR1, an HCDR2, and an HCDR3 in the VH as shown in SEQ ID NO: 20, and an LCDR1, an LCDR2, and an LCDR3 in the VL as shown in SEQ ID NO: 21;
4) an HCDR1, an HCDR2, and an HCDR3 in the VH as shown in SEQ ID NO: 24, and an LCDR1, an LCDR2, and an LCDR3 in the VL as shown in SEQ ID NO: 25;
5) an HCDR1, an HCDR2, and an HCDR3 in the VH as shown in SEQ ID NO: 30, and an LCDR1, an LCDR2, and an LCDR3 in the VL as shown in SEQ ID NO: 31;
6) an HCDR1, an HCDR2, and an HCDR3 in the VH as shown in SEQ ID NO: 34, and an LCDR1, an LCDR2, and an LCDR3 in the VL as shown in SEQ ID NO: 35;
7) an HCDR1, an HCDR2, and an HCDR3 in the VH as shown in SEQ ID NO: 38, and an LCDR1, an LCDR2, and an LCDR3 in the VL as shown in SEQ ID NO: 39; or
8) an HCDR1, an HCDR2, and an HCDR3 in the VH as shown in SEQ ID NO: 42, and an LCDR1, an LCDR2, and an LCDR3 in the VL as shown in SEQ ID NO: 43;

wherein the CDRs may be defined according to any of the following definition systems: Kabat CDR, AbM CDR, Chothia CDR, or IMGT CDR.

In some embodiments, the immunoglobulin heavy chain variable domain (VH) and the immunoglobulin light chain variable domain (VL) comprise CDR1, CDR2, and CDR3 selected from any one or more of the following groups defined according to the AbM numbering system:

1) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 3, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 6;
2) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 11, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 13;
3) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 16, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 19;
4) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 22, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 23;

5) the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29;

6) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 32, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 33;

7) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 36, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 37; or 8) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 40, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 41.

In some preferred embodiments, the at least one antigen-binding unit targeting TL1A may comprise:

1) an HCDR1, an HCDR2, and an HCDR3 in the VH as shown in SEQ ID NO: 20, and an LCDR1, an LCDR2, and an LCDR3 in the VL as shown in SEQ ID NO: 21; or 2) an HCDR1, an HCDR2, and an HCDR3 in the VH as shown in SEQ ID NO: 30, and an LCDR1, an LCDR2, and an LCDR3 in the VL as shown in SEQ ID NO: 31;

wherein the CDRs may be defined according to any of the following definition systems: Kabat CDR, AbM CDR, Chothia CDR, or IMGT CDR.

In some preferred embodiments, the immunoglobulin heavy chain variable domain (VH) and the immunoglobulin light chain variable domain (VL) comprise a CDR1, a CDR2, and a CDR3 selected from any one or more of the following groups defined according to the AbM numbering system:

1) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 16, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 19; or 2) the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29.

In some embodiments, the TL1A-binding molecule provided by the present disclosure comprises an immunoglobulin heavy chain variable domain, wherein the VH comprises the amino acid sequence set forth in SEQ ID NO: 7, 14, 20, 24, 30, 34, 38, or 42, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 7, 14, 20, 24, 30, 34, 38, or 42.

In some embodiments, the TL1A-binding molecule provided by the present disclosure comprises an immunoglobulin heavy chain variable domain, wherein the VH comprises the amino acid sequence set forth in SEQ ID NO: 20 or 30, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 20 or 30.

In some embodiments, the TL1A-binding molecule provided by the present disclosure comprises an immunoglobulin light chain variable domain, wherein the VL comprises the amino acid sequence set forth in SEQ ID NO: 8, 15, 21, 25, 31, 35, 39, or 43, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 8, 15, 21, 25, 31, 35, 39, or 43.

In some preferred embodiments, the TL1A-binding molecule provided by the present disclosure comprises an immunoglobulin light chain variable domain, wherein the VL comprises the amino acid sequence set forth in SEQ ID NO: 21 or 31, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 21 or 31.

In some embodiments, the TL1A-binding molecule provided by the present disclosure comprises an immunoglobulin heavy chain variable domain (VH) and an immunoglobulin light chain variable domain (VL), wherein:

1) the VH comprises the amino acid sequence set forth in SEQ ID NO: 7, and the VL comprises the amino acid sequence set forth in SEQ ID NO: 8;

2) the VH comprises the amino acid sequence set forth in SEQ ID NO: 14, and the VL comprises the amino acid sequence set forth in SEQ ID NO: 15;
3) the VH comprises the amino acid sequence set forth in SEQ ID NO: 20, and the VL comprises the amino acid sequence set forth in SEQ ID NO: 21;
4) the VH comprises the amino acid sequence set forth in SEQ ID NO: 24, and the VL comprises the amino acid sequence set forth in SEQ ID NO: 25;
5) the VH comprises the amino acid sequence set forth in SEQ ID NO: 30, and the VL comprises the amino acid sequence set forth in SEQ ID NO: 31;
6) the VH comprises the amino acid sequence set forth in SEQ ID NO: 34, and the VL comprises the amino acid sequence set forth in SEQ ID NO: 35;
7) the VH comprises the amino acid sequence set forth in SEQ ID NO: 38, and the VL comprises the amino acid sequence set forth in SEQ ID NO: 39; or
8) the VH comprises the amino acid sequence set forth in SEQ ID NO: 42, and the VL comprises the amino acid sequence set forth in SEQ ID NO: 43.

In some preferred embodiments, the TL1A-binding molecule provided by the present disclosure comprises an immunoglobulin heavy chain variable domain (VH) and an immunoglobulin light chain variable domain (VL), wherein:
1) the VH comprises the amino acid sequence set forth in SEQ ID NO: 20, and the VL comprises the amino acid sequence set forth in SEQ ID NO: 21; or
2) the VH comprises the amino acid sequence set forth in SEQ ID NO: 30, and the VL comprises the amino acid sequence set forth in SEQ ID NO: 31.

In some embodiments, the TL1A-binding molecule is an anti-TL1A antibody or antigen-binding fragment thereof.

In some embodiments, the TL1A-binding molecule is a monoclonal antibody, a chimeric antibody, a humanized antibody or a fully human antibody, or antigen-binding fragments thereof.

In some embodiments, the TL1A-binding molecule is F(ab), F(ab'), $F(ab')_2$, scFab, Fd, Fv, dsFv, dAb, diabody or scFv.

IL-23p19-Binding Molecule

The IL-23p19-binding molecule provided by the present disclosure can more effectively block the binding of human IL-23p19 to the complex of IL-23R and IL-12Rβ1 than the anti-IL-23p19 antibodies in the prior art (e.g., Risankizumab), thereby providing biological activity, including, for example, inhibiting the production of inflammatory cytokines, thus alleviating the inflammatory response.

Therefore, in some aspects, the present disclosure provides an IL-23p19-binding molecule, which comprises at least one immunoglobulin single variable domain that specifically binds to IL-23p19.

In some embodiments, the at least one immunoglobulin single variable domain that specifically binds to IL-23p19 may comprise a CDR1, a CDR2, and a CDR3 in the VHH as shown in SEQ ID NO: 47, 51, 55, 59, 63, 66, 70, or 74. The CDRs may be defined according to any of the following definition systems: Kabat CDR, AbM CDR, Chothia CDR, or IMGT CDR.

In some embodiments, the at least one immunoglobulin single variable domain that specifically binds to IL-23p19 comprises a CDR1, a CDR2, and a CDR3 selected from any one or more of the following groups defined according to the AbM numbering system:
1) a CDR1 comprising the amino acid sequence set forth in SEQ ID NO: 44, a CDR2 comprising the amino acid sequence set forth in SEQ ID NO: 45, and a CDR3 comprising the amino acid sequence set forth in SEQ ID NO: 46;
2) a CDR1 comprising the amino acid sequence set forth in SEQ ID NO: 48, a CDR2 comprising the amino acid sequence set forth in SEQ ID NO: 49, and a CDR3 comprising the amino acid sequence set forth in SEQ ID NO: 50;
3) a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54;
4) a CDR1 comprising the amino acid sequence set forth in SEQ ID NO: 56, a CDR2 comprising the amino acid sequence set forth in SEQ ID NO: 57, and a CDR3 comprising the amino acid sequence set forth in SEQ ID NO: 58;
5) a CDR1 comprising the amino acid sequence set forth in SEQ ID NO: 60, a CDR2 comprising the amino acid sequence set forth in SEQ ID NO: 61, and a CDR3 comprising the amino acid sequence set forth in SEQ ID NO: 62;
6) a CDR1 comprising the amino acid sequence set forth in SEQ ID NO: 64, a CDR2 comprising the amino acid sequence set forth in SEQ ID NO: 65, and a CDR3 comprising the amino acid sequence set forth in SEQ ID NO: 62;
7) a CDR1 comprising the amino acid sequence set forth in SEQ ID NO: 67, a CDR2 comprising the amino acid sequence set forth in SEQ ID NO: 68, and a CDR3 comprising the amino acid sequence set forth in SEQ ID NO: 69; or
8) a CDR1 comprising the amino acid sequence set forth in SEQ ID NO: 71, a CDR2 comprising the amino acid sequence set forth in SEQ ID NO: 72, and a CDR3 comprising the amino acid sequence set forth in SEQ ID NO: 73.

In some embodiments, the at least one immunoglobulin single variable domain that specifically binds to IL-23p19 may comprise the amino acid sequence set forth in SEQ ID NO: 47, 51, 55, 59, 63, 66, 70, or 74, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 47, 51, 55, 59, 63, 66, 70, or 74, and maintaining the specific binding to IL-23p19.

In some preferred embodiments, the at least one immunoglobulin single variable domain that specifically binds to IL-23p19 may comprise a CDR1, a CDR2, and a CDR3 in the VHH as shown in SEQ ID NO: 47, 55, 63, 66, or 70. The CDRs may be defined according to any of the following definition systems: Kabat CDR, AbM CDR, Chothia CDR, or IMGT CDR.

In some preferred embodiments, the at least one immunoglobulin single variable domain that specifically binds to IL-23p19 comprises a CDR1, a CDR2, and a CDR3 selected from any one or more of the following groups defined according to the AbM numbering system:
1) a CDR1 comprising the amino acid sequence set forth in SEQ ID NO: 44, a CDR2 comprising the amino acid sequence set forth in SEQ ID NO: 45, and a CDR3 comprising the amino acid sequence set forth in SEQ ID NO: 46;

2) a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54;
3) a CDR1 comprising the amino acid sequence set forth in SEQ ID NO: 60, a CDR2 comprising the amino acid sequence set forth in SEQ ID NO: 61, and a CDR3 comprising the amino acid sequence set forth in SEQ ID NO: 62;
4) a CDR1 comprising the amino acid sequence set forth in SEQ ID NO: 64, a CDR2 comprising the amino acid sequence set forth in SEQ ID NO: 65, and a CDR3 comprising the amino acid sequence set forth in SEQ ID NO: 62; or
5) a CDR1 comprising the amino acid sequence set forth in SEQ ID NO: 67, a CDR2 comprising the amino acid sequence set forth in SEQ ID NO: 68, and a CDR3 comprising the amino acid sequence set forth in SEQ ID NO: 69.

In some preferred embodiments, the at least one immunoglobulin single variable domain that specifically binds to IL-23p19 comprises the amino acid sequence set forth in SEQ ID NO: 47, 55, 63, 66, or 70, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 47, 55, 63, 66, or 70 and maintaining the specific binding to IL-23p19.

In some embodiments, the immunoglobulin single variable domain that specifically binds to IL-23p19 is a VHH, such as a VHH from camelids, the camelids preferably is alpacas or llamas.

In some preferred embodiments, the immunoglobulin single variable domain that specifically binds to IL-23p19 is a humanized VHH, which comprises the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 55.

In some embodiments, the amino acid sequence of the humanized VHH comprises one or more amino acid substitutions compared to SEQ ID NO: 55, preferably conservative amino acid substitutions. For example, the amino acid sequence of the humanized immunoglobulin single variable domain comprises 1, 2, 3, 4, 5, 6, 7, 8, 9, or 10 conservative amino acid substitutions compared to SEQ ID NO: 55. In some preferred embodiments, the amino acid sequence of the humanized VHH comprises the amino acid sequence set forth in any one of SEQ ID NOs: 75-79, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in any one of SEQ ID NOs: 75-79 and maintaining the specific binding to IL-23p19. In some more preferred embodiments, the amino acid sequence of the humanized VHH comprises the amino acid sequence set forth in any one of SEQ ID NOs: 75-78, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence as shown in any one of SEQ ID NOs: 75-78 and maintaining the specific binding to IL-23p19. In some even more preferred embodiments, the amino acid sequence of the humanized VHH comprises the amino acid sequence set forth in SEQ ID NO: 77, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 77 and maintaining the specific binding to IL-23p19.

In some embodiments, the IL-23p19-binding molecule is an anti-IL-23p19 antibody or antigen-binding fragment thereof. In some further embodiments, the IL-23p19-binding molecule is a heavy chain antibody, a heavy chain single domain antibody, a chimeric antibody or a humanized antibody.

In some embodiments, the TL1A-binding molecule provided by the present disclosure comprises a plurality of antigen-binding units that specifically bind to TL1A. In some embodiments, the IL-23p19-binding molecule provided by the present disclosure comprises a plurality of immunoglobulin single variable domains that specifically bind to IL-23p19. The plurality of antigen-binding units or immunoglobulin single variable domains may be directly or indirectly connected to each other, thereby generating a multivalent antigen-binding molecule.

In some embodiments, the TL1A-binding molecule provided by the present disclosure comprises at least one antigen-binding unit that specifically binds to TL1A and further comprises an immunoglobulin Fc domain. In some embodiments, the IL-23p19-binding molecule provided by the present disclosure comprises at least one immunoglobulin single variable domain that specifically binds to IL-23p19 and further comprises an immunoglobulin Fc domain. The Fc domain that can be used in the present disclosure may be derived from different immunoglobulin subtypes, such as IgG (e.g., IgG1, IgG2, IgG3, or IgG4 subtypes), IgA1, IgA2, IgD, IgE, or IgM. The immunoglobulin Fc domain is preferably a human immunoglobulin Fc domain, such as the Fc domain of human IgG1, IgG2, IgG3, or IgG4. In some embodiments, the TL1A-binding molecule and/or IL-23p19-binding molecule provided herein comprise an Fc domain derived from a human IgG1 (the amino acid sequence thereof is as shown in SEQ ID NO: 99). In some embodiments, the TSLP-binding molecule and/or IL-23p19-binding molecule provided herein comprise a variant of the Fc domain derived from a human IgG1. In some embodiments, the variant of the Fc domain derived from a human IgG1 comprises one or more mutations selected from $C_{220}A$, $L_{234}A$, $L_{235}A$, $M_{252}Y$, $S_{254}T$, $T_{256}E$, and $K_{447}$del. In some embodiments, the variant of the Fc domain derived from a human IgG1 comprises the $L_{234}A$ and $L_{235}A$ mutations. In some embodiments, the variant of the Fc domain derived from a human IgG1 comprises the $C_{220}A$, $L_{234}A$, and $L_{235}A$ mutations. In some embodiments, the variant of the Fc domain derived from a human IgG1 comprises the $L_{234}A$, $L_{235}A$, $M_{252}Y$, $S_{254}T$, $T_{256}E$, and $K_{447}$del mutations. In some particular embodiments, the amino acid sequence of the immunoglobulin Fc domain variant is as shown in SEQ ID NO: 100, 118, or 119.

In some embodiments, in the TL1A-binding molecule and/or IL-23p19-binding molecule provided by the present disclosure, the immunoglobulin Fc domain (e.g., the Fc domain of human IgG1) may be directly or indirectly connected to the C-terminus and/or N-terminus of the antigen-binding unit or the immunoglobulin single variable domain via a hinge region or a linker. The inclusion of an immunoglobulin Fc domain in the TL1A-binding molecule and/or IL-23p19-binding molecule provided by the present disclosure can enable the binding molecule to form a dimeric molecule. In some embodiments, the dimer is a homodimer. In some embodiments, the dimer is a heterodimer.

In some embodiments, when the C-terminus of the IL-23p19-targeting immunoglobulin single variable domain provided by the present disclosure is not connected to another domain (such as the Fc domain), in order to reduce the immunogenicity of the immunoglobulin single variable domain, an extension of 1 to 5 amino acids, such as a single alanine extension, may be included at the C-terminus of the immunoglobulin single variable domain.

In some embodiments, the plurality of immunoglobulin variable domains that specifically bind to the target antigen in the TL1A-binding molecule and/or IL-23p19-binding molecule may bind to different regions or different epitopes of the target antigen.

The plurality of antigen-binding units, the plurality of immunoglobulin single variable domains, and/or the antigen-binding units or immunoglobulin single variable domains and the immunoglobulin Fc domain in the present disclosure may be directly connected or indirectly connected via a linker. The linker may be a non-functional amino acid sequence with a length of 1-20 or more amino acids and without secondary or higher structures. For example, the linker is a flexible linker, such as (GS)n, (GGS)n, (GGGS)n, or (GGGGS)n, wherein n is 1, 2, 3, 4, or 5. In some embodiments, the linker is $(GGGGS)_3$. In some embodiments, the linker is $(GGGGS)_4$.

In some embodiments, the antigen-binding unit targeting TL1A comprises an immunoglobulin heavy chain, which comprises the amino acid sequence set forth in SEQ ID NO: 83, 85, 87, 89, 91, 93, 95, or 97, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 83, 85, 87, 89, 91, 93, 95, or 97.

In some embodiments, the antigen-binding unit targeting TL1A comprises an immunoglobulin light chain, which comprises the amino acid sequence set forth in SEQ ID NO: 84, 86, 88, 90, 92, 94, 96, or 98, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 84, 86, 88, 90, 92, 94, 96, or 98.

In some embodiments, the antigen-binding unit targeting TL1A comprises an immunoglobulin heavy chain and an immunoglobulin light chain, wherein:

1) the immunoglobulin heavy chain comprises the amino acid sequence set forth in SEQ ID NO: 83, and the immunoglobulin light chain comprises the amino acid sequence set forth in SEQ ID NO: 84;
2) the immunoglobulin heavy chain comprises the amino acid sequence set forth in SEQ ID NO: 85, and the immunoglobulin light chain comprises the amino acid sequence set forth in SEQ ID NO: 86;
3) the immunoglobulin heavy chain comprises the amino acid sequence set forth in SEQ ID NO: 87, and the immunoglobulin light chain comprises the amino acid sequence set forth in SEQ ID NO: 88;
4) the immunoglobulin heavy chain comprises the amino acid sequence set forth in SEQ ID NO: 89, and the immunoglobulin light chain comprises the amino acid sequence set forth in SEQ ID NO: 90;
5) the immunoglobulin heavy chain comprises the amino acid sequence set forth in SEQ ID NO: 91, and the immunoglobulin light chain comprises the amino acid sequence set forth in SEQ ID NO: 92;
6) the immunoglobulin heavy chain comprises the amino acid sequence set forth in SEQ ID NO: 93, and the immunoglobulin light chain comprises the amino acid sequence set forth in SEQ ID NO: 94;
7) the immunoglobulin heavy chain comprises the amino acid sequence set forth in SEQ ID NO: 95, and the immunoglobulin light chain comprises the amino acid sequence set forth in SEQ ID NO: 96; or
8) the immunoglobulin heavy chain comprises the amino acid sequence set forth in SEQ ID NO: 97, and the immunoglobulin light chain comprises the amino acid sequence set forth in SEQ ID NO: 98.

In some preferred embodiments, the antigen-binding unit targeting TL1A comprises an immunoglobulin heavy chain and an immunoglobulin light chain, wherein:

1) the immunoglobulin heavy chain comprises the amino acid sequence set forth in SEQ ID NO: 87, and the immunoglobulin light chain comprises the amino acid sequence set forth in SEQ ID NO: 88; or
2) the immunoglobulin heavy chain comprises the amino acid sequence set forth in SEQ ID NO: 91, and the immunoglobulin light chain comprises the amino acid sequence set forth in SEQ ID NO: 92.

In some embodiments, the IL-23p19-binding molecule comprises the amino acid sequence set forth in any one of SEQ ID NOs: 101-113, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in any one of SEQ ID NOs: 101-113, and maintaining the specific binding to IL-23p19.

In some preferred embodiments, the IL-23p19-binding molecule comprises the amino acid sequence set forth in any one of SEQ ID NO: 101, 103, 105, 106, 107, 109, 110, 111, or 112, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in any one of SEQ ID NO: 101, 103, 105, 106, 107, 109, 110, 111, or 112, and maintaining the specific binding to IL-23p19. In some more preferred embodiments, the IL-23p19-binding molecule comprises the amino acid sequence set forth in any one of SEQ ID NO: 103, 109, 110, 111, or 112, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in any one of SEQ ID NO: 103, 109, 110, 111, or 112, and maintaining the specific binding to IL-23p19. In some even more preferred embodiments, the IL-23p19-binding molecule comprises the amino acid sequence set forth in SEQ ID NO: 111, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 111, and maintaining the specific binding to IL-23p19.

Multispecific Antigen-Binding Molecules

In another aspect, the present disclosure also provides a multispecific antigen-binding molecule, which comprises the TL1A-binding molecule and/or the IL-23p19-binding molecule provided by the present disclosure.

The term "multispecific" refers to the ability of an antigen-binding molecule to specifically bind to various different target antigens or antigen epitopes. For example, "bispecific" means that the antigen-binding molecule can specifically bind to two different target antigens or antigen epitopes.

In some embodiments, in addition to the TL1A-binding molecule and/or the IL-23p19-binding molecule, the multispecific antigen-binding molecule further comprises one or more additional antigen-binding domains that bind to different antigens or different epitopes of the same antigen compared to the TL1A-binding molecule and/or the IL-23p19-binding molecule.

Bispecific Antigen-Binding Molecules

In another aspect, the present disclosure also provides a TL1A×IL-23p19 bispecific antigen-binding molecule, which can simultaneously target both TL1A and IL-23p19, and inhibit or block the signaling of both TL1A and IL-23p19.

In some embodiments, the bispecific antigen-binding molecule comprises the TL1A-binding molecule and IL-23p19-binding molecule provided by the present disclosure.

In some embodiments, the bispecific antigen-binding molecule comprises a first antigen-binding functional region and a second antigen-binding functional region, wherein the first antigen-binding functional region comprises at least one antigen-binding unit targeting TL1A comprising an immunoglobulin heavy chain variable domain (VH) and an immunoglobulin light chain variable domain (VL), wherein:

1) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 3, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 6;
2) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 11, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 13;
3) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 16, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 19;
4) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 22, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 23;
5) the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29;
6) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 32, and the VL comprises an LCDR1 comprising the amino acid sequence set forth in SEQ ID NO: 4, an LCDR2 comprising the amino acid sequence set forth in SEQ ID NO: 5, and an LCDR3 comprising the amino acid sequence set forth in SEQ ID NO: 33;
7) the VH comprises an HCDR1 comprising the amino acid sequence set forth in SEQ ID NO: 9, an HCDR2 comprising the amino acid sequence set forth in SEQ ID NO: 10, and an HCDR3 comprising the amino acid sequence set forth in SEQ ID NO: 36, and the VL comprises an LCDR1 comprising the amino acid sequence set forth in SEQ ID NO: 12, an LCDR2 comprising the amino acid sequence set forth in SEQ ID NO: 5, and an LCDR3 comprising the amino acid sequence set forth in SEQ ID NO: 37; or
8) the VH comprises an HCDR1 comprising the amino acid sequence set forth in SEQ ID NO: 1, an HCDR2 comprising the amino acid sequence set forth in SEQ ID NO: 2, and an HCDR3 comprising the amino acid sequence set forth in SEQ ID NO: 40, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 41;

and the second antigen-binding functional region comprises at least one immunoglobulin single variable domain that specifically binds to IL-23p19 comprising:

1) a CDR1 comprising the amino acid sequence set forth in SEQ ID NO: 44, a CDR2 comprising the amino acid sequence set forth in SEQ ID NO: 45, and a CDR3 comprising the amino acid sequence set forth in SEQ ID NO: 46;

2) a CDR1 comprising the amino acid sequence set forth in SEQ ID NO: 48, a CDR2 comprising the amino acid sequence set forth in SEQ ID NO: 49, and a CDR3 comprising the amino acid sequence set forth in SEQ ID NO: 50;

3) a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54;

4) a CDR1 comprising the amino acid sequence set forth in SEQ ID NO: 56, a CDR2 comprising the amino acid sequence set forth in SEQ ID NO: 57, and a CDR3 comprising the amino acid sequence set forth in SEQ ID NO: 58;

5) a CDR1 comprising the amino acid sequence set forth in SEQ ID NO: 60, a CDR2 comprising the amino acid sequence set forth in SEQ ID NO: 61, and a CDR3 comprising the amino acid sequence set forth in SEQ ID NO: 62;

6) a CDR1 comprising the amino acid sequence set forth in SEQ ID NO: 64, a CDR2 comprising the amino acid sequence set forth in SEQ ID NO: 65, and a CDR3 comprising the amino acid sequence set forth in SEQ ID NO: 62;

7) a CDR1 comprising the amino acid sequence set forth in SEQ ID NO: 67, a CDR2 comprising the amino acid sequence set forth in SEQ ID NO: 68, and a CDR3 comprising the amino acid sequence set forth in SEQ ID NO: 69; or 8) a CDR1 comprising the amino acid sequence set forth in SEQ ID NO: 71, a CDR2 comprising the amino acid sequence set forth in SEQ ID NO: 72, and a CDR3 comprising the amino acid sequence set forth in SEQ ID NO: 73.

In some embodiments, the antigen-binding unit targeting TL1A comprises an immunoglobulin heavy chain variable domain (VH) and an immunoglobulin light chain variable domain (VL), wherein:

1) the VH comprises the amino acid sequence set forth in SEQ ID NO: 7, and the VL comprises the amino acid sequence set forth in SEQ ID NO: 8;

2) the VH comprises the amino acid sequence set forth in SEQ ID NO: 14, and the VL comprises the amino acid sequence set forth in SEQ ID NO: 15;

3) the VH comprises the amino acid sequence set forth in SEQ ID NO: 20, and the VL comprises the amino acid sequence set forth in SEQ ID NO: 21;

4) the VH comprises the amino acid sequence set forth in SEQ ID NO: 24, and the VL comprises the amino acid sequence set forth in SEQ ID NO: 25;

5) the VH comprises the amino acid sequence set forth in SEQ ID NO: 30, and the VL comprises the amino acid sequence set forth in SEQ ID NO: 31;

6) the VH comprises the amino acid sequence set forth in SEQ ID NO: 34, and the VL comprises the amino acid sequence set forth in SEQ ID NO: 35;

7) the VH comprises the amino acid sequence set forth in SEQ ID NO: 38, and the VL comprises the amino acid sequence set forth in SEQ ID NO: 39;

8) the VH comprises the amino acid sequence set forth in SEQ ID NO: 42, and the VL comprises the amino acid sequence set forth in SEQ ID NO: 43; or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the above-mentioned amino acid sequences, and maintaining the specific binding to TL1A;

and the immunoglobulin single variable domain that specifically binds to IL-23p19 comprises the amino acid sequence set forth in SEQ ID NO: 47, 51, 55, 59, 63, 66, 70, 74, 75, 76, 77, 78 or 79, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 47, 51, 55, 59, 63, 66, 70, 74, 75, 76, 77, 78 or 79, and maintaining the specific binding to IL-23p19.

In some preferred embodiments, the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29.

In some preferred embodiments, the VH comprises the amino acid sequence set forth in SEQ ID NO: 30, and the VL comprises the amino acid sequence set forth in SEQ ID NO: 31, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 30 or 31, and maintaining the specific binding to TL1A.

In some preferred embodiments, the immunoglobulin single variable domain that specifically binds to IL-23p19 comprises a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54.

In some preferred embodiments, the immunoglobulin single variable domain that specifically binds to IL-23p19 comprises the amino acid sequence set forth in SEQ ID NO: 77, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 77, and maintaining the specific binding to IL-23p19.

In some more preferred embodiments, the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29; and the immunoglobulin single variable domain comprises a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54.

In some more preferred embodiments, the VH comprises the amino acid sequence set forth in SEQ ID NO: 30, and the VL comprises the amino acid sequence set forth in SEQ ID NO: 31, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 30 or 31, and maintaining the specific binding to TL1A; and the immunoglobulin single variable domain comprises the amino acid sequence set forth in SEQ ID NO: 77, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 77, and maintaining the specific binding to IL-23p19.

In some embodiments, the immunoglobulin single variable domain is a VHH, such as a VHH from camelids, the camelids preferably is alpacas or llamas. In some preferred embodiments, the immunoglobulin single variable domain that specifically binds to IL-23p19 is a humanized VHH.

In some embodiments, the antigen-binding unit targeting TL1A is F(ab), F(ab'), $F(ab')_2$, scFab, Fd, Fv, dsFv, dAb, diabody, or scFv.

In some preferred embodiments, the antigen-binding unit targeting TL1A is F(ab), and the VH is connected to the immunoglobulin CH1 domain, and the VL is connected to the immunoglobulin light chain constant domain.

In some embodiments, the immunoglobulin CH1 domain is a human immunoglobulin CH1 domain, preferably derived from a human IgG, more preferably derived from a human IgG1 or IgG4; and/or, the immunoglobulin light chain constant domain is derived from a human λ light chain constant domain or κ light chain constant domain.

In some embodiments, the immunoglobulin CH1 domain sequence comprises the amino acid sequence set forth in SEQ ID NO: 117, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 117; and/or, the immunoglobulin light chain constant domain sequence comprises the amino acid sequence set forth in SEQ ID NO: 82, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 82.

In some embodiments, the first antigen-binding functional region in the TL1A×IL-23p19 bispecific antigen-binding molecule provided by the present disclosure comprises a plurality of antigen-binding units that specifically bind to TL1A and/or the second antigen-binding functional region comprises a plurality of immunoglobulin single variable domains that specifically bind to IL-23p19, and the plurality of immunoglobulin single variable domains may be directly or indirectly connected to each other.

In some embodiments, the numbers of the first and second antigen-binding functional regions are each independently 1, 2, or more than 2.

In some embodiments, in addition to the antigen-binding functional regions, the TL1A×IL-23p19 bispecific antigen-binding molecule provided by the present disclosure further comprises an immunoglobulin Fc domain. The Fc domain used in the present disclosure may be derived from different immunoglobulin subtypes, such as IgG (e.g., IgG1, IgG2, IgG3, or IgG4 subtypes), IgA1, IgA2, IgD, IgE, or IgM. The immunoglobulin Fc domain is preferably a human immunoglobulin Fc domain, such as the Fc domain of human IgG1, IgG2, IgG3, or IgG4. In some embodiments, the TL1A×IL-23p19 bispecific antigen-binding molecule provided herein comprises an Fc domain derived from a human IgG1 (the amino acid sequence thereof is as shown in SEQ ID NO: 99). In some embodiments, the TL1A×IL-23p19 bispecific antigen-binding molecule provided herein comprises a variant of the Fc domain derived from a human IgG1. In some embodiments, the variant of the Fc domain derived from a human IgG1 comprises one or more mutations selected from $C_{220}A$, $L_{234}A$, $L_{235}A$, $M_{252}Y$, $S_{254}T$, $T_{256}E$, and $K_{447}del$. In some embodiments, the variant of the Fc domain derived from a human IgG1 comprises the $L_{234}A$ and $L_{235}A$ mutations. In some embodiments, the variant of the Fc domain derived from a human IgG1 comprises the $C_{220}A$, $L_{234}A$, and $L_{235}A$ mutations. In some embodiments, the variant of the Fc domain derived from a human IgG1 comprises the $L_{234}A$, $L_{235}A$, $M_{252}Y$, $S_{254}T$, $T_{256}E$, and $K_{447}del$ mutations. In some particular embodiments, the amino acid sequence of the immunoglobulin Fc domain variant is as shown in SEQ ID NO: 100, 118, or 119.

In some embodiments, in the TL1A×IL-23p19 bispecific antigen-binding molecule provided by the present disclosure, the immunoglobulin Fc domain (e.g., the Fc domain of a human IgG1) is directly or indirectly connected to the C-terminus and/or N-terminus of the first and/or second antigen-binding functional region via a hinge region or a linker. The inclusion of an immunoglobulin Fc domain in the TL1A-binding molecule and/or IL-23p19-binding molecule provided by the present disclosure can enable the binding molecule to form a dimeric molecule. In some embodiments, the dimer is a homodimer. In some embodiments, the dimer is a heterodimer.

In some specific embodiments, the TL1A×IL-23p19 bispecific antigen-binding molecule comprises: an immunoglobulin heavy chain, which comprises from the N-terminus to the C-terminus: the VH, the immunoglobulin CH1 domain, the Fc domain, an optional linker, and the immunoglobulin single variable domain; and an immunoglobulin light chain, which comprises from the N-terminus to the C-terminus: the VL and the immunoglobulin light chain constant domain.

In some embodiments, when the C-terminus of the immunoglobulin single variable domain targeting IL-23p19 provided by the present disclosure is not connected to another domain (such as the Fc domain), in order to reduce the immunogenicity of the immunoglobulin single variable domain, an extension of 1 to 5 amino acids, such as a single alanine extension, may be included at the C-terminus of the immunoglobulin single variable domain.

The plurality of antigen-binding units, the plurality of immunoglobulin single variable domains, the plurality of antigen-binding functional regions and/or the antigen-binding units, immunoglobulin single variable domains, antigen-binding functional regions and the immunoglobulin Fc domain in the present disclosure may be directly connected or indirectly connected via a linker. The linker may be a non-functional amino acid sequence with a length of 1-20 or more amino acids and without secondary or higher structures. For example, the linker is a flexible linker, such as (GS)n, (GGS)n, (GGGS)n, or (GGGGS)n, wherein n is 1, 2, 3, 4, or 5. In some embodiments, the linker is $(GGGGS)_3$. In some embodiments, the linker is $(GGGGS)_4$.

In some embodiments, the TL1A×IL-23p19 bispecific antigen-binding molecule comprises an immunoglobulin heavy chain and an immunoglobulin light chain, wherein the immunoglobulin heavy chain comprises the amino acid sequence set forth in SEQ ID NO: 115 or 116, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 115 or 116; and the immunoglobulin light chain comprises the amino acid sequence set forth in SEQ ID NO: 92, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 92, and maintaining the specific binding to TL1A and IL-23p19.

Fusion Proteins

In another aspect, the present disclosure also provides a fusion protein, which comprises the TL1A-binding molecule, IL-23p19-binding molecule, multispecific antigen-binding molecule, and/or bispecific antigen-binding molecule described herein, and a polypeptide or protein that is expressed in fusion therewith.

In some embodiments, in addition to the TL1A-binding molecule, IL-23p19-binding molecule, multispecific antigen-binding molecule, and/or bispecific antigen-binding molecule, the fusion protein further comprises one or more additional bioactive proteins. These bioactive proteins can be any protein that has biological, therapeutic, preventive, or diagnostic significance or function. When administered to a subject, they may mediate bioactivity and prevent or alleviate diseases, disorders, or conditions. Specifically, the bioactive proteins can be an agonist, antagonist, modulator, ligand, cytokine, enzyme, or hormone, particularly bioactive proteins that can be used for the treatment, prevention, and/or alleviation of inflammatory diseases.

Conjugates

In another aspect, the present disclosure provides a conjugate, which comprise the TL1A-binding molecule, the IL-23p19-binding molecule, the multispecific antigen-binding molecule, the bispecific antigen-binding molecule, and/or the fusion protein described herein, and a conjugate that is conjugated thereto.

In this context, the term "conjugation" refers to any method known in the art for functionally connecting protein domains, including but not limited to: recombinant fusion with or without a linker, intein-mediated fusion, non-covalent binding, and covalent bonding, such as disulfide bonding, peptide bonding, hydrogen bonding, electrostatic bonding, and conformational bonding, for example, biotin-avidin binding. In some embodiments, conjugation to an effector can be performed by chemical or recombinant methods, and the chemical method involves forming a covalent bond between two molecules to generate a single molecule.

In this context, the term "conjugate" refers to a component or functional group that can modulate (e.g., increase or decrease) the natural activity of the molecule to which it is attached or confer novel activity on that molecule. In some embodiments, the effector is a biologically active compound or polypeptide, or a non-proteinaceous module, such as a detectable label or a water-soluble polymer.

In some embodiments, the conjugate can be a therapeutic moiety, which refers to a compound or polypeptide that can be used as a therapeutic agent. In some embodiments, the therapeutic moiety comprises therapeutic agents or drugs for the treatment of inflammatory diseases and/or autoimmune diseases. In some embodiments, the conjugate moiety comprises an immunosuppressant, cytokine inhibitor, metabolic inhibitor, antioxidant, corticosteroid, etc.

In some embodiments, the conjugate can be a detectable label. The detectable label described by the present disclosure can be any substance that can be detected by fluorescent, spectroscopic, photochemical, biochemical, immunological, electrical, optical, or chemical means. Such labels are well-known in the art, and examples include, but are not limited to, enzymes (e.g., horseradish peroxidase), radioisotopes (e.g., 3H), fluorescent dyes (e.g., fluorescein isothiocyanate (FITC)), luminescent substances (e.g., acridinium ester compounds), magnetic beads, and biotin for binding to avidin (e.g., streptavidin) modified with the above-mentioned labels.

In certain embodiments, the conjugate moiety can be a water-soluble polymer that helps increase the half-life of the antibody. Non-limiting examples of water-soluble polymers include, but are not limited to, polyethylene glycol (PEG), ethylene glycol/propylene glycol copolymers, carboxymethyl cellulose, polyvinyl alcohol, polyvinylpyrrolidone, etc. The polymer can be of any molecular weight and can be branched or unbranched. The number of polymers attached to the antibody can vary, and if more than one polymer is attached, they can be the same or different molecules.

In certain embodiments, the antigen-binding molecules provided herein are used as the substrate for the conjugate.

Variants of Antigen-Binding Molecule

In some embodiments, the antigen-binding molecules provided herein also encompass variants of the amino acid sequences provided herein.

In some embodiments, the variants comprise one or more CDR sequences and/or one or more amino acid modifications or substitutions in one or more non-CDR sequences and/or constant regions (e.g., Fc domain) within the immunoglobulin light chain variable domain, immunoglobulin heavy chain variable domain, and immunoglobulin single variable domain provided herein. These variants retain the binding specificity of the parent antibody but possess one or more desired properties conferred by the modifications or substitutions. For example, the antibody variants may have improved antigen-binding affinity, improved glycosylation patterns, reduced risk of glycosylation, reduced deamination, reduced or eliminated effector functions, improved FcRn receptor binding, enhanced pharmacokinetic half-life, pH sensitivity, and/or compatibility for conjugation (e.g., one or more introduced cysteine residues).

Suitable modifications can be introduced into the nucleotide sequences encoding the antibodies using methods known in the art, or the amino acid sequence variants of the antibodies can be prepared by peptide synthesis. Such modifications include, for example, deletions of residues within the amino acid sequence of the antibodies, and/or insertions and/or substitutions. Any combination of deletions, insertions, and substitutions can be made to achieve the final construct, as long as the final construct has the desired characteristics.

Variants with Substitution, Insertion, and Deletion

In some embodiments, antibody variants with one or more amino acid substitutions are provided. Sites of interest for substitutional mutagenesis include CDRs and FRs. Conservative substitutions are as described above. Amino acid substitutions can be introduced into the antibody of interest, and the resulting product can be screened for desired activities, such as retained/improved antigen binding, reduced immunogenicity, or improved ADCC or CDC.

Some substitutional variants involve replacing one or more residues in the complementarity-determining regions of a parent antibody (e.g., a humanized or human antibody). Generally, the resulting variants selected for further study will have changes (e.g., improvements) in certain biological properties (e.g., increased affinity, reduced immunogenicity) relative to the parent antibody, and/or will substantially retain certain biological properties of the parent antibody. Exemplary substitutional variants are affinity-matured antibodies, which can be conveniently generated using phage display-based affinity maturation techniques such as those described herein. Briefly, one or more CDR residues are mutated, and the variant antibodies are displayed on phage and screened for specific biological activity (e.g., binding affinity).

Changes (e.g., substitutions) can be made to the CDRs, for example, to improve antibody affinity. Such changes can be made to CDR "hotspots," which are residues encoded by codons that undergo mutation at a high frequency during somatic maturation (see, for example, Chowdhury, Methods Mol. Biol. 207:179-196 (2008)), and/or to residues that contact the antigen, wherein the resulting variant VH or VL is tested for the binding affinity. Affinity maturation by construction and reselection of secondary libraries has been described, for example, by Hoogenboom et al., in Methods in Molecular Biology 178:1-37 (O'Brien et al., eds., Human Press, Totowa, NJ, (2001)). In some embodiments of affinity maturation, diversity is introduced into the variable gene selected for maturation by various methods (e.g., error-prone PCR, chain shuffling, or oligonucleotide-directed mutagenesis). A secondary library is then created. The library is then screened to identify any antibody variants with the desired affinity. Another method for introducing diversity involves CDR-directed approaches, in which several CDR residues (e.g., 4-6 residues at a time) are randomized. Residues in the CDRs that are involved in antigen binding can be specifically identified, for example, by alanine scanning mutagenesis or modeling. Specifically, CDR-H3 and CDR-L3 are often targeted.

In some embodiments, substitutions, insertions, or deletions can occur within one or more CDRs, as long as such changes do not substantially reduce the antibody's ability to bind to the antigen. For example, conservative changes (e.g., conservative substitutions, as provided herein) that do not substantially reduce binding affinity can be made to the CDRs. For example, such changes can be made outside of antigen-contacting residues in the CDRs.

In some further embodiments, the antibodies disclosed herein (e.g., anti-TL1A antibodies, anti-IL-23p19 antibodies, and multispecific antibodies based thereon) can comprise conservative substitutions or modifications in the amino acids of the heavy chain variable domain, light chain variable domain, and/or immunoglobulin single variable domain. It is understood in the art that certain conservative sequence modifications can be made without eliminating antigen binding (see, for example, Brummell et al. (1993) Biochem 32:1180-8; de Wildt et al. (1997) Prot. Eng. 10:835-41; Komissarov et al. (1997) J. Biol. Chem. 272: 26864-26870; Hall et al. (1992) J. Immunol. 149:1605-12; Kelley and O'Connell (1993) Biochem. 32:6862-35; Adib-Conquy et al. (1998) Int. Immunol. 10:341-6; and Beers et al. (2000) Clin. Can. Res. 6:2835-43).

In some embodiments, the heavy chain variable domain, light chain variable domain, and/or immunoglobulin single variable domain of the antigen-binding molecules provided herein comprise one or more amino acid residue substitutions, additions, and/or deletions in one or more CDR sequences and/or one or more FR sequences. In some embodiments, the variants have no more than 20, 15, 10, 9, 8, 7, 6, 5, 4, 3, 2, or 1 substitutions, additions, and/or deletions in total in the CDR sequences and/or FR sequences.

Variants with Glycosylation

In some embodiments, antibodies provided herein are altered to increase or decrease the extent to which the antibodies are glycosylated. Glycosylation sites can be conveniently added or deleted by altering the amino acid sequence to create or eliminate one or more glycosylation sites.

In cases where the antibody comprises an Fc domain, the attached carbohydrate can be altered. Natural antibodies generated from mammalian cells typically comprise branched, biantennary oligosaccharides that are generally attached to Asn297 in the CH2 domain of the Fc region via N-linkage. See, for example, Wright et al., TIBTECH 15:26-32 (1997). The oligosaccharides can include various carbohydrates, such as mannose, N-acetylglucosamine (GlcNAc), galactose, and sialic acid, as well as fucose attached to GlcNAc in the "backbone" of biantennary oligosaccharide structure. In some embodiments, the oligosaccharides attached to the antibodies of the present disclosure can be modified to create antibody variants with certain improved properties.

Cysteine-Engineered Antibody Variants

In some embodiments, it may be desirable to create cysteine-engineered antibodies, such as "thioMAbs," wherein one or more residues of the antibody are replaced with cysteine residues. In a particular embodiment, the substituted residues are located at accessible sites on the antibody. By substituting those residues with cysteine, reactive thiol groups are thereby positioned at accessible sites on the antibody and can be used to conjugate the antibody to other modules, such as drug module or linker-drug module, to create antibody-drug conjugates, as further described herein. Cysteine-engineered antibodies can be generated as described, for example, in U.S. Pat. No. 7,521,541.

Fc Domain Variants

In some embodiments, one or more amino acid modifications can be introduced into the Fc domain and/or hinge region of the antibodies provided herein, thereby generating Fc domain variants. Fc domain variants can comprise a human Fc domain sequence (e.g., human IgG1, IgG2, IgG3, or IgG4 Fc domain) comprising acid modifications (e.g., substitutions) at one or more amino acid positions, for example, to extend the half-life of the antigen-binding molecule, reduce the effector functions of the antigen-binding molecule, facilitate multimerization of bispecific antibodies, and/or improve the manufacturability and drug stability of bispecific antibodies.

In some embodiments, the present disclosure encompasses antibody variants that have some but not all effector functions, making them desirable candidates for applications, wherein the in vivo half-life of the antibody is important, but certain effector functions (such as CDC and ADCC) are unnecessary or detrimental.

In some embodiments, in cases where the effector functions are not desired, the antibodies disclosed herein can be further engineered to introduce at least one mutation in the antibody Fc domain that reduces the antibody's binding to activating Fcγ receptors (FcγRs) and/or reduces Fc effector functions (such as C1q binding, complement-dependent cytotoxicity (CDC), antibody-dependent cell-mediated cytotoxicity (ADCC), or phagocytosis (ADCP)).

Fc domain positions that can be mutated to reduce the antibody's binding to activating FcγRs and subsequently reduce effector functions are those described, for example, in (Xu, Alegre et al. 2000)(Vafa, Gilliland et al. 2014)(Bolt, Routledge et al. 1993)(Chu, Vostiar et al. 2008)(Shields, Namenuk et al. 2001). Fc mutations that have minimal ADCC, ADCP, CDC, and Fc-mediated cell activation have also been described as a mutations of IgG1, IgG2, and IgG4 (Tam, McCarthy et al. 2017).

Exemplary mutations that can be made individually or in combination are $K_{214}T$, $E_{233}P$, $L_{234}V$, $L_{234}A$, $G_{236}$deletion, $V_{234}A$, $F_{234}A$, $L_{235}A$, $G_{237}A$, $P_{238}A$, $P_{238}S$, $D_{265}A$, $S_{267}E$, $H_{268}A$, $H_{268}Q$, $Q_{268}A$, $N_{297}A$, $A_{327}Q$, $P_{329}A$, $D_{270}A$, $Q_{295}A$, $V_{309}L$, $A_{327}S$, $L_{328}F$, $A_{330}S$ and $P_{331}S$ (according to EU numbering) mutations on IgG1, IgG2, IgG3, or IgG4.

Exemplary combinations of mutations that can be made to reduce ADCC are $L_{234}A/L_{235}A$ on IgG1, $V_{234}A/G_{237}A/P_{238}S/H_{268}A/V_{309}L/A_{330}S/P_{331}S$ on IgG2, $F_{234}A/L_{235}A$ on IgG4, $S_{228}P/F_{234}A/L_{235}A$ on IgG4, $N_{297}A$ on IgG1, IgG2, IgG3, or IgG4, $V_{234}A/G_{237}A$ on IgG2, $K_{214}T/E_{233}P/L_{234}V/L_{235}A/G_{236}$ deletion/$A_{327}G/P_{331}A/D_{365}E/L_{358}M$ on IgG1, $H_{268}Q/V_{309}L/A_{330}S/P_{331}S$ on IgG2, $S_{267}E/L_{328}F$ on IgG1, $L_{234}F/L_{235}E/D_{265}A$ on IgG1, $L_{234}A/L_{235}A/G_{237}A/P_{238}S/H_{268}A/A_{330}S/P_{331}S$ on IgG1, $S_{228}P/F_{234}A/L_{235}A/G_{237}A/P_{238}S$ on IgG4, and $S_{228}P/F_{234}A/L_{235}A/G_{236}$ deletion/$G_{237}A/P_{238}S$ on IgG4. Hybrid IgG2/4 Fe domains, such as Fc with residues 117-260 from IgG2 and residues 261-447 from IgG4 (according to EU numbering), can also be used.

In some embodiments, the present disclosure encompasses antibodies in which the naturally occurring Fc region is modified to extend the half-life of the antibody compared to the parent native antibody in a biological environment, for example, as measured by in vitro assays of serum half-life or half-life.

Exemplary mutations that can be made individually or in combination are $T_{250}Q$, $M_{252}Y$, $I_{253}A$, $S_{254}T$, $T_{256}E$, $P_{2571}$, $T_{307}A$, $D_{376}V$, $E_{380}A$, $M_{428}L$, $H_{433}K$, $N_{434}S$, $N_{434}A$, $N_{434}H$, $N_{434}F$, $H_{435}A$ and $H_{435}R$ (according to EU numbering) mutations.

Exemplary combinations of mutations that can achieve half-life extension are $M_{252}Y/S_{254}T/T_{256}E$, $M_{428}L/N_{434}S$, $T_{250}Q/M_{428}L$, $N_{434}A$, $T_{307}A/E_{380}A/N_{434}A$ (according to EU numbering) on IgG1.

In some embodiments, to avoid light chain mispairing, the present disclosure also encompasses one or more amino acid variants in the hinge region. Exemplary mutations include, for example, $C_{220}A$ (according to EU numbering) in the IgG1 hinge region.

In some embodiments, to avoid protease digestion, the present disclosure also encompasses Fc domain variants with a glycine and/or lysine deletion ($G_{446}$del and/or $K_{447}$del, according to EU numbering) at the C-terminus of the Fc domain.

In some embodiments, the present disclosure encompasses Fc domain variants with one or more amino acid substitutions at the Fc domain interface to help and/or promote Fc domain heterodimerization. These modifications include introducing a protuberance into the first Fc polypeptide and a cavity into the second Fc polypeptide, wherein the protuberance can be positioned in the cavity, thereby promoting the interaction between the first and second Fc polypeptides to form a heterodimer or complex. Methods for producing antibodies with these modifications are known in the art, for example, as described in U.S. Pat. No. 5,731,168.

In some embodiments, the antigen-binding molecules provided herein have the IgG1 isotype and comprise one or more mutations selected from $C_{220}A$, $L_{234}A$, $L_{235}A$, $M_{252}Y$, $S_{254}T$, $T_{256}E$ and $K_{447}$del, or any combination thereof, in the Fc domain. In some embodiments, the antigen-binding molecules provided herein have the IgG1 isotype and comprise the amino acid substitution $L_{234}A/L_{235}A$ (LALA). In some embodiments, the antigen-binding molecules provided herein have the IgG1 isotype and comprise the amino acid substitutions $C_{220}A$ and $L_{234}A/L_{235}A$ (LALA). In some embodiments, the antigen-binding molecules provided herein have the IgG1 isotype and comprise the amino acid substitutions $M_{252}Y/S_{254}T/T_{256}E$ (YTE). In some embodiments, the antigen-binding molecules provided herein have the IgG1 isotype and comprise the amino acid substitutions $L_{234}A/L_{235}A$ (LALA), $M_{252}Y/S_{254}T/T_{256}E$ (YTE), and $K_{447}$del. In some embodiments, the antigen-binding molecules provided herein comprise an Fc domain comprising the amino acid sequence set forth in SEQ ID NO: 99, 100, 118, or 119, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 99, 100, 118, or 119.

Nucleic Acid Molecules, Vectors, Host Cells

In another aspect, the present disclosure also relates to a nucleic acid molecule encoding the TL1A-binding molecule, the IL-23p19-binding molecule, the multispecific antigen-binding molecule, the bispecific antigen-binding molecule, and/or the fusion protein described by the present disclosure.

The nucleic acid molecules can be, for example, DNA, RNA, or hybrids thereof, and may also comprise (e.g., chemically) modified nucleotides, such as PNA. The nucleic acid molecules can be single-stranded or double-stranded. In some embodiments, the nucleic acid molecules are in the form of double-stranded DNA. For example, the nucleic acid molecules of the present disclosure can be genomic DNA or cDNA. In certain embodiments, the nucleic acid molecules of the present disclosure are isolated nucleic acid molecules.

The nucleic acid molecules of the present disclosure can also be in the form of vectors, be present in and/or be part of a vector, such as a plasmid, cosmid, or YAC. The vector may particularly be an expression vector, i.e., a vector that provides for the expression of the TL1A-binding molecules, IL-23p19-binding molecules, multispecific antigen-binding molecules, bispecific antigen-binding molecules, and/or fusion proteins in vitro and/or in vivo (i.e., in a suitable host cell, host organism, and/or expression system). The expression vector typically comprises at least one nucleic acid of the present disclosure operably linked to one or more suitable expression regulatory elements (e.g., promoters, enhancers, terminators, etc.). The selection of the elements and their sequences for expression in a particular host is common knowledge for those skilled in the art. Specific examples of regulatory elements and other elements useful or necessary for the expression of the TL1A-binding molecules, IL-23p19-binding molecules, multispecific antigen-binding molecules, bispecific antigen-binding molecules, and/or fusion proteins of the present disclosure are, for example, promoters, enhancers, terminators, integration factors, selection markers, leader sequences, reporter genes, etc.

The nucleic acids of the present disclosure can be prepared or obtained by known methods based on the information about the amino acid sequences of the peptides of the present disclosure provided herein (e.g., by automated DNA synthesis and/or recombinant DNA techniques), and/or can be isolated from suitable natural origins.

In another aspect, the present disclosure relates to host cells that express or are capable of expressing one or more TL1A-binding molecules, IL-23p19-binding molecules, multispecific antigen-binding molecules, bispecific antigen-binding molecules, fusion proteins, and/or host cells that comprise the nucleic acids or vectors of the present disclosure. Suitable host cells or host organisms will be clear to those skilled in the art, and preferred host cells of the present disclosure are bacterial cells, fungal cells, or mammalian cells.

Suitable bacterial cells include cells of Gram-negative bacterial strains (e.g., *Escherichia coli* strains, *Proteus* strains, and *Pseudomonas* strains) and Gram-positive bacterial strains (e.g., *Bacillus* strains, *Streptomyces* strains, *Staphylococcus* strains, and *Lactococcus* strains).

Suitable fungal cells include cells of species from the genera *Trichoderma, Neurospora*, and *Aspergillus*; or cells of species from the genera *Saccharomyces* (e.g., *Saccharomyces cerevisiae*), *Schizosaccharomyces* (e.g., *Schizosaccharomyces pombe*), *Pichia* (e.g., *Pichia pastoris* and *Pichia methanolica*), and *Hansenula.*

Suitable mammalian cells include, for example, HEK293 cells, CHO cells, BHK cells, HeLa cells, or COS cells, and the like.

However, the present disclosure may also use amphibian cells, insect cells, and any other cells known in the art for the expression of heterologous proteins.

The preparation of the TL1A-binding molecules, IL-23p19-binding molecules, multispecific antigen-binding molecules, bispecific antigen-binding molecules, and/or fusion proteins of the present disclosure can be carried out by transforming/transfecting host cells with the nucleic acid molecules encoding the TL1A-binding molecules, IL-23p19-binding molecules, multispecific antigen-binding molecules, bispecific antigen-binding molecules, and/or fusion proteins or vectors comprising the nucleic acid molecules, culturing the host cells under conditions suitable for expression of the nucleic acid molecules or vectors, and optionally isolating and/or purifying for one or more times from the host cells or the host cell culture.

Methods and reagents for production purposes, such as specific suitable expression vectors, transformation or transfection methods, selective markers, methods for inducing protein expression, culture conditions, etc., are known in the art. Similarly, protein separation and purification techniques suitable for the methods of manufacturing the TL1A-binding molecules, IL-23p19-binding molecules, multispecific antigen-binding molecules, bispecific antigen-binding molecules, and/or fusion proteins of the present disclosure are well-known to those skilled in the art.

Compositions

In some aspects, the present disclosure relates to a composition, which comprises at least one of the TL1A-binding molecule, the IL-23p19-binding molecule, the multispecific antigen-binding molecule, the bispecific antigen-binding molecule, the fusion protein, and/or the conjugate disclosed herein.

In some embodiments, the composition is a pharmaceutical composition, which further comprises at least one pharmaceutically acceptable carrier and/or excipient.

In some embodiments, the pharmaceutical composition may optionally comprise one or more additional therapeutically active agents, such as another therapeutic agent or drug that can be used to treat inflammatory diseases and/or autoimmune diseases.

Pharmaceutically acceptable carriers may include, for example, pharmaceutically acceptable liquid, gel, or solid carriers, aqueous media, non-aqueous media, antimicrobial agents, isotonic agents, buffers, antioxidants, anesthetics, suspending/dispersing agents, chelating agents, diluents, adjuvants, excipients, or non-toxic auxiliary substances, as well as various components or combinations thereof known in the art.

In certain embodiments, the pharmaceutical composition is formulated as an injectable composition. Injectable pharmaceutical compositions can be prepared in any conventional form, such as liquid solutions, suspensions, emulsions, or solid forms suitable for producing liquid solutions, suspensions, or emulsions. Injectable formulations may comprise sterile and/or pyrogen-free solutions that are ready for injection; sterile dry soluble products that are prepared for combination with a solvent just prior to use, such as lyophilized powders, including subcutaneous tablets; sterile suspensions that are ready for injection; sterile dry insoluble products that are prepared for combination with a solvent just prior to use; and sterile and/or pyrogen-free emulsions. The solutions can be aqueous or non-aqueous.

In certain embodiments, unit doses of parenteral formulations are packaged in ampoules, vials, or syringes with needles. All formulations for parenteral administration should be sterile and pyrogen-free, as is known and practiced in the art.

In certain embodiments, formulations suitable for parenteral administration (e.g., by injection) comprise active ingredients dissolved, suspended, or otherwise provided (e.g., in liposomes or other microparticles) in aqueous or non-aqueous, isotonic, pyrogen-free, sterile liquids (e.g., solutions, suspensions). These liquids may additionally contain other pharmaceutically acceptable components, such as antioxidants, buffers, preservatives, stabilizers, antimicrobial agents, suspending agents, thickeners, and solutes that render the formulation isotonic with the blood (or other relevant body fluids) of the intended recipient. Examples of excipients include, for example, water, alcohols, polyols, glycerin, and vegetable oils. Examples of isotonic carriers suitable for such formulations include sodium chloride injection, Ringer's solution, or lactated Ringer's injection.

In certain embodiments, sterile lyophilized powders are prepared by dissolving the antigen-binding molecules disclosed herein in a suitable solvent. The solvent may contain excipients that improve the stability of the powder or the reconstituted solution derived from the powder or other pharmacological components. Suitable excipients include, but are not limited to, water, trehalose, sorbitol, fructose, corn syrup, xylitol, glycerin, glucose, sucrose, or other suitable reagents. The solvent may contain buffers, such as citrate, sodium phosphate, or potassium phosphate, or other such buffers known to those skilled in the art. In one embodiment, the buffer is at approximately neutral pH. The solution is then subjected to sterile filtration under standard conditions known to the person skilled in the art, followed by lyophilization to obtain the desired formulation. In one embodiment, the resulting solution is dispensed into vials for lyophilization. Each vial may contain a single dose or multiple doses of the antigen-binding molecules or their compositions described herein. Overfilling the vial a small amount above that required for a single dose or a set of doses (e.g., about 10%) is acceptable to facilitate accurate sample withdrawal and accurate dosing. The lyophilized powder can be stored under appropriate conditions, such as at approximately 4° C. to room temperature.

Reconstituting the lyophilized powder with water for injection provides a formulation for parenteral administration. In one embodiment, sterile and/or pyrogen-free water or another liquid suitable carrier is added to the lyophilized powder for reconstitution. The precise amount depends on the selected therapy given and can be determined empirically.

Uses

The TL1A-binding molecules, the IL-23p19-binding molecule, the multispecific antigen-binding molecule, the bispecific antigen-binding molecule, the fusion protein, the conjugate, and/or the composition described herein have numerous in vitro and in vivo uses. For example, a therapeutically effective amount of these molecules can be administered in vitro or ex vivo to cultured cells, or administered in vivo to a human subject, to treat, prevent, or alleviate inflammatory diseases in the subject, or to inhibit or block the specific binding of TL1A to DR3 and/or IL-23p19 to the complex of IL-23R and IL-12Rβ1, or to inhibit the activation of downstream signaling pathways mediated by TL1A and/or IL-23p19.

In other aspects, the present disclosure also provides the use of the TL1A-binding molecule, the IL-23p19-binding molecule, the multispecific antigen-binding molecule, the bispecific antigen-binding molecule, the fusion protein, the conjugate, and/or the composition described herein in the preparation of a medicament for the treatment, prevention, and/or alleviation of inflammatory diseases and/or autoimmune diseases.

In some embodiments, the use also comprises administration in combination with another therapeutic agent or drug for the treatment of inflammatory diseases and/or autoimmune diseases. When administered in combination with another therapeutic agent or drug, the two can be administered in any order or simultaneously; when administered sequentially, they can be administered at appropriate intervals to maximize the therapeutic effect.

Preferred subjects include human patients suffering from inflammatory diseases and/or autoimmune diseases. The methods are particularly suitable for treating, preventing, and/or alleviating inflammatory diseases and/or autoimmune diseases in patients who can benefit from blocking the specific binding of TL1A to DR3 and/or IL-23p19 to the complex of IL-23R and IL-12Rβ1, thereby inhibiting the activation of downstream signaling pathways mediated by TL1A and/or IL-23p19, and achieving the purpose of treating, preventing, and/or alleviating inflammatory diseases and/or autoimmune diseases. In a particular embodiment, the method is suitable for in vivo treatment, prevention, and/or alleviation of inflammatory diseases and/or autoimmune diseases, such as asthma, rheumatoid arthritis, multiple sclerosis, inflammatory bowel disease, systemic lupus erythematosus, ankylosing spondylitis, or psoriasis, particularly, the method is suitable for Crohn's disease or ulcerative colitis.

The TL1A-binding molecules, the IL-23p19-binding molecule, the multispecific antigen-binding molecule, the bispecific antigen-binding molecule, the fusion protein, the conjugate, and/or the composition can be administered to subjects via any suitable route of administration. Those skilled in the art will understand that the route and/or method of administration may vary depending on the desired outcome. The preferred routes of administration include intravenous, intramuscular, intradermal, intraperitoneal, subcutaneous, spinal, or other parenteral routes, such as injection or infusion. The term "parenteral administration" used herein refers to a mode of administration other than enteral and topical administration, usually refers to a mode of administration by injection, including but not limited to intravenous, intramuscular, intra-arterial, intrathecal, intracapsular, intraorbital, intracardiac, intradermal, intraperitoneal, trans-tracheal, subcutaneous, subepidermal, intra-articular, subcapsular, subarachnoid, intraspinal, epidural, and intrasternal injection and infusion.

Those skilled in the art will understand that the appropriate dosage may vary from patient to patient. Determining the optimal dosage typically involves balancing the level of therapeutic benefit against any risks or adverse side effects. In some embodiments, the antigen-binding molecules provided herein can be administered at a therapeutically effective dose of about 0.01 mg/kg to about 100 mg/kg. In some embodiments, the dosing regimen can be adjusted to provide the optimal desired response (e.g., therapeutic response). For example, a single dose can be administered, or several divided doses can be administered over time. When more than one dose is administered, the doses can be administered at appropriate intervals to maximize the therapeutic effect. In some embodiments, the administered dosage can vary during the course of treatment depending on the subject's response.

SEQUENCE LISTING

The application is accompanied by a Sequence Listing containing numerous amino acid sequences. Table A below provides an overview of the included amino acid sequences.

TABLE A

Overview of Amino Acid Sequences

| SEQ ID NO | Sequence | Description |
|---|---|---|
| 1 | GFTFDDYAMH | HYB1801's HCDR1 |
| 2 | GISWNSGSIG | HYB1801's HCDR2 |
| 3 | DSGAYVSFDY | HYB1801's HCDR3 |

TABLE A-continued

| SEQ ID NO | Sequence | Description |
|---|---|---|
| | Overview of Amino Acid Sequences | |
| 4 | RASQSISSYLN | HYB1801's LCDR1 |
| 5 | AASSLQS | HYB1801's LCDR2 |
| 6 | QESYSYPPFT | HYB1801's LCDR3 |
| 7 | EVQLVESGGGLVQPGRSLRLSCAASGFTFDDYAMHWVRQAPG KGLEWVSGISWNSGSIGYADSVKGRFTISRDNAKNSLYLQMNSL RAEDTAVYYCARDSGAYVSFDYWGQGTLVTVSS | HYB1801's heavy chain variable domain sequence |
| 8 | DIQMTQSPSSLSASVGDRVTITCRASQSISSYLNWYQQKPGKAPK LLIYAASSLQSGVPSRFSGSGSGTDFTLTISSLQPEDFATYYCQES YSYPPFTFGGGTKVEIK | HYB1801's light chain variable domain sequence |
| 9 | GFTFSSYAMS | HYB1802's HCDR1 |
| 10 | AISGSGGSTY | HYB1802's HCDR2 |
| 11 | LEWLYGAFDI | HYB1802's HCDR3 |
| 12 | RASQGISSWLA | HYB1802's LCDR1 |
| 13 | QQADSFPPLT | HYB1802's LCDR3 |
| 14 | EVQLLESGGGLVQPGGSLRLSCAASGFTFSSYAMSWVRQAPGK GLEWVSAISGSGGSTYYADSVKGRFTISRDNSKNTLYLQMNSLR AEDTAVYYCARLEWLYGAFDIWGQGTLVTVSS | HYB1802's heavy chain variable domain sequence |
| 15 | DIQMTQSPSSVSASVGDRVTITCRASQGISSWLAWYQQKPGKAP KLLIYAASSLQSGVPSRFSGSGSGTDFTLTISSLQPEDFATYYCQQ ADSFPPLTFGGGTKVEIK | HYB1802's light chain variable domain sequence |
| 16 | SYEDTAHFDY | HYB1803's HCDR3 |
| 17 | RASQSISSWLA | HYB1803's LCDR1 |
| 18 | DASSLES | HYB1803's LCDR2 |
| 19 | QQYNSFPPT | HYB1803's LCDR3 |
| 20 | EVQLVESGGGLVQPGRSLRLSCAASGFTFDDYAMHWVRQAPG KGLEWVSGISWNSGSIGYADSVKGRFTISRDNAKNSLYLQMNSL RAEDTAVYYCARSYEDTAHFDYWGQGTLVTVSS | HYB1803's heavy chain variable domain sequence |
| 21 | DIQMTQSPSTLSASVGDRVTITCRASQSISSWLAWYQQKPGKAP KLLIYDASSLESGVPSRFSGSGSGTEFTLTISSLQPDDFATYYCQQ YNSFPPTFGGGTKVEIK | HYB1803's light chain variable domain sequence |
| 22 | GQVAPLDHFDY | HYB1804's HCDR3 |
| 23 | EQYNSYPLT | HYB1804's LCDR3 |
| 24 | EVQLVESGGGLVQPGRSLRLSCAASGFTFDDYAMHWVRQAPG KGLEWVSGISWNSGSIGYADSVKGRFTISRDNAKNSLYLQMNSL RAEDTAVYYCAKGQVAPLDHFDYWGQGTLVTVSS | HYB1804's heavy chain variable domain sequence |
| 25 | DIQMTQSPSTLSASVGDRVTITCRASQSISSWLAWYQQKPGKAP KLLIYDASSLESGVPSRFSGSGSGTEFTLTISSLQPDDFATYYCEQ YNSYPLTFGGGTKVEIK | HYB1804's light chain variable domain sequence |
| 26 | GFTFSSYAMH | HYB1805's HCDR1 |
| 27 | VISYDGSNKY | HYB1805's HCDR2 |
| 28 | GQVAILDYFDY | HYB1805's HCDR3 |
| 29 | QQYNSYPPT | HYB1805's LCDR3 |
| 30 | QVQLVESGGGVVQPGRSLRLSCAASGFTFSSYAMHWVRQAPGK GLEWVAVISYDGSNKYYADSVKGRFTISRDNSKNTLYLQMNSL RAEDTAVYYCARGQVAILDYFDYWGQGTLVTVSS | HYB1805's heavy chain variable domain sequence |

TABLE A-continued

| SEQ ID NO | Sequence | Description |
|---|---|---|
| Overview of Amino Acid Sequences | | |
| 31 | DIQMTQSPSTLSASVGDRVTITCRASQSISSWLAWYQQKPGKAPKLLIYDASSLESGVPSRFSGSGSGTEFTLTISSLQPDDFATYYCQQYNSYPPTFGGGTKVEIK | HYB1805's light chain variable domain sequence |
| 32 | LGDGVTYAFDI | HYB1806's HCDR3 |
| 33 | QQSLDFPPIT | HYB1806's LCDR3 |
| 34 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARLGDGVTYAFDIWGQGTLVTVSS | HYB1806's heavy chain variable domain sequence |
| 35 | DIQMTQSPSSLSASVGDRVTITCRASQSISSYLNWYQQKPGKAPKLLIYAASSLQSGVPSRFSGSGSGTDFTLTISSLQPEDFATYYCQQSLDFPPITFGGGTKVEIK | HYB1806's light chain variable domain sequence |
| 36 | LPSSGSYTAHFDY | HYB1807's HCDR3 |
| 37 | QQGFSFWT | HYB1807's LCDR3 |
| 38 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARLPSSGSYTAHFDYWGQGTLVTVSS | HYB1807's heavy chain variable domain sequence |
| 39 | DIQMTQSPSSVSASVGDRVTITCRASQGISSWLAWYQQKPGKAPKLLIYAASSLQSGVPSRFSGSGSGTDFTLTISSLQPEDFATYYCQQGFSFWTFGGGTKVEIK | HYB1807's light chain variable domain sequence |
| 40 | EGSSSGYSRHGYDYFDY | HYB1808's HCDR3 |
| 41 | QQYRSYPIT | HYB1808's LCDR3 |
| 42 | EVQLVESGGGLVQPGRSLRLSCAASGFTFDDYAMHWVRQAPGKGLEWVSGISWNSGSIGYADSVKGRFTISRDNAKNSLYLQMNSLRAEDTAVYYCAREGSSSGYSRHGYDYFDYWGQGTLVTVSS | HYB1808's heavy chain variable domain sequence |
| 43 | DIQMTQSPSTLSASVGDRVTITCRASQSISSWLAWYQQKPGKAPKLLIYDASSLESGVPSRFSGSGSGTEFTLTISSLQPDDFATYYCQQYRSYPITFGGGTKVEIK | HYB1808's light chain variable domain sequence |
| 44 | GFTFSNFNMK | HYB1901's HCDR1 |
| 45 | SIISSGGTTG | HYB1901's HCDR2 |
| 46 | RRRDSEDY | HYB1901's HCDR3 |
| 47 | QLQLVESGGGLVQPGGSLRLSCAASGFTFSNFNMKWYRQVSGKERELVASIISSGGTTGYADSVKGRFTISRDNAKNTVYLQMNSLKTEDTAVYYCNARRRDSEDYWGQGTQVTVSS | HYB1901's variable domain sequence |
| 48 | GSFFRSIAMA | HYB1902's HCDR1 |
| 49 | TITSDGDTN | HYB1902's HCDR2 |
| 50 | PGSIGY | HYB1902's HCDR3 |
| 51 | QVQLVESGGGLVQPGGSLRLSCAASGSFFRSIAMAWYRQAPGKQRVLVGTITSDGDTNYADSVKGRFTISRDNAKNTMYLQMNSLKPEDTAVYSCNVPGSIGYWSQGTQVTVSS | HYB1902's variable domain sequence |
| 52 | GRTLSSYAMG | HYB1903's HCDR1 |
| 53 | SIGRSTY | HYB1903's HCDR2 |
| 54 | PIVAGFGTVVSGEY | HYB1903's HCDR3 |
| 55 | QVQLVESGGGLVQAGGSLRLSCAASGRTLSSYAMGWFRQAPGKEREFVASIGRSTYYADPVKGRFTISRDNAKNTVYLQMNSLKSEDTAVYYCNAPIVAGFGTVVSGEYWGQGTQVTVSS | HYB1903's variable domain sequence |
| 56 | GSIGNIYDLG | HYB1904's HCDR1 |
| 57 | SITSGGRTI | HYB1904's HCDR2 |

TABLE A-continued

| SEQ ID NO | Sequence | Description |
|---|---|---|
| Overview of Amino Acid Sequences | | |
| 58 | GHELGY | HYB1904's HCDR3 |
| 59 | QVQLVESGGGLVQPGESLTLSCTVSGSIGNIYDLGWYRQASGKQ RELVASITSGGRTIYADSVEGRFTISRNNAKNTVVLQMNSLEPED MAVYYCNLGHELGYWGQGTQVTVSS | HYB1904's variable domain sequence |
| 60 | GFTFSTYAMA | HYB1905's HCDR1 |
| 61 | SIDTSGDNTH | HYB1905's HCDR2 |
| 62 | PNTGWGTRRY | HYB1905's HCDR3 |
| 63 | QLQLVESGGGLVQPGGSLRLSCVASGFTFSTYAMAWYRQRPGK ERELVASIDTSGDNTHYVGAVKGRFTISRDNAKNTVYLQMNGL KPEDTAVYFCNAPNTGWGTRRYWGQGTQVTVSS | HYB1905's variable domain sequence |
| 64 | GFAFSTYAMA | HYB1906's HCDR1 |
| 65 | SIDSSGDNTH | HYB1906's HCDR2 |
| 66 | QLQLVESGGGLVQPGGSLRLSCVASGFAFSTYAMAWYRQRPGK ERELVGSIDSSGDNTHYVDAVKGRFTISRDNAKNTVYLQMNVL KPEDTAVYYCNSPNTGWGTRRYWGQGTQVTVSS | HYB1906's variable domain sequence |
| 67 | GFTFSSYAMA | HYB1907's HCDR1 |
| 68 | SIDSSGYNTH | HYB1907's HCDR2 |
| 69 | PNTGWGSRRY | HYB1907's HCDR3 |
| 70 | QLQLVESGGGLVQPGGSLRLSCAASGFTFSSYAMAWYRQRSGK ERELVASIDSSGYNTHYTDAGKGRFTISRDNAKNTVYLQMNNL KPEDTAVYYCNAPNTGWGSRRYWGQGTQVTVSS | HYB1907's variable domain sequence |
| 71 | GNIGHIYDLG | HYB1908's HCDR1 |
| 72 | SITDNGRTI | HYB1908's HCDR2 |
| 73 | GHWLGY | HYB1908's HCDR3 |
| 74 | QVQLVESGGGLVQPGESLRLSCSVSGNIGHIYDLGWYRQASGK QRELVASITDNGRTIYGDSVKGRFTISRNNVKNTVNLQMNSLTP EDTAVYYCNLGHWLGYWGQGTQVTVSS | HYB1908's variable domain sequence |
| 75 | QVQLLESGGGLVQAGGSLRLSCAASGRTLSSYAMGWFRQAPGK GLEFVASIGRSTYYADPVKGRFTISRDNSKNTVYLQMNSLRAED TAVYYCNAPIVAGFGTVVSGEYWGQGTLVTVSS | HYB1903-hz1's variable domain sequence |
| 76 | QVQLLESGGGLVQPGGSLRLSCAASGRTLSSYAMGWFRQAPGK GLEFVASIGRSTYYADPVKGRFTISRDNSKNTVYLQMNSLRAED TAVYYCNAPIVAGFGTVVSGEYWGQGTLVTVSS | HYB1903-hz2's variable domain sequence |
| 77 | EVQLLESGGGLVQPGGSLRLSCAASGRTLSSYAMGWFRQAPGK GLEFVASIGRSTYYADPVKGRFTISRDNSKNTVYLQMNSLRAED TAVYYCNAPIVAGFGTVVSGEYWGQGTLVTVSS | HYB1903-hz3's variable domain sequence |
| 78 | QVQLLESGGGLVQPGGSLRLSCAASGRTLSSYAMGWFRQAPGK GLEFVASIGRSTYYADSVKGRFTISRDNSKNTVYLQMNSLRAED TAVYYCNAPIVAGFGTVVSGEYWGQGTLVTVSS | HYB1903-hz4's variable domain sequence |
| 79 | QVQLLESGGGLVQPGGSLRLSCAASGRTLSSYAMGWFRQAPGK GLEFVASIGRSTYYADPVKGRFTISRDNSKNTVYLQMNSLRAED TAVYYCAAPIVAGFGTVVSGEYWGQGTLVTVSS | HYB1903-hz5's variable domain sequence |
| 80 | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKVEPKSCDKTHTCPPCPAPELLGGPSVFLFPPKPKDTL MISRTPEVTCVVVDVSHEDPEVKFNWYVDGVEVHNAKTKPREE QYNSTYRVVSVLTVLHQDWLNGKEYKCKVSNKALPAPIEKTIS KAKGQPREPQVYTLPPSREEMTKNQVSLTCLVKGFYPSDIAVEW ESNGQPENNYKTTPPVLDSDGSFFLYSKLTVDKSRWQQGNVFSC SVMHEALHNHYTQKSLSLSPGK | Human IgG1 heavy chain constant domain sequence |

TABLE A-continued

| SEQ ID NO | Sequence | Description |
|---|---|---|
| | Overview of Amino Acid Sequences | |
| 81 | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKVEPKSCDKTHTCPPCPAPEAAGGPSVFLFPPKPKDT LMISRTPEVTCVVVDVSHEDPEVKFNWYVDGVEVHNAKTKPRE EQYNSTYRVVSVLTVLHQDWLNGKEYKCKVSNKALPAPIEKTIS KAKGQPREPQVYTLPPSREEMTKNQVSLTCLVKGFYPSDIAVEW ESNGQPENNYKTTPPVLDSDGSFFLYSKLTVDKSRWQQGNVFSC SVMHEALHNHYTQKSLSLSPGK | Human IgG1 heavy chain constant domain sequence comprising $L_{234}A/L_{235}A$ mutations |
| 82 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC | Light chain constant domain (Cκ) sequence |
| 83 | EVQLVESGGGLVQPGRSLRLSCAASGFTFDDYAMHWVRQAPG KGLEWVSGISWNSGSIGYADSVKGRFTISRDNAKNSLYLQMNSL RAEDTAVYYCARDSGAYVSFDYWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSREEMTKNQVSLTCLVKGFYPSDIAVEWESNGQPENN YKTTPPVLDSDGSFFLYSKLTVDKSRWQQGNVFSCSVMHEALH NHYTQKSLSLSPGK | HYB1801's heavy chain full length sequence |
| 84 | DIQMTQSPSSLSASVGDRVTITCRASQSISSYLNWYQQKPGKAPK LLIYAASSLQSGVPSRFSGSGSGTDFTLTISSLQPEDFATYYCQES YSYPPFTFGGGTKVEIKRTVAAPSVFIFPPSDEQLKSGTASVVCLL NNFYPREAKVQWKVDNALQSGNSQESVTEQDSKDSTYSLSSTL TLSKADYEKHKVYACEVTHQGLSSPVTKSFNRGEC | HYB1801's light chain full length sequence |
| 85 | EVQLLESGGGLVQPGGSLRLSCAASGFTFSSYAMSWVRQAPGK GLEWVSAISGSGGSTYYADSVKGRFTISRDNSKNTLYLQMNSLR AEDTAVYYCARLEWLYGAFDIWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVE PKSCDKTHTCPPCPAPEAAGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPQ VYTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK | HYB1802's heavy chain full length sequence |
| 86 | DIQMTQSPSSVSASVGDRVTITCRASQGISSWLAWYQQKPGKAP KLLIYAASSLQSGVPSRFSGSGSGTDFTLTISSLQPEDFATYYCQQ ADSFPPLTFGGGTKVEIKRTVAAPSVFIFPPSDEQLKSGTASVVCL LNNFYPREAKVQWKVDNALQSGNSQESVTEQDSKDSTYSLSST LTLSKADYEKHKVYACEVTHQGLSSPVTKSFNRGEC | HYB1802's light chain full length sequence |
| 87 | EVQLVESGGGLVQPGRSLRLSCAASGFTFDDYAMHWVRQAPG KGLEWVSGISWNSGSIGYADSVKGRFTISRDNAKNSLYLQMNSL RAEDTAVYYCARSYEDTAHFDYWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSREEMTKNQVSLTCLVKGFYPSDIAVEWESNGQPENN YKTTPPVLDSDGSFFLYSKLTVDKSRWQQGNVFSCSVMHEALH NHYTQKSLSLSPGK | HYB1803's heavy sequence chain full length |
| 88 | DIQMTQSPSTLSASVGDRVTITCRASQSISSWLAWYQQKPGKAP KLLIYDASSLESGVPSRFSGSGSGTEFTLTISSLQPDDFATYYCQQ YNSFPPTFGGGTKVEIKRTVAAPSVFIFPPSDEQLKSGTASVVCLL NNFYPREAKVQWKVDNALQSGNSQESVTEQDSKDSTYSLSSTL TLSKADYEKHKVYACEVTHQGLSSPVTKSFNRGEC | HYB1803's light chain full length sequence |
| 89 | EVQLVESGGGLVQPGRSLRLSCAASGFTFDDYAMHWVRQAPG KGLEWVSGISWNSGSIGYADSVKGRFTISRDNAKNSLYLQMNSL RAEDTAVYYCAKGQVAPLDHFDYWGQGTLVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDKK VEPKSCDKTHTCPPCPAPEAAGGPSVFLFPPKPKDTLMISRTPEV TCVVVDVSHEDPEVKFNWYVDGVEVHNAKTKPREEQYNSTYR | HYB1804's heavy chain full length sequence |

TABLE A-continued

| SEQ ID NO | Sequence | Description |
|---|---|---|
| | VVSVLTVLHQDWLNGKEYKCKVSNKALPAPIEKTISKAKGQPR EPQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGK | |
| 90 | DIQMTQSPSTLSASVGDRVTITCRASQSISSWLAWYQQKPGKAP KLLIYDASSLESGVPSRFSGSGSGTEFTLTISSLQPDDFATYYCEQ YNSYPLTFGGGTKVEIKRTVAAPSVFIFPPSDEQLKSGTASVVCL LNNFYPREAKVQWKVDNALQSGNSQESVTEQDSKDSTYSLSST LTLSKADYEKHKVYACEVTHQGLSSPVTKSFNRGEC | HYB1804's light chain full length sequence |
| 91 | QVQLVESGGGVVQPGRSLRLSCAASGFTFSSYAMHWVRQAPGK GLEWVAVISYDGSNKYYADSVKGRFTISRDNSKNTLYLQMNSL RAEDTAVYYCARGQVAILDYFDYWGQGTLVTVSSASTKGPSVF PLAPSSKSTSGGTAALGCLVKDYFPEPVTVSWNSGALTSGVHTF PAVLQSSGLYSLSSVVTVPSSSLGTQTYICNVNHKPSNTKVDKK VEPKSCDKTHTCPPCPAPEAAGGPSVFLFPPKPKDTLMISRTPEV TCVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGK | HYB1805's heavy chain full length sequence |
| 92 | DIQMTQSPSTLSASVGDRVTITCRASQSISSWLAWYQQKPGKAP KLLIYDASSLESGVPSRFSGSGSGTEFTLTISSLQPDDFATYYCQQ YNSYPPTFGGGTKVEIKRTVAAPSVFIFPPSDEQLKSGTASVVCL LNNFYPREAKVQWKVDNALQSGNSQESVTEQDSKDSTYSLSST LTLSKADYEKHKVYACEVTHQGLSSPVTKSFNRGEC | HYB1805's light chain full length sequence |
| 93 | EVQLLESGGGLVQPGGSLRLSCAASGFTFSSYAMSWVRQAPGK GLEWVSAISGSGGSTYYADSVKGRFTISRDNSKNTLYLQMNSLR AEDTAVYYCARLGDGVTYAFDIWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSREEMTKNQVSLTCLVKGFYPSDIAVEWESNGQPENN YKTTPPVLDSDGSFFLYSKLTVDKSRWQQGNVFSCSVMHEALH NHYTQKSLSLSPGK | HYB1806's heavy chain full length sequence |
| 94 | DIQMTQSPSSLSASVGDRVTITCRASQSISSYLNWYQQKPGKAPK LLIYAASSLQSGVPSRFSGSGSGTDFTLTISSLQPEDFATYYCQQS LDFPPITFGGGTKVEIKRTVAAPSVFIFPPSDEQLKSGTASVVCLL NNFYPREAKVQWKVDNALQSGNSQESVTEQDSKDSTYSLSSTL TLSKADYEKHKVYACEVTHQGLSSPVTKSFNRGEC | HYB1806's light chain full length sequence |
| 95 | EVQLLESGGGLVQPGGSLRLSCAASGFTFSSYAMSWVRQAPGK GLEWVSAISGSGGSTYYADSVKGRFTISRDNSKNTLYLQMNSLR AEDTAVYYCARLPSSGSYTAHFDYWGQGTLVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDKK VEPKSCDKTHTCPPCPAPEAAGGPSVFLFPPKPKDTLMISRTPEV TCVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGK | HYB1807's heavy chain full length sequence |
| 96 | DIQMTQSPSSVSASVGDRVTITCRASQGISSWLAWYQQKPGKAP KLLIYAASSLQSGVPSRFSGSGSGTDFTLTISSLQPEDFATYYCQQ GFSFWTFGGGTKVEIKRTVAAPSVFIFPPSDEQLKSGTASVVCLL NNFYPREAKVQWKVDNALQSGNSQESVTEQDSKDSTYSLSSTL TLSKADYEKHKVYACEVTHQGLSSPVTKSFNRGEC | HYB1807's light chain full length sequence |
| 97 | EVQLVESGGGLVQPGRSLRLSCAASGFTFDDYAMHWVRQAPG KGLEWVSGISWNSGSIGYADSVKGRFTISRDNAKNSLYLQMNSL RAEDTAVYYCAREGSSSGYSRHGYDYFDYWGQGTLVTVSSAST KGPSVFPLAPSSKSTSGGTAALGCLVKDYFPEPVTVSWNSGALT SGVHTFPAVLQSSGLYSLSSVVTVPSSSLGTQTYICNVNHKPSNT KVDKKVEPKSCDKTHTCPPCPAPEAAGGPSVFLFPPKPKDTLMIS RTPEVTCVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWES | HYB1808's heavy chain full length sequence |

TABLE A-continued

Overview of Amino Acid Sequences

| SEQ ID NO | Sequence | Description |
|---|---|---|
| | NGQPENNYKTTPPVLDSDGSFFLYSKLTVDKSRWQQGNVFSCS VMHEALHNHYTQKSLSLSPGK | |
| 98 | DIQMTQSPSTLSASVGDRVTITCRASQSISSWLAWYQQKPGKAP KLLIYDASSLESGVPSRFSGSGSGTEFTLTISSLQPDDFATYYCQQ YRSYPITFGGGTKVEIKRTVAAPSVFIFPPSDEQLKSGTASVVCLL NNFYPREAKVQWKVDNALQSGNSQESVTEQDSKDSTYSLSSTL TLSKADYEKHKVYACEVTHQGLSSPVTKSFNRGEC | HYB1808's light chain full length sequence |
| 99 | EPKSCDKTHTCPPCPAPELLGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPQ VYTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK | Human IgG1 Fc domain sequence |
| 100 | EPKSADKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSREEMTKNQVSLTCLVKGFYPSDIAVEWESNGQPENN YKTTPPVLDSDGSFFLYSKLTVDKSRWQQGNVFSCSVMHEALH NHYTQKSLSLSPGK | Human IgG1 Fc domain sequence comprising $C_{220}A/L_{234}A/L_{235}A$ mutations |
| 101 | QLQLVESGGGLVQPGGSLRLSCAASGFTFSNFNMKWYRQVSGK ERELVASIISSGGTTGYADSVKGRFTISRDNAKNTVYLQMNSLK TEDTAVYYCNARRRDSEDYWGQGTQVTVSSEPKSADKTHTCPP CPAPEAAGGPSVFLFPPKPKDTLMISRTPEVTCVVVDVSHEDPEV KFNWYVDGVEVHNAKTKPREEQYNSTYRVVSVLTVLHQDWLN GKEYKCKVSNKALPAPIEKTISKAKGQPREPQVYTLPPSREEMT KNQVSLTCLVKGFYPSDIAVEWESNGQPENNYKTTPPVLDSDGS FFLYSKLTVDKSRWQQGNVFSCSVMHEALHNHYTQKSLSLSPG K | HYB1901's full length sequence |
| 102 | QVQLVESGGGLVQPGGSLRLSCAASGSFFRSIAMAWYRQAPGK QRVLVGTITSDGDTNYADSVKGRFTISRDNAKNTMYLQMNSLK PEDTAVYSCNVPGSIGYWSQGTQVTVSSEPKSADKTHTCPPCPA PEAAGGPSVFLFPPKPKDTLMISRTPEVTCVVVDVSHEDPEVKFN WYVDGVEVHNAKTKPREEQYNSTYRVVSVLTVLHQDWLNGK EYKCKVSNKALPAPIEKTISKAKGQPREPQVYTLPPSREEMTKN QVSLTCLVKGFYPSDIAVEWESNGQPENNYKTTPPVLDSDGSFF LYSKLTVDKSRWQQGNVFSCSVMHEALHNHYTQKSLSLSPGK | HYB1902's full length sequence |
| 103 | QVQLVESGGGLVQAGGSLRLSCAASGRTLSSYAMGWFRQAPG KEREFVASIGRSTYYADPVKGRFTISRDNAKNTVYLQMNSLKSE DTAVYYCNAPIVAGFGTVVSGEYWGQGTQVTVSSEPKSADKTH TCPPCPAPEAAGGPSVFLFPPKPKDTLMISRTPEVTCVVVDVSHE DPEVKFNWYVDGVEVHNAKTKPREEQYNSTYRVVSVLTVLHQ DWLNGKEYKCKVSNKALPAPIEKTISKAKGQPREPQVYTLPPSR EEMTKNQVSLTCLVKGFYPSDIAVEWESNGQPENNYKTTPPVL DSDGSFFLYSKLTVDKSRWQQGNVFSCSVMHEALHNHYTQKSL SLSPGK | HYB1903's full length sequence |
| 104 | QVQLVESGGGLVQPGESLTLSCTVSGSIGNIYDLGWYRQASGKQ RELVASITSGGRTIYADSVEGRFTISRNNAKNTVVLQMNSLEPED MAVYYCNLGHELGYWGQGTQVTVSSEPKSADKTHTCPPCPAPE AAGGPSVFLFPPKPKDTLMISRTPEVTCVVVDVSHEDPEVKFNW YVDGVEVHNAKTKPREEQYNSTYRVVSVLTVLHQDWLNGKEY KCKVSNKALPAPIEKTISKAKGQPREPQVYTLPPSREEMTKNQV SLTCLVKGFYPSDIAVEWESNGQPENNYKTTPPVLDSDGSFFLYS KLTVDKSRWQQGNVFSCSVMHEALHNHYTQKSLSLSPGK | HYB1904's full length sequence |
| 105 | QLQLVESGGGLVQPGGSLRLSCVASGFTFSTYAMAWYRQRPGK ERELVASIDTSGDNTHYVGAVKGRFTISRDNAKNTVYLQMNGL KPEDTAVYFCNAPNTGWGTRRYWGQGTQVTVSSEPKSADKTH TCPPCPAPEAAGGPSVFLFPPKPKDTLMISRTPEVTCVVVDVSHE DPEVKFNWYVDGVEVHNAKTKPREEQYNSTYRVVSVLTVLHQ DWLNGKEYKCKVSNKALPAPIEKTISKAKGQPREPQVYTLPPSR EEMTKNQVSLTCLVKGFYPSDIAVEWESNGQPENNYKTTPPVL DSDGSFFLYSKLTVDKSRWQQGNVFSCSVMHEALHNHYTQKSL SLSPGK | HYB1905's full length sequence |
| 106 | QLQLVESGGGLVQPGGSLRLSCVASGFAFSTYAMAWYRQRPGK ERELVGSIDSSGDNTHYVDAVKGRFTISRDNAKNTVYLQMNVL KPEDTAVYYCNSPNTGWGTRRYWGQGTQVTVSSEPKSADKTH | HYB1906's full length sequence |

TABLE A-continued

Overview of Amino Acid Sequences

| SEQ ID NO | Sequence | Description |
|---|---|---|
| | TCPPCPAPEAAGGPSVFLFPPKPKDTLMISRTPEVTCVVVDVSHE DPEVKFNWYVDGVEVHNAKTKPREEQYNSTYRVVSVLTVLHQ DWLNGKEYKCKVSNKALPAPIEKTISKAKGQPREPQVYTLPPSR EEMTKNQVSLTCLVKGFYPSDIAVEWESNGQPENNYKTTPPVL DSDGSFFLYSKLTVDKSRWQQGNVFSCSVMHEALHNHYTQKSL SLSPGK | |
| 107 | QLQLVESGGGLVQPGGSLRLSCAASGFTFSSYAMAWYRQRSGK ERELVASIDSSGYNTHYTDAGKGRFTISRDNAKNTVYLQMNNL KPEDTAVYYCNAPNTGWGSRRYWGQGTQVTVSSEPKSADKTH TCPPCPAPEAAGGPSVFLFPPKPKDTLMISRTPEVTCVVVDVSHE DPEVKFNWYVDGVEVHNAKTKPREEQYNSTYRVVSVLTVLHQ DWLNGKEYKCKVSNKALPAPIEKTISKAKGQPREPQVYTLPPSR EEMTKNQVSLTCLVKGFYPSDIAVEWESNGQPENNYKTTPPVL DSDGSFFLYSKLTVDKSRWQQGNVFSCSVMHEALHNHYTQKSL SLSPGK | HYB1907's full length sequence |
| 108 | QVQLVESGGGLVQPGESLRLSCSVSGNIGHIYDLGWYRQASGK QRELVASITDNGRTIYGDSVKGRFTISRNNVKNTVNLQMNSLTP EDTAVYYCNLGHWLGYWGQGTQVTVSSEPKSADKTHTCPPCP APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSREEMTK NQVSLTCLVKGFYPSDIAVEWESNGQPENNYKTTPPVLDSDGSF FLYSKLTVDKSRWQQGNVFSCSVMHEALHNHYTQKSLSLSPGK | HYB1908's full length sequence |
| 109 | QVQLLESGGGLVQAGGSLRLSCAASGRTLSSYAMGWFRQAPGK GLEFVASIGRSTYYADPVKGRFTISRDNSKNTVYLQMNSLRAED TAVYYCNAPIVAGFGTVVSGEYWGQGTLVTVSSEPKSADKTHT CPPCPAPEAAGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSRE EMTKNQVSLTCLVKGFYPSDIAVEWESNGQPENNYKTTPPVLDS DGSFFLYSKLTVDKSRWQQGNVFSCSVMHEALHNHYTQKSLSL SPGK | HYB1903-hz1's full length sequence |
| 110 | QVQLLESGGGLVQPGGSLRLSCAASGRTLSSYAMGWFRQAPGK GLEFVASIGRSTYYADPVKGRFTISRDNSKNTVYLQMNSLRAED TAVYYCNAPIVAGFGTVVSGEYWGQGTLVTVSSEPKSADKTHT CPPCPAPEAAGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSRE EMTKNQVSLTCLVKGFYPSDIAVEWESNGQPENNYKTTPPVLDS DGSFFLYSKLTVDKSRWQQGNVFSCSVMHEALHNHYTQKSLSL SPGK | HYB1903-hz2's full length sequence |
| 111 | EVQLLESGGGLVQPGGSLRLSCAASGRTLSSYAMGWFRQAPGK GLEFVASIGRSTYYADPVKGRFTISRDNSKNTVYLQMNSLRAED TAVYYCNAPIVAGFGTVVSGEYWGQGTLVTVSSEPKSADKTHT CPPCPAPEAAGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSRE EMTKNQVSLTCLVKGFYPSDIAVEWESNGQPENNYKTTPPVLDS DGSFFLYSKLTVDKSRWQQGNVFSCSVMHEALHNHYTQKSLSL SPGK | HYB1903-hz3's full length sequence |
| 112 | QVQLLESGGGLVQPGGSLRLSCAASGRTLSSYAMGWFRQAPGK GLEFVASIGRSTYYADSVKGRFTISRDNSKNTVYLQMNSLRAED TAVYYCNAPIVAGFGTVVSGEYWGQGTLVTVSSEPKSADKTHT CPPCPAPEAAGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSRE EMTKNQVSLTCLVKGFYPSDIAVEWESNGQPENNYKTTPPVLDS DGSFFLYSKLTVDKSRWQQGNVFSCSVMHEALHNHYTQKSLSL SPGK | HYB1903-hz4's full length sequence |

TABLE A-continued

| SEQ ID NO | Sequence | Description |
|---|---|---|
| | Overview of Amino Acid Sequences | |
| 113 | QVQLLESGGGLVQPGGSLRLSCAASGRTLSSYAMGWFRQAPGK GLEFVASIGRSTYYADPVKGRFTISRDNSKNTVYLQMNSLRAED TAVYYCAAPIVAGFGTVVSGEYWGQGTLVTVSSEPKSADKTHT CPPCPAPEAAGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSRE EMTKNQVSLTCLVKGFYPSDIAVEWESNGQPENNYKTTPPVLDS DGSFFLYSKLTVDKSRWQQGNVFSCSVMHEALHNHYTQKSLSL SPGK | HYB1903-hz5's full length sequence |
| 114 | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKVEPKSCDKTHTCPPCPAPEAAGGPSVFLFPPKPKDT LYITREPEVTCVVVDVSHEDPEVKFNWYVDGVEVHNAKTKPRE EQYNSTYRVVSVLTVLHQDWLNGKEYKCKVSNKALPAPIEKTIS KAKGQPREPQVYTLPPSREEMTKNQVSLTCLVKGFYPSDIAVEW ESNGQPENNYKTTPPVLDSDGSFFLYSKLTVDKSRWQQGNVFSC SVMHEALHNHYTQKSLSLSPG | Human IgG1 heavy chain constant domain sequence comprising $L_{234}A/L_{235}A/M_{252}Y/S_{254}T/T_{256}E/K_{447}del$ mutations |
| 115 | QVQLVESGGGVVQPGRSLRLSCAASGFTFSSYAMHWVRQAPGK GLEWVAVISYDGSNKYYADSVKGRFTISRDNSKNTLYLQMNSL RAEDTAVYYCARGQVAILDYFDYWGQGTLVTVSSASTKGPSVF PLAPSSKSTSGGTAALGCLVKDYFPEPVTVSWNSGALTSGVHTF PAVLQSSGLYSLSSVVTVPSSSLGTQTYICNVNHKPSNTKVDKK VEPKSCDKTHTCPPCPAPEAAGGPSVFLFPPKPKDTLYITREPEV TCVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGGGGGSGGGGSGGGGSEVQLLESGGGLVQ PGGSLRLSCAASGRTLSSYAMGWFRQAPGKGLEFVASIGRSTYY ADPVKGRFTISRDNSKNTVYLQMNSLRAEDTAVYYCNAPIVAG FGTVVSGEYWGQGTLVTVSSA | HYB1805-2's heavy chain full length sequence |
| 116 | QVQLVESGGGVVQPGRSLRLSCAASGFTFSSYAMHWVRQAPGK GLEWVAVISYDGSNKYYADSVKGRFTISRDNSKNTLYLQMNSL RAEDTAVYYCARGQVAILDYFDYWGQGTLVTVSSASTKGPSVF PLAPSSKSTSGGTAALGCLVKDYFPEPVTVSWNSGALTSGVHTF PAVLQSSGLYSLSSVVTVPSSSLGTQTYICNVNHKPSNTKVDKK VEPKSCDKTHTCPPCPAPEAAGGPSVFLFPPKPKDTLYITREPEV TCVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGGGGGSGGGGSGGGGSGGGGSEVQLLESG GGLVQPGGSLRLSCAASGRTLSSYAMGWFRQAPGKGLEFVASI GRSTYYADPVKGRFTISRDNSKNTVYLQMNSLRAEDTAVYYCN APIVAGFGTVVSGEYWGQGTLVTVSSA | HYB1805-3's heavy chain full length sequence |
| 117 | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKV | Human IgG1 CH1 domain sequence |
| 118 | EPKSCDKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSREEMTKNQVSLTCLVKGFYPSDIAVEWESNGQPENN YKTTPPVLDSDGSFFLYSKLTVDKSRWQQGNVFSCSVMHEALH NHYTQKSLSLSPGK | Human IgG1 Fc domain sequence comprising $L_{234}A/L_{235}A$ mutations |
| 119 | EPKSCDKTHTCPPCPAPEAAGGPSVFLFPPKPKDTLYITREPEVTC VVVDVSHEDPEVKFNWYVDGVEVHNAKTKPREEQYNSTYRVV SVLTVLHQDWLNGKEYKCKVSNKALPAPIEKTISKAKGQPREPQ VYTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG | Human IgG1 Fc domain sequence comprising $L_{234}A/L_{235}A/M_{252}Y/S_{254}T/T_{256}E/K_{447}del$ mutations |

EXAMPLES

The present disclosure generally described herein can be more easily understood by referring to the following examples. Those skilled in the art can draw on the content herein and appropriately improve the process parameters for implementation. It should be particularly pointed out that all similar replacements and modifications are obvious to those skilled in the art, and are all considered within the scope of protection of this disclosure. The following examples are provided for illustrative purposes only and are not intended to limit the disclosure. These examples are not intended to indicate that the experiments described below are the only ones conducted or all the experiments performed.

Unless otherwise specified, the experimental methods used in the following examples are conventional methods. Unless otherwise specified, all the materials, reagents, and the like used in the following examples are commercially available.

Example 1: Screening of Anti-TL1A Antibodies

TL1A antigen (TL1A-his-avi, Beijing ACROBiosystems, TLA-H52Q1, in trimeric form) was loaded onto magnetic beads coupled with streptavidin (Thermo Scientific, 88817) to pan a full human Fab phage display library. The panning processes and results are shown in Table 1. After three rounds of panning, the eluted phages in the TL1A antigen group were significantly enriched compared to the control group, with an enrichment factor of 27.1 times.

TABLE 1

Phage Library Panning Data

| Round | Experimental Group | Beads and Loaded Protein | Input Phage Volume (cfu) | Washing Conditions | Eluted Phage Volume (cfu) | Enrichment Factor Compared to Control Group |
|---|---|---|---|---|---|---|
| 1st | Antigen Group | 100 μL beads loaded with 4 μg TL1A-His-avi | $6 \times 10^{12}$ 2 mL | 0.1% PBST, 16 rpm 1 min × 6 | $1.1 \times 10^7$ | / |
| 2nd | Antigen Group | 100 μL beads loaded with 4 μg TL1A-His-avi | $2 \times 10^{12}$ 1 mL | 0.1% PBST, 16 rpm 2 min × 8 | $4.5 \times 10^7$ | / |
| 3rd | Antigen Group | 100 μL beads loaded with 4 μg TL1A-His-avi | $2 \times 10^9$ 1 mL | 0.1% PBST, 16 rpm 3 min × 8 | $1.15 \times 10^6$ | 27.1 |
| | Control Group | 100 μL beads added with incubation buffer (PBT) only | $2 \times 10^9$ 1 mL | | $4.25 \times 10^4$ | |

Example 2: Screening of Binding Based on Periplasmic Anti-TL1A-Fab Fragment Crude Extracts of the Monoclonal Clones The enriched phage elution library obtained from the third round of panning in Example 1 was used to infect TG1 bacteria in the logarithmic growth phase. After dilution, the bacteria were plated. Monoclonal colonies were then picked and inoculated into a 96-well deep-well bacterial culture plate containing 1 mL/well of 2×YT medium (with 1‰ Amp) for overnight incubation at 28° C.

On the second day, the plate was centrifuged at 4200 rpm for 30 minutes at 4° C. The bacterial pellet was resuspended in 0.3 mL PBST. Three freeze-thaw cycles between −80° C. and 37° C. were performed to release the Fab fragments from the periplasmic space. After another centrifugation at 4200 rpm for 30 minutes at 4° C., 200 μL of the supernatant was transferred to a 96-well sample plate to prepare the periplasmic anti-TL1A-Fab fragment crude extracts of the monoclonal clones.

Next, ELISA binding assay was performed for the crude extract. Wells coated with TL1A-His protein (ACROBiosystems, TLA-H5243, in trimeric form) were used as test wells, while wells coated with an unrelated target protein were used as control wells. Anti-HA tag antibody conjugated with horseradish peroxidase (HRP) (Sino Biological, 100028-MM10-H) was used as the secondary antibody. Corresponding bacterial of clones with an $OD_{450nm}$ readings above 1.0 in the test wells and below 0.1 in the control wells were selected for plasmid extraction and gene sequencing. After translating the DNA sequences obtained from sequencing into amino acid sequences, sequence alignment was performed. Repeated sequences and similar sequences with less than 2 amino acid differences in the CDR regions (CDR region was partitioned using the AbM method) were removed. A total of 30 unique sequences were obtained eventually.

Example 3: Blocking Function Assay Based on Periplasmic Anti-TL1A-Fab Fragment Crude Extracts Human DR3/TNFRSF25 (with a his tag, ACROBiosystems, TN5-H52H3) was coated on an ELISA plate overnight at 4° C. at a concentration of 300 ng per well. On the second day, the ELISA plate was blocked with 1% BSA (bovine serum albumin) for 2 hours at room temperature. The crude extracts were mixed with TL1A-his-avi at a concentration of 0.8 μg/mL in equal volumes. The crude extracts were prepared from the stock solution and diluted in a 1:2 gradient. Two concentration points were set: stock solution (1×) and 1:2 (0.5×) After incubation at room temperature for 30 minutes, the crude extracts and TL1A-his-avi were transferred to the blocked wells coated with DR3 and incubated for 1 hour at room temperature. The plate was washed after the incubation; and detected by the addition of streptavidin-HRP (ACROBiosystems, STN-NH913) at a ratio of 1:3000. PRA-023 was used as a positive reference (refers to patent US2022/0259320A1 for sequence, initial concentration of 100 nM), and crude extracts of Fab fragments targeting an unrelated target were used as a negative control. The absorbance at 450 nm wavelength was read using a microplate reader (Biotek, Synergy H1MF).

As shown in FIG. 1, among the 30 unique sequence clones, 8 clones (numbered 4, 5, 8, 9, 11, 12, 24, and 30 respectively) exhibited a certain blocking efficacy against TL1A-DR3.

Example 4: Expression and In Vitro Activity Assay of Anti-TL1A Antibodies

The Fab fragment sequences corresponding to clones 4, 5, 8, 9, 11, 12, 24, and 30 (their heavy chain variable domain and light chain variable domain sequences are as shown in SEQ ID NOs: 7, and 8; SEQ ID NOs: 14, and 15; SEQ ID NOs: 20, and 21; SEQ ID NOs: 24, and 25; SEQ ID NOs: 30, and 31; SEQ ID NOs: 34, and 35; SEQ ID NOs: 38, and 39; and SEQ ID NOs: 42, and 43, respectively) were linked to the N-terminus of the human IgG1 Fc domain (containing $L_{234}A/L_{235}A$ mutations), and were transiently transfected into HEK293 cells for expression and purification. The resulting molecules were named as HYB1801 to HYB1808, respectively.

Then, TF-1 cells were used to test the inhibitory efficacy of the expressed anti-TL1A antibodies on the TL1A-mediated caspase3/7 apoptosis signaling pathway. GM-CSF-free RPMI 1640 medium (containing 10% FBS) was used to dilute the anti-TL1A antibody samples in a gradient. Cycloheximide (CHX) was prepared at a concentration of 80 μg/mL, and TL1A-His (ACROBiosystems, TLA-H5243, in trimeric form) was prepared at a concentration of 40 ng/mL. Then, 30 μL each of the antibody dilution, CHX solution, and TL1A solution were added to a sterile 96-well plate and incubated at 37° C. in a cell culture incubator for 1 hour. Meanwhile, TF-1 cells in the logarithmic growth phase were inoculated into a 96-well white-walled transparent-bottom cell culture plate at a density of 30,000 cells/50 μL/well. The incubated antibody:CHX:TL1A mixture solution was added to the cell culture plate at 50 μL/well and incubated in the cell culture incubator for 6 hours. After the incubation, 100 μL/well of Caspase-Glo®3/7 reagent (Promega, G8091) was added, and luminescence detection was performed according to the reagent instructions.

Figure 2:
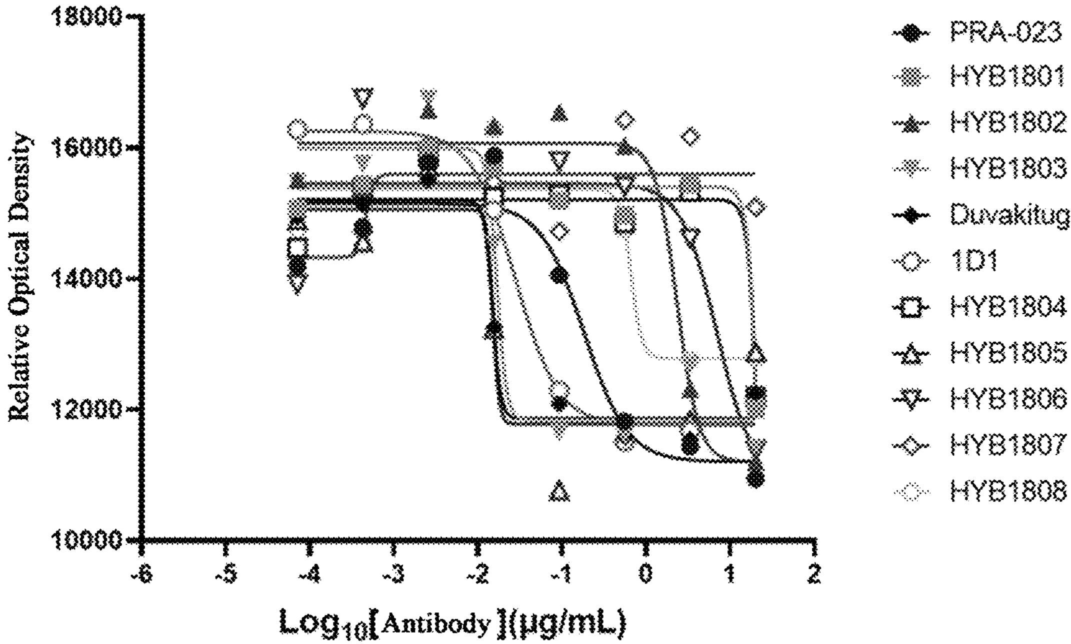
FIG. 2: Assay results of inhibition effects of anti-TL1A IgG antibodies on TL1A-mediated caspase 3/7 apoptosis signaling pathway in TF-1 cells, with single replicate wells.

As shown in FIG. 2, HYB1803 and HYB1805 exhibited a similar blocking efficacy to the reference molecule Duvakitug (refers to patent US2016/0333104A1 for sequence) and were superior to another reference molecule 1D1 (or RVT-3101, refers to U.S. Pat. No. 9,683,998B2 for sequence), and were significantly superior to PRA-023. Therefore, HYB1803 and HYB1805 were selected for further studies. In the previous transient transfection and expression purification in HEK293 cells, after one-step purification with Protein A, the yield and SEC monomer purity of HYB1803 and HYB1805 were 165 mg/L, 99.49% and 421 mg/L, 100%, respectively.

Example 5: Blocking Activity Assay of Anti-TL1A Antibodies on TL1A-DR3

The blocking ELISA assay of anti-TL1A antibodies on TL1A-DR3 binding was performed as described in Example 3, with 1D1, PRA-023, and Duvakitug used as positive controls.

Figure 3:
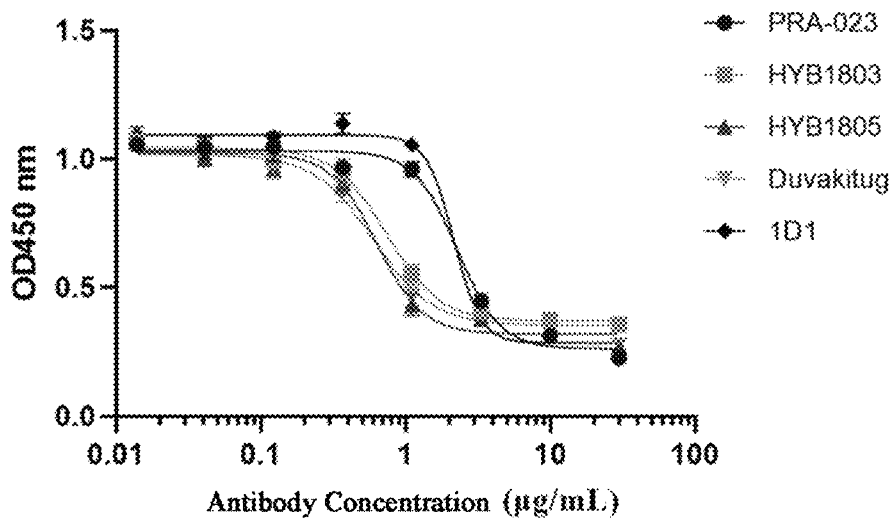
FIG. 3: Blocking ELISA assay results of anti-TL1A IgG antibodies on the binding of TL1A-DR3, with double replicate wells.

As shown in FIG. 3, HYB1803 and HYB1805 exhibited a similar blocking efficacy to the reference molecule Duvakitug and were superior to the other two reference molecules 1D1 and PRA-023.

Example 6: Binding Activity Study of Anti-TL1A Antibodies to *Macaca fascicularis* TL1A

Figure 4:
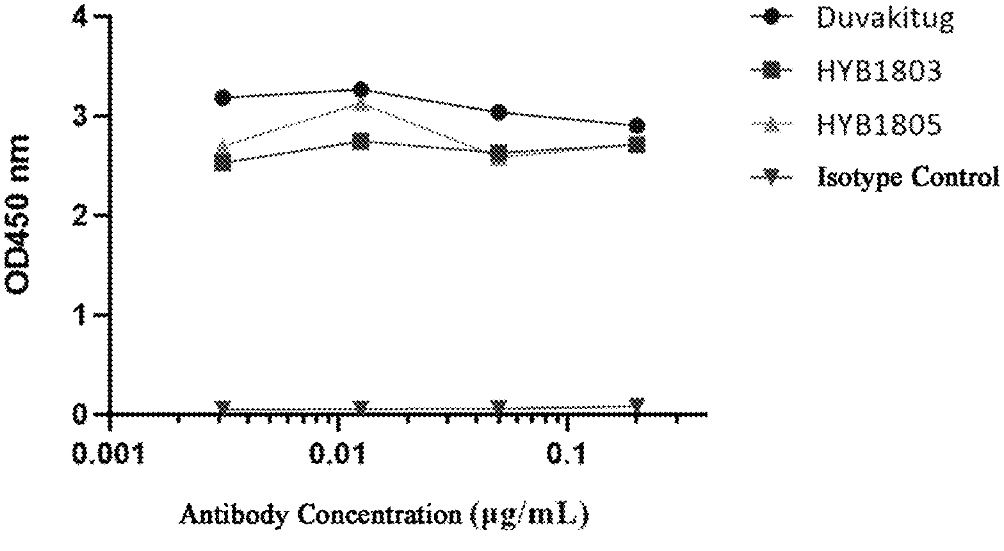
FIG. 4: Binding ELISA assay results of anti-TL1A IgG antibodies on the binding of *Macaca fascicularis* TL1A.

*Macaca fascicularis* TL1A protein (ACROBiosystems, TLA-C5241) was coated on an ELISA plate at 200 ng per well. Gradient-diluted anti-TL1A antibodies were added and incubated. The initial concentration of the anti-TL1A antibodies was 0.2 μg/mL, and a 1:4 gradient dilution was performed. Four concentration points were set (0.2, 0.05, 0.0125, and 0.003125 μg/mL). The plate was detected with anti-human Fc secondary antibody conjugated with HRP. As shown in FIG. 4, HYB1803 and HYB1805 exhibited a strong binding ability to *Macaca fascicularis* TL1A, similar to the reference molecule Duvakitug.

Example 7: Blocking Activity Assay of Anti-TL1A Antibodies on TL1A-DcR3

DcR3 and DR3 are two receptors of TL1A, both belonging to the TNF receptor superfamily. Unlike DR3, DcR3 exists in a soluble form in the body, does not have a transmembrane domain (Yu, K-Y. et al. (1999) J. Biochem. Chem. 274:13733), does not transmit signals into the cell, acts as a decoy receptor (Wroblewski V-J. et al. (2003) Biochem. Pharmacol. 65:657), and negatively regulates the TLTA-DR3 signaling pathway. Therefore, the development of therapeutic agents with a selective blocking activity against TLTA-DR3 is expected to exhibit a better activity and a clinical development potential.

To test the blocking efficacy of anti-TL1A antibodies on TL1A-DcR3, DcR3-Fc (Sino Biological, 10224-H02B) was coated on an ELISA plate at 200 ng per well. Gradient-diluted anti-TL1A antibodies were mixed with TL1A-His-avi at a concentration of 40 ng/mL in equal volumes, incubated at room temperature for 30 minutes, and then added to the plate. The plate was shaken and incubated at room temperature for 1 hour. The plate was washed after the incubation and detected with streptavidin-HRP.

Figures 5, 6:
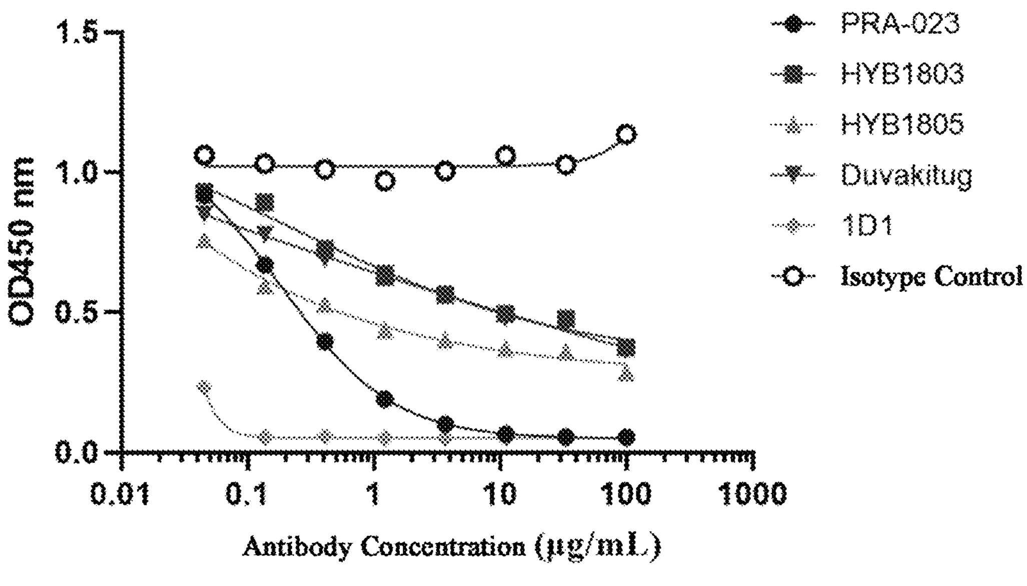
FIG. 5: Blocking ELISA assay results of anti-TL1A IgG antibodies on the binding of TL1A-DcR3, with single replicate wells.
FIG. 6: Assay results of inhibition of signaling pathway based on huTL1A/CHO cells and DR3 reporter gene cells, with double replicate wells except for 1D1 being single replicate wells.

As shown in FIG. 5, HYB1803, HYB1805, and the reference molecule Duvakitug did not completely block TL1A-DcR3, even at a concentration of 100 μg/mL. The reference molecule PRA-023 had normal blocking activity against TL1A-DcR3, with an $EC_{50}$ value of approximately 0.2 μg/mL. The reference molecule 1D1 exhibited the strongest blocking activity against TL1A-DcR3.

Example 8: Affinity ($K_D$) Measurement

The affinities of HYB1803 and HYB1805 against TL1A protein (ACROBiosystems, TLA-H5243, in trimeric form) were measured using Biacore 8K. The test antibodies were captured on a Protein A chip (Cytiva, 29127556) at a flow rate of 10 μL/min, and then different concentrations of antigen protein were flowed in at a flow rate of 30 μL/min. The running buffer was HBS-$EP^+$, and the association time of the antigen with the antibody was 120 seconds, while the dissociation time was 450 seconds. The regeneration buffer was 10 mM pH 1.5 Gly-HCl. After the detection, the built-in software of the instrument was used to fit the data according to the 1:1 binding model to calculate the association rate constant Kon, dissociation rate constant $K_{off}$, and equilibrium dissociation constant $K_D$ values of the antibody-antigen binding. The results are shown in Table 2.

TABLE 2

Affinity Measurement Data

| Antibody | $K_{on}$ (1/MS) | $K_{off}$ (1/S) | $K_D$ (M) |
|---|---|---|---|
| HYB1803 | $6.17 \times 10^{6}$ | $9.69 \times 10^{-5}$ | $1.57 \times 10^{-11}$ |
| HYB1805 | $2.32 \times 10^{6}$ | $7.48 \times 10^{-5}$ | $3.23 \times 10^{-11}$ |

Example 9: Assay Based on TL1A/CHO Cells and DR3 Reporter Gene Cells

In epithelial cells, membrane-bound TL1A can bind to and activate its functional receptor through cell-cell contact, thereby enhancing the secretion of downstream inflammatory factors, including interferon. Anti-TL1A antibodies designed for the treatment of inflammatory and/or autoimmune diseases should be verified to block both endogenous forms of TL1A to achieve best therapeutic effects.

To test the blocking efficacy of anti-TL1A antibodies against membrane-bound TL1A, this example used CHO cells stably expressing human TL1A on the membrane surface and reporter gene cells stably expressing human DR3.

The assay method is as follows: 20,000 huTL1A/CHO cells per well, 40,000 DR3 reporter gene cells per well, and 100 μL gradient-diluted test antibodies per well were added to a white-walled transparent-bottom cell culture plate. The culture medium used was RPMI 1640 medium containing 10% FBS, and the plate was incubated in a 37° C. incubator for 6 hours. After the incubation, 100 μL per well of a fluorescent detection reagent (Cobioer, CBPH0001) was added to each well for fluorescence detection.

As shown in FIG. 6, HYB1805 and Duvakitug exhibited a superior blocking efficacy against the fluorescent signal, followed by HYB1803, all of which were better than 1D1 and significantly better than PRA-023.

Example 10: Preparation and Screening of Single-Domain Antibodies Targeting IL-23p19 (IL-23A)

Vaccination of Alpacas

Human IL-23A-huFc protein (purchased from Sino Biological, 13062-$H_{02}$H) and IL23A&IL12B-His protein (heterodimer, purchased from ACROBiosystems, ILB-H52W5) were used for subcutaneous injection to immunize two alpacas. The immunization dose was 0.5 mg per animal per injection. IL-23A-huFc was used in the first two immunizations to preferentially enrich antibodies targeting IL23A, and IL23A&IL12B was used in the third to eighth immunizations. Complete adjuvant was used for the first immunization, and incomplete adjuvant was used for subsequent immunizations, with a 2-week interval between each immunization, for a total of eight immunizations.

Serum Immune Titer Determination

Starting from the second immunization, 5 mL of blood was collected 1 week after each immunization for serum immune titer determination. Specifically, the IL23A&IL12B-His antigen protein used in the previous step was coated on an ELISA plate at 200 ng per well. After blocking and washing, serum samples diluted at a 1:2000 ratio were added. After incubation, binding, and washing, the plate was detected using a secondary antibody of an anti-camelid single-domain antibody (GenScript, A01861).

Phage Display Library Construction

After eight immunizations, 10 mL of blood was collected from each camel and combined to construct a single-domain antibody phage display library. Lymphocytes were first isolated using lymphocyte separation medium (Solarbio, P8610). The lymphocytes were treated and lysed with RNA extraction reagent (TaKaRa, 9109), and impurities were removed with chloroform. RNAs were precipitated with isopropanol and washed with 75% ethanol. After drying at room temperature, the RNAs were dissolved in water for injection. Next, the RNAs were reverse transcribed into cDNAs using a reverse transcription kit (Thermo Scientific, K1622). The DNAs encoding VHH were then amplified by nested PCR, digested with Sfi I, and ligated to the display vector that was also digested with Sfi I using $T_4$ DNA ligase. The ligation product was purified and electroporated into TGT competent cells, which were then infected with M13KO7 helper phage to construct the phage display library. The eventually-constructed libraries (HYC7-8 and HYBC8-8) had effective library capacities of $4\times10^9$ and $4.8\times10^9$ cfu, respectively.

Panning of the Phage Display Library

The antigen (IL23A&IL12B-His-Avi, ACROBiosystems, ILB-H82W6, in heterodimeric form) was loaded onto magnetic beads coupled with streptavidin (Thermo Scientific, 88817) to pan the HYC7-8 and HYBC8-8 phage libraries. The panning processes and results are shown in Table 3. After one round of panning, the eluted phages in the IL23A&IL12B antigen group were significantly enriched compared to the control group, with enrichment factors of 200 times and 405.4 times, respectively.

TABLE 3

Phage Library Panning Data

| Rounds | Experimental Group | Beads and Loaded Protein | Input Phage Volume (cfu) | Washing Conditions | Eluted Phage Volume (cfu) | Enrichment Factor Compared to Control Group |
|---|---|---|---|---|---|---|
| IL23A&IL12B-His-avi Panning Data-Library HYC7-8 | | | | | | |
| 1st | Antigen Group | 100 μL beads loaded with 5 μg IL23A& IL12B-His-Avi | $1 \times 10^{12}$ 1 mL | 0.1% PBST 16 rpm 1 min × 6 | $3 \times 10^8$ | 200 |
| | Control Group | 100 μL beads added with incubation buffer (PBT) only | $1 \times 10^{12}$ 1 mL | | $1.5 \times 10^6$ | |
| IL23A&IL12B-His-avi Panning Data-Library HYC8-8 | | | | | | |
| 1st | Antigen Group | 100 μL beads loaded with 5 μg IL23A& IL12B-His-Avi | $1 \times 10^{12}$ 1 mL | 0.1% PBST 16 rpm 1 min × 6 | $7.5 \times 10^8$ | 405.4 |
| | Control Group | 100 μL beads added with incubation buffer (PBT) only | $1 \times 10^{12}$ 1 mL | | $1.85 \times 10^6$ | |

Monoclonal Phage-Based Screening

The enriched phage library eluted from the previous steps was used to infect TG1 bacteria in the logarithmic growth phase. After dilution, the TG1 bacteria were plated and incubated. Monoclonal colonies were picked and inoculated into 2×YT medium containing Carb and M13KO7 helper phage for overnight incubation. On the second day, the culture plate was centrifuged at 4200 rpm, and the supernatant was collected for phage ELISA assay. The wells coated with IL23A&IL12B-His protein (heterodimer, Beijing Sino Biological, CT012-H08H) were used as the test wells, and the wells coated with unrelated target protein were used as the control wells. Anti-M13 antibody conjugated with HRP (Sino Biological, 11973-MM05T-H) was used as the secondary antibody. Bacterial of clones with $OD_{450nm}$ readings above 1.0 in the test wells and below 0.1 in the control wells were selected for plasmid extraction and gene sequencing. After translating the obtained DNA sequences into amino acid sequences, sequence alignment was performed. Repeated sequences and similar sequences with less than 2 amino acid differences in the CDR regions (CDR region was partitioned using the AbM method) were removed. A total of 103 unique sequences were finally obtained.

Example 11: Blocking Function Assay Based on IL-23p19 Periplasmic Single-Domain Antibody Crude Extracts Plasmids containing unique sequences were transformed into BL21 Rosetta (DE3) competent cells and transferred into 2 mL of 2× YT medium containing Carb antibiotic. When the $OD_{600}$ reached 0.4, 3 mL of 2× YT medium containing IPTG and Carb was added to achieve a final IPTG concentration of 0.1 mM, and the incubation was continued overnight at 28° C. On the second day, the bacterial suspension was centrifuged at 4200 rpm and 4° C. for 20 minutes. The bacterial pellet was then resuspended in 0.5 mL of PBS and subjected to three freeze-thaw cycles between −80° C. and 37° C. to release the single-domain antibodies from the periplasmic space. After centrifugation at 10000 rpm and 4° C. for 15 minutes, the supernatant was collected to prepare the crude extracts of periplasmic single-domain antibodies (10×).

The crude extracts of single-domain antibodies were then used for blocking ELISA assay of the binding between human IL-23R-Fc and IL23A&IL12B-His-Avi. First, human IL-23R-Fc (ACROBiosystems, ILR-H5254) was coated on the plate overnight at 4° C. at a concentration of 300 ng per well. On the second day, the plate was blocked with 1% BSA (bovine serum albumin) at room temperature for 2 hours. The crude extracts were mixed with IL23A&IL12B-His-Avi at a concentration of 0.2 μg/mL in equal volume, and diluted from the stock solution in a 1:2 gradient. Two concentration points were set (the final concentrations of the single-domain antibody crude extract were 5× and 2.5×, respectively). After incubation at room temperature for 30 minutes, the crude extract and IL23A&IL12B-His-Avi mixture were transferred to the blocked plate coated with IL23R-Fc, and incubated at room temperature for 1 hour. The plate was washed after the incubation; and detected by the addition of streptavidin-HRP (Sangon Biotech, D111054) at a ratio of 1:3000. Risankizumab biosimilar was used as the positive control, and single-domain antibody crude extract targeting an unrelated target was used as the negative control. The absorbance at 450 nm was read using a microplate reader (BioTek, Synergy $H_1$MF).

The results showed that among the 103 clones, 8 clones exhibited a significant blocking efficacy against the binding of IL-23R and IL-23. In addition, the binding ability of the crude extracts of said 103 clones to IL-23 coated on the plate was also tested, and it was found that most of them had a significant binding, while they did not bind to the control wells coated with unrelated target proteins (data not shown).

Example 12: Expression and Cross-Species (Cynomolgus) Activity Identification of IL-23p19 Heavy Chain Antibody The $V_H$H sequences of the above-mentioned 8 clones were connected to the N-terminus of the human IgG1 Fc domain (containing $C_{220}A/L_{234}A/L_{235}A$ mutations, with the sequence as shown in SEQ ID NO: 100) and transiently transfected into HEK293 cells for expression and purification. The resulting molecules were named as HYB1901, HYB1902, HYB1903, HYB1904, HYB1905, HYB1906, HYB1907, and HYB1908, respectively (their variable domain sequences are as shown in SEQ ID NOs: 47, 51, 55, 59, 63, 66, 70, and 74, respectively). Then, the binding abilities of these molecules to Cynomolgus IL23A & mouse IL12B-His proteins (ACROBiosystems, ILB-CM52W8) coated on the plate were determined by ELISA, with Risankizumab biosimilar used as the positive control.

Figure 7:
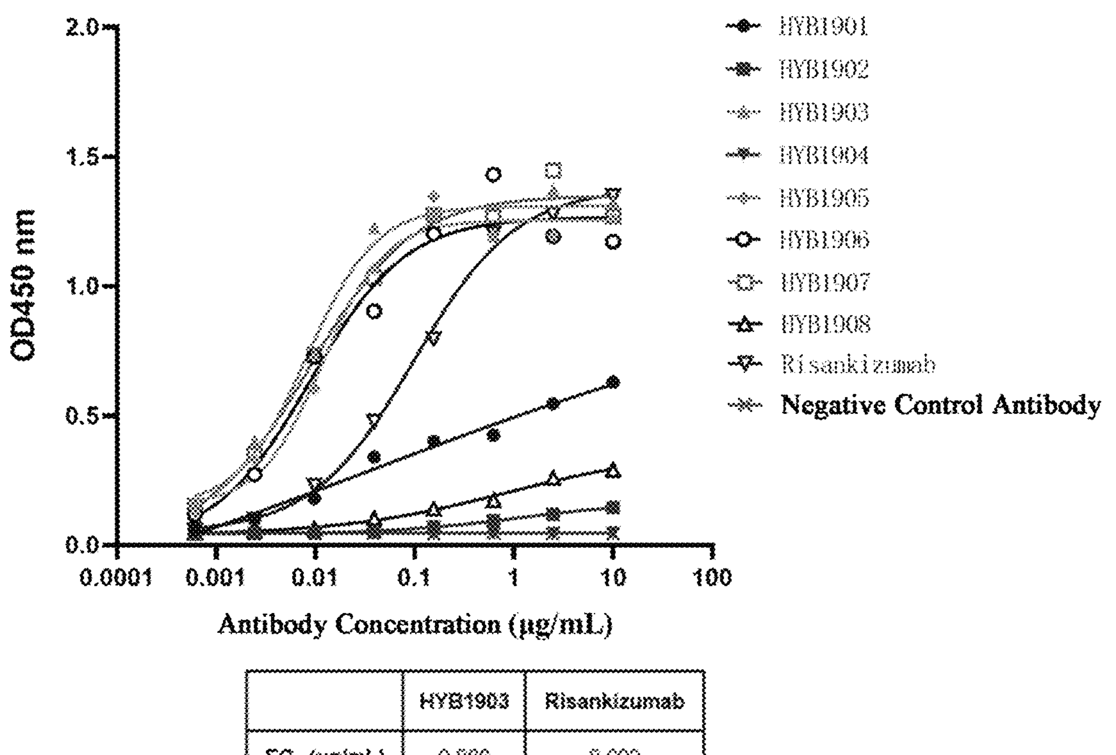
FIG. 7: Binding ELISA assay of anti-IL-23p19 IgG antibodies to the monkey IL-23A & mouse IL-12B heterodimeric antigen protein, with Risankizumab as the positive control.

As shown in FIG. 7, HYB1901, HYB1903, HYB1905, HYB1906, and HYB1907 all had an effective binding to Cynomolgus IL23A & mouse IL12B proteins. These five molecules HYB1901, HYB1903, HYB1905, HYB1906, and HYB1907 were selected for further research.

Example 13: Activity Determination of IL-23p19 Heavy Chain Antibody on Blocking the Binding of IL-23 to IL-23R The blocking ability of IL-23p19 heavy chain antibody against the binding of IL-23-Avi to IL-23R-Fc was detected according to the method described in Example 11, with Risankizumab biosimilar as the positive control and isotype single-domain antibody targeting an unrelated target as the negative control.

Figure 8:
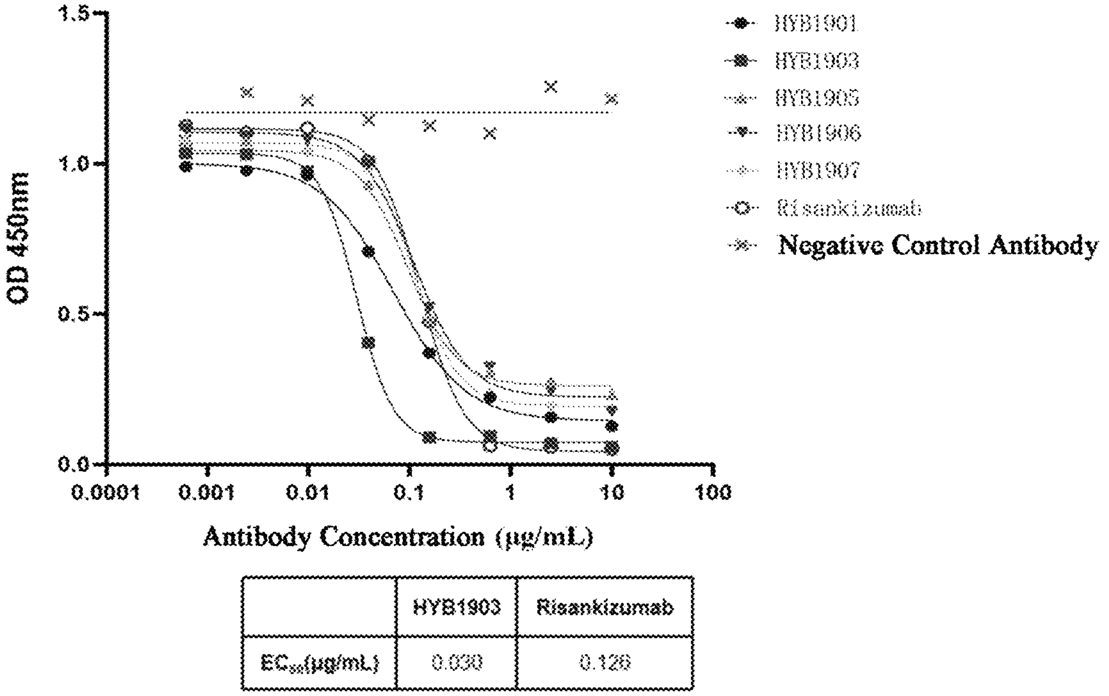
FIG. 8: Blocking efficacy assay of anti-IL-23p19 IgG antibodies on the binding of human IL-23R-Fc to IL-23-Avi. All molecules are observed to exhibit definite blocking effects, wherein HYB1903 has the best blocking efficacy.

As shown in FIG. 8, each molecule exhibited a clear blocking efficacy, with HYB1903 having the best blocking efficacy. Its $EC_{50}$ value was 0.030 μg/mL, which was better than that of the control molecule Risankizumab (0.126 μg/mL).

Example 14: Inhibitory Ability of IL-23p19 Heavy Chain Antibody on IL-23-Induced IL-17A Release from Mouse Spleen Cells Mouse spleen cells (Oribiotech, MSPL-002F) were added at 50,000 cells/100 μL/well in a 96-well cell culture plate and incubated in a 37° C. incubator for 2 hours. During this period, gradient-diluted IL-23p19 heavy chain antibody samples and human IL-23-His (Beijing ACROBiosystems, ILB-H52W5) were mixed in a 1:1 volume (60+60 μL) and incubated at 37° C. for 1 hour. After the cell incubation, 100 μL of the incubated mixture was added to the well of the mouse spleen cells, with the final concentration of human IL-23-His being 10 ng/mL. The cells were then incubated in a 37° C./5% $CO_2$ incubator for 48 hours. After the incubation, the level of mIL-17A secretion in the supernatant was detected using a mIL-17A quantitative kit (BioSharp, BSEM-041-96T).

Figure 9:
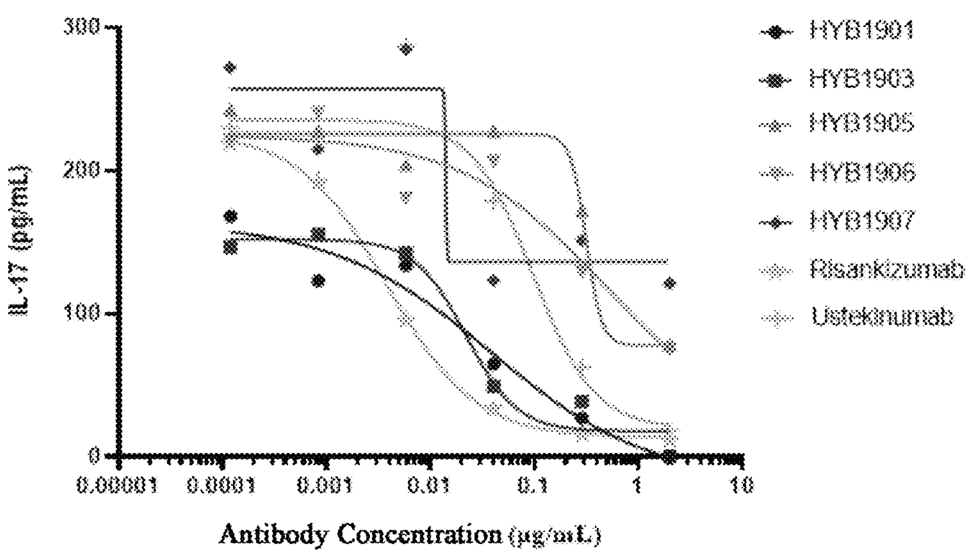
FIG. 9: Inhibition results of anti-IL-23p19 IgG antibodies on the release of mIL-17A in mouse spleen cells induced by human IL-23, with single replicate wells. HYB1903 is observed to exhibit the best inhibitory effect among all candidate molecules.

As shown in FIG. 9, HYB1903 exhibited the best blocking efficacy against IL-23-induced IL-17A release from mouse spleen cells, with a blocking $EC_{50}$ of 0.022 μg/mL.

Example 15: Humanization and Activity Determination of IL-23p19 Heavy Chain Antibody The structure of antibody HYB1903 was modeled using SWISS-MODEL, and the humanization mutations of camelid amino acid sites in the framework were assessed based on the obtained structure. The human germline genes $V_{3-23}$*01 and $J_1$*01 were used as the target sequences for humanization mutations. Amino acid sites located on the surface of the antibody structure and not adjacent to the CDRs were mutated first, while those located inside the antibody structure (buried) and adjacent to the CDRs were mutated later.

Based on the above principles, several humanized antibody sequences were designed: HYB1903-hz1 to HYB1903-hz5 (their variable domain sequences are as shown in SEQ ID NOs: 75-79). Subsequently, these sequences were transiently transfected into HEK293 cells for expression. After expression and purification, it was found that the SEC monomer purity of HYB1903-hz5 was less than 90%, while the purities of the other molecules were above 97%. The blocking efficacies of 1HYB1903-hz1 to HYB1903-hz4 at the cellular level were then tested using the method described in Example 14.

Figure 10:
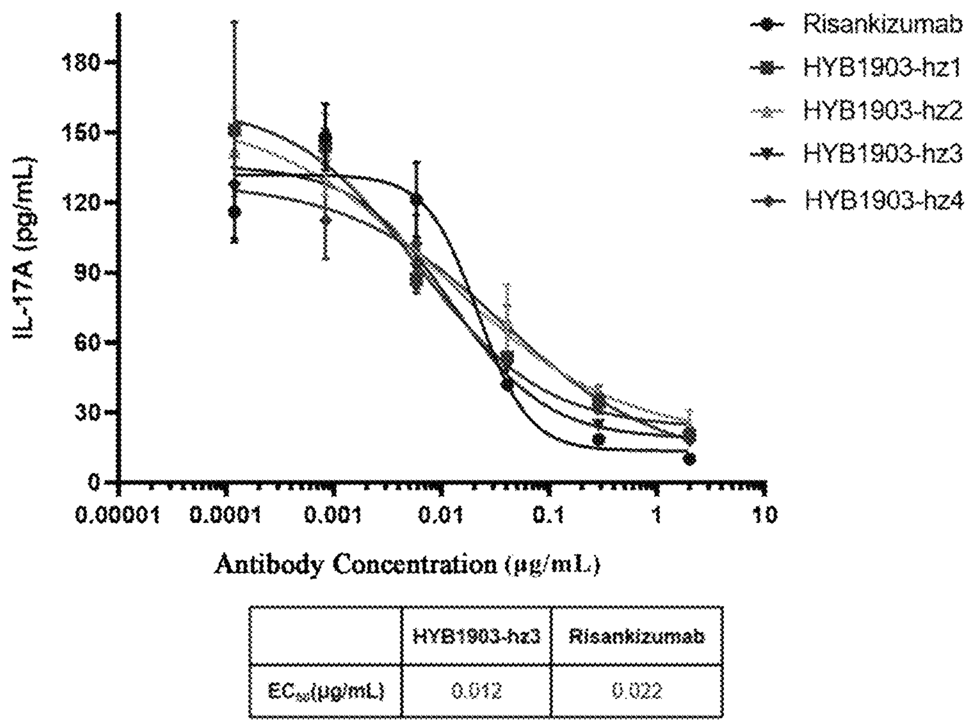
FIG. 10: Inhibition results of humanized anti-IL-23p19 IgG antibodies on the release of mIL-17A in mouse spleen cells induced by human IL-23, with double replicate wells.

As shown in FIG. 10, HYB1903-hz1 to HYB1903-hz4 all exhibited a good blocking efficacy against IL-23-induced IL-17A release from mouse spleen cells, with the blocking efficacy close to that of the positive control Risankizumab.

Example 16: Construction of Bispecific Antibody Targeting TL1A and IL-23p19

The conventional 4-chain antibody molecule HYB1805 screened from a fully human phage display library was used for the portion targeting TL1A, and the single-domain antibody (sdAb) HYB1903-hz3 prepared after llamas immunization and humanization was used for the portion targeting IL-23p19. HYB1903-hz3 was connected to the C-terminus of the heavy chain of HYB1805 via $(GGGGS)_3$ and $(GGGGS)_4$ linkers, respectively. The Fc domain was introduced with $M_{252}Y/S_{254}T/T_{256}E/L_{234}A/L_{235}A/K_{447}$del mutations. The constructed molecules were named as HYB1805-2 and HYB1805-3 respectively (the heavy chain sequences are as shown in SEQ ID NOs: 115 and 116, respectively, and the light chain sequence is as shown in SEQ ID NO: 92). These molecules were transiently transfected and expressed in HEK293 cells, and both molecules had good yield and SEC monomer purity.

Example 17: Inhibitory Efficacy of Bispecific Antibody on IL-23-Induced IL-17A Release from Mouse Spleen Cells Mouse spleen cells (Oribiotech, MSPL-002F) were added at 50,000 cells/100 µL/well in a 96-well cell culture plate and incubated in a 37° C. incubator for 2 hours. During this period, gradient-diluted bispecific antibody samples and human IL-23-His (Beijing ACROBiosystems, ILB-H52W5) were mixed in a 1:1 volume (60+60 µL) and incubated at 37° C. for 1 hour. After the cell incubation, 100 µL of the incubated mixture was added to the well of the mouse spleen cells, with the final concentration of human IL-23-His being 10 ng/mL. The cells were then cultured in a 37° C./5% $CO_2$ incubator for 48 hours. After the incubation, the level of mIL-17A secretion in the supernatant was detected using a mIL-17A quantitative kit (BioSharp, BSEM-041-96T).

Figure 11:
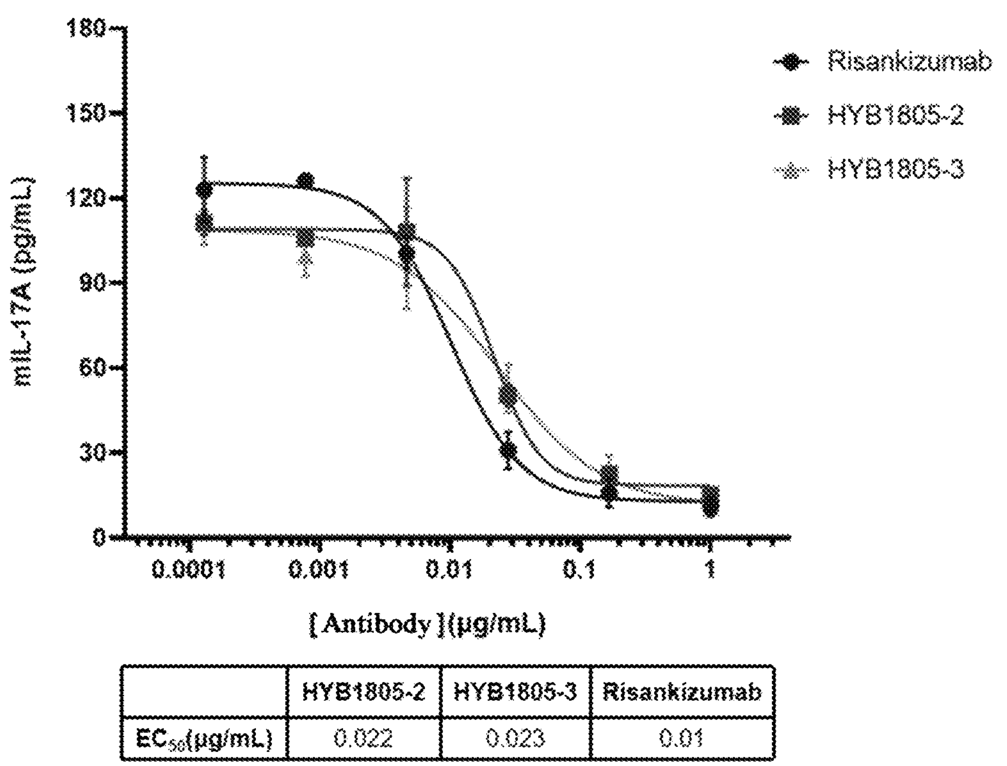
FIG. 11: Inhibition results of bispecific antibodies on the release of mIL-17A in mouse spleen cells induced by human IL-23, with triple replicate wells, using Risankizumab as the positive reference.

As shown in FIG. 11, both bispecific antibody molecules exhibited a good blocking efficacy against IL-23-induced IL-17A release from mouse spleen cells. The bispecific antibody with a shorter linker, HYB1805-2, was selected for further validation.

Example 18: Inhibitory Efficacy of Bispecific Antibody on TL1A-Mediated Caspase3/7 Apoptosis Signaling Pathway The inhibitory efficacy of HYB1805-2 on the TL1A-mediated caspase3/7 apoptosis signaling pathway was tested using TF-1 cells. The bispecific antibody samples were gradient-diluted in GM-CSF-free RPMI 1640 medium (containing 10% FBS). Cycloheximide (CHX) was prepared at a concentration of 80 µg/mL, and TL1A-His (ACROBiosystems, TLA-H5243, in trimeric form) was prepared at a concentration of 40 ng/mL. Then, 30 µL each of the antibody dilution, CHX solution, and TL1A solution were added to a sterile 96-well plate and incubated at 37° C. in a cell culture incubator for 1 hour. Meanwhile, TF-1 cells in the logarithmic growth phase were inoculated into a 96-well white-walled transparent-bottom cell culture plate at a density of 30,000 cells/50 µL/well. The incubated antibody:CHX:TL1A mixture was added to the cell culture plate at 50 µL/well and incubated in the cell culture incubator for 6 hours. After the incubation, 100 µL/well of Caspase-Glo®3/7 reagent (Promega, G8091) was added, and luminescence detection was performed according to the reagent instructions.

Figure 12:
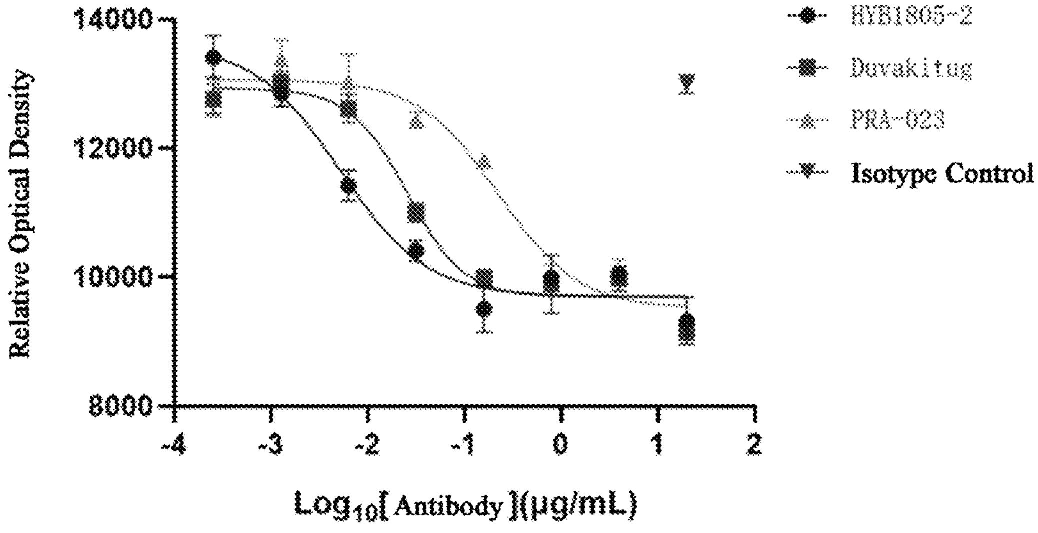
FIG. 12: Assay results of inhibition effects of bispecific antibodies on the TL1A-mediated caspase 3/7 apoptosis signaling pathway in TF-1 cells, with triple replicate wells.

As shown in FIG. 12, HYB1805-2 exhibited a good in vitro blocking efficacy against TL1A, with the blocking efficacy better than that of the control drug Duvakitug and significantly better than that of the control drug PRA-023.

It should be understood that although the disclosure has been illustratively described based on its preferred embodiments, it should not be limited to the above examples. For those skilled in the art, the disclosure may have various modifications and variations. The selection and application of specific technical solutions can be adjusted and changed according to specific needs. Therefore, for those skilled in the art, several simple replacements can still be made without departing from the concepts and principles of the present disclosure, and these should all be included within the scope of protection of the disclosure.

What is claimed is:

1. A bispecific antigen-binding molecule comprising a first antigen-binding functional region and a second antigen-binding functional region, wherein the first antigen-binding functional region comprises at least one antigen-binding unit targeting TL1A comprising an immunoglobulin heavy chain variable domain (VH) and an immunoglobulin light chain variable domain (VL), wherein:

the VH comprises an HCDR1 comprising the amino acid sequence set forth in SEQ ID NO: 26, an HCDR2 comprising the amino acid sequence set forth in SEQ ID NO: 27, and an HCDR3 comprising the amino acid sequence set forth in SEQ ID NO: 28, and the VL comprises an LCDR1 comprising the amino acid sequence set forth in SEQ ID NO: 17, an LCDR2 comprising the amino acid sequence set forth in SEQ ID NO: 18, and an LCDR3 comprising the amino acid sequence set forth in SEQ ID NO: 29;

and the second antigen-binding functional region comprises at least one immunoglobulin single variable domain specifically binding to IL-23p19 comprising:

a CDR1 comprising the amino acid sequence set forth in SEQ ID NO: 52, a CDR2 comprising the amino acid sequence set forth in SEQ ID NO: 53, and a CDR3 comprising the amino acid sequence set forth in SEQ ID NO: 54.

2. The bispecific antigen-binding molecule according to claim 1, comprising a first antigen-binding functional region and a second antigen-binding functional region, wherein the first antigen-binding functional region comprises at least one antigen-binding unit targeting TL1A comprising an immunoglobulin heavy chain variable domain (VH) and an immunoglobulin light chain variable domain (VL), wherein:

the VH comprises the amino acid sequence set forth in SEQ ID NO: 30, and the VL comprises the amino acid sequence set forth in SEQ ID NO 31;

or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 30 or 31, and maintaining the specific binding to TL1A;

and the second antigen-binding functional region comprises at least one immunoglobulin single variable domain specifically binding to IL-23p19 comprising the amino acid sequence set forth in SEQ ID NO: 77, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 77, and maintaining the specific binding to IL-23p19.

3. The bispecific antigen-binding molecule according to claim 1, wherein the immunoglobulin single variable domain is a VHH.

4. The bispecific antigen-binding molecule according to claim 3, wherein the immunoglobulin single variable domain is a humanized VHH.

5. The bispecific antigen-binding molecule according to claim 1, wherein the antigen-binding unit targeting TL1A is F(ab), F(ab'), $F(ab')_2$, scFab, Fd, Fv, dsFv, dAb, diabody or scFv.

6. The bispecific antigen-binding molecule according to claim 5, wherein the antigen-binding unit targeting TL1A is F(ab), and the VH is connected to the immunoglobulin CH1 domain, and the VL is connected to the immunoglobulin light chain constant domain.

7. The bispecific antigen-binding molecule according to claim 6, wherein the immunoglobulin CH1 domain is a human immunoglobulin CH1 domain; and/or, the immunoglobulin light chain constant domain is derived from a human λ light chain constant domain or a human κ light chain constant domain.

8. The bispecific antigen-binding molecule according to claim 6, wherein the immunoglobulin CH1 domain sequence comprises the amino acid sequence set forth in SEQ ID NO: 117, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 117; and/or, the immunoglobulin light chain constant domain sequence comprises the amino acid sequence set forth in SEQ ID NO: 82, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 82.

9. The bispecific antigen-binding molecule according to claim 1, further comprising an immunoglobulin Fc domain.

10. The bispecific antigen-binding molecule according to claim 9, wherein the immunoglobulin Fc domain is a human immunoglobulin Fc domain.

11. The bispecific antigen-binding molecule according to claim 9, wherein the immunoglobulin Fc domain further comprises one or more amino acid mutations selected from $L_{234}A$, $L_{235}A$, $M_{252}Y$, $S_{254}T$, $T_{256}E$ and $K_{447}del$.

12. The bispecific antigen-binding molecule according to claim 9, wherein the immunoglobulin Fc domain comprises the amino acid sequence set forth in SEQ ID NO: 99, 100, 118 or 119, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 99, 100, 118 or 119.

13. The bispecific antigen-binding molecule according to claim 1, wherein the first antigen-binding functional region comprises a plurality of antigen-binding units targeting TL1A, and/or the second antigen-binding functional region comprises a plurality of immunoglobulin single variable domains specifically binding to IL-23p19.

14. The bispecific antigen-binding molecule according to claim 1, wherein the numbers of the first antigen-binding functional region and the second antigen-binding functional region are each independently 1, 2 or more than 2.

15. The bispecific antigen-binding molecule according to claim 13, wherein the plurality of antigen-binding units, the plurality of immunoglobulin single variable domains, and/or the plurality of antigen-binding functional regions are optionally connected via a linker.

16. The bispecific antigen-binding molecule according to claim 9, comprising:

an immunoglobulin heavy chain, which comprises from the N-terminus to the C-terminus: the VH, the immunoglobulin CH1 domain, the Fc domain, an optional linker and the immunoglobulin single variable domain; and an immunoglobulin light chain, which comprises from the N-terminus to the C-terminus: the VL and the immunoglobulin light chain constant domain.

17. The bispecific antigen-binding molecule according to claim 16, wherein the linker is (GS)n, (GGS)n, (GGGS)n or (GGGGS)n, wherein n is selected from 1, 2, 3, 4 or 5.

18. The bispecific antigen-binding molecule according to claim 1, wherein the immunoglobulin heavy chain comprises the amino acid sequence set forth in SEQ ID NO: 115 or 116, or an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 115 or 116; and the immunoglobulin light chain comprises the amino acid sequence set forth in SEQ ID NO: 92, or an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 92.

19. A composition comprising the bispecific antigen-binding molecule according claim 1.

20. The composition according to claim 19, wherein the composition is a pharmaceutical composition, the pharmaceutical composition further comprises at least one pharmaceutically acceptable carrier and/or excipient, and optionally comprises one or more other pharmaceutically active therapeutic agents.

21. A method for treating, preventing or alleviating inflammatory diseases and/or autoimmune diseases comprising administering a therapeutically effective amount of the bispecific antigen-binding molecule according to claim 1 to a subject in need thereof.

22. The method according to claim 21, wherein the inflammatory diseases and/or autoimmune diseases are selected from asthma, rheumatoid arthritis, multiple sclerosis, inflammatory bowel disease, systemic lupus erythematosus, ankylosing spondylitis or psoriasis.

23. The method according to claim 21 further comprising using in combination with one or more other therapeutic agents for treating inflammatory diseases and/or autoimmune diseases.

* * * * *